US009409962B2

(12) United States Patent
Trybus et al.

(10) Patent No.: US 9,409,962 B2
(45) Date of Patent: Aug. 9, 2016

(54) METHODS AND COMPOSITIONS FOR EXPRESSING FUNCTIONAL CLASS XIV MYOSIN

(71) Applicant: University of Vermont and State Agricultural College, Burlington, VT (US)

(72) Inventors: Kathleen M. Trybus, Burlington, VT (US); Gary E. Ward, Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 14/712,466

(22) Filed: May 14, 2015

(65) Prior Publication Data
US 2015/0329610 A1 Nov. 19, 2015

Related U.S. Application Data

(60) Provisional application No. 61/993,752, filed on May 15, 2014.

(51) Int. Cl.
*C12Q 1/25* (2006.01)
*C07K 14/47* (2006.01)
*C12Q 1/34* (2006.01)

(52) U.S. Cl.
CPC ............. *C07K 14/4716* (2013.01); *C12Q 1/34* (2013.01); *G01N 2333/4712* (2013.01)

(58) Field of Classification Search
None
See application file for complete search history.

(56) References Cited

U.S. PATENT DOCUMENTS

2008/0274113 A1 11/2008 Bergman et al.

OTHER PUBLICATIONS

Andrade, M.A. et al., "Comparison of Arm and Heat protein repeats", J Mol Biol, May 25, 2001, vol. 309, pp. 1-18.
Corpet F. "Multiple sequence alignment with hierarchical clustering", Nucleic Acids Research, Nov. 25, 1988, vol. 16, pp. 10881-10890.
Douse, C.H. et al., "Targeting a Dynamic Protein—Protein Interaction: Fragment Screening against the Malaria Myosin a Motor Complex", ChemMedChem, 2015, vol. 10, pp. 134-143.
Egarter, S. et al., "The Toxoplasma Acto-MyoA Motor Complex Is Important but Not Essential for Gliding Motility and Host Cell Invasion", PLoS One, Mar. 2014, vol. 9, e91819.
Frénal, K. et al., "Plasticity between MyoC- and MyoA- Glideosomes: An Example of Functional Compensation in Toxoplasma gondii Invasion", PLOS, Nov. 2014, vol. 10, pp. 1-21.
Kortagere, S. et al., "Structure-based Design of Novel Small-Molecule Inhibitors of Plasmodium falciparum", J. Chem. Inf. Model., 2010, vol. 50, pp. 840-849.
Kortagere, S. et al., "Rapid discovery of inhibitors of Toxoplasma gondii using hybrid structure-based computational approach", J Comput Aided Mol Des, published online: Feb. 26, 2011, 9 pages.
Pearson, W.R. et al., "Comparision of DNA sequences with protein sequences", Genomics, Nov. 15, 1997, vol. 46, pp. 24-36.
Williams, M.J. et al., "Two Essential Light Chains Regulate the MyoA Lever Arm to Promote Toxoplasma Gliding Motility", mBio, Sep./Oct. 2015, vol. 6, pp. 1-16.
Andenmatten, Nicole, et al., "Conditional genome engineering in Toxoplasma gondii uncovers alternative invasion mechanisms", Nat Methods, Feb. 2013, Volusem 10, pp. 125-127.
Cheung, A. et al., "A small-molecule inhibitor of skeletal muscle myosin II", Nat Cell Biol., Jan. 2002, vol. 4, pp. 83-88.
Hall, Carolyn I. et al., "Chemical genetic screen identities Toxoplasma DJ-1 as a regulator of parasite secretion, attachment, and invasion", PNAS, Jun. 28, 2011, vol. 108, pp. 10568-10573.
Meissner, M. et al., "Role of Toxoplasma gondii myosin A in powering parasite gliding and host cell invasion", Science, Oct. 25, 2002, vol. 298, pp. 837-840.
Trybus, Kathleen M., "Myosin V from head to tail", Cell Mol Life Sci., May 2008, vol. 65, pp. 1378-1389.
Foth, B. J. et al, "New insights into myosin evolution and classification", PNAS, Mar. 7, 2006, vol. 103, pp. 3681-3686.
Sheffield, H. G., and M. L. Melton, "The Fine Structure and Reproduction of Toxoplasma Gondii", J. Parasitol., Apr. 1968, vol. 54, pp. 209-226.
Gaskins, E. et al., "Identification of the Membrane Receptor of a Class XIV Myosin in Toxoplasma gondii" The Journal of Cell Biology, May 10, 2004, vol. 165, pp. 383-393.
Frénal, K. et al., "Functional Dissection of the Apicomplexan Glideosome Molecular Architecture", Cell Host Microbe, Oct. 21, 2010, vol. 8, pp. 343-357.
Nebl, T. et al., "Quantitative in vivo Analyses Reveal Calcium-dependent Phosphorylation Sites and Identities a Novel Component of the Toxoplasma Invasion Motor Complex", PLoS Pathogens, Sep. 2011, vol. 7, e1002222.
Heintzelman, M. B., and J. D. Schwartzman, "A Novel Class of Unconventional Myosins from Toxoplasma gondii", Journal of Molecular Biology, Aug. 8, 1997, vol. 271, pp. 139-146.
Herm-Gotz, A. et al., "Toxoplasma gondii Myosin A and its Light Chain: A Fast, single-headed, Plus-End-Directed Motor", The EMBO Journal, 2002, vol. 21, pp. 2149-2158.
Bement, W. M. and M. S. Mooseker, "TEDS Rule: A Molecular Rationale for Differential Regulation of Myosins by Phosphorylation of the Heavy Chain Head", Cell Motil. Cytoskeleton, 1995, vol. 31, pp. 87-92.
Kinose, F. et al., "Glycine 699 is Pivotal for the Motor Activity of Skeletal Muscle Myosin", Journal of Cell Biology, Aug. 1996, vol. 134, pp. 895-909.
Hettmann, C. et al., "A Dibasic Motif in the Tail of a Class XIV Apicomplexan Myosin Is an Essential Determinant of Plasma Membrane Localization", Molecular Biology of the Cell, Apr. 2000, vol. 11, pp. 1385-1400.

(Continued)

*Primary Examiner* — Jim Ketter
(74) *Attorney, Agent, or Firm* — Finch & Maloney PLLC

(57) ABSTRACT

The invention, in part, includes methods and compounds useful to prepare and functional class XIV myosin. Functional class XIV myosin prepared using methods of the invention may be useful to screen for and identify compounds that inhibit and treat parasitic infections and contamination.

21 Claims, 7 Drawing Sheets

(56) References Cited

OTHER PUBLICATIONS

Heaslip, A. T. et al., "A Small-Molecule Inhibitor of T. gondii Motility Induces the Posttranslational Modification of Myosin Light Chain-1 and Inhibits Myosin Motor Activity", PLoS Pathogens, Jan. 2010, vol. 6, e1000720.

Leung, J. M. et al., "Disruption of TgPHIL1 Alters Specific Parameters of Toxoplasma gondii Motility Measured in a Quantitative, Three-Dimensional live Motility Assay", PLoS One, Jan. 2014, vol. 9, e85763.

Hakansson, S. et al., "Time-Lapse Video Microscopy of Gliding Motility in Toxoplasma gondii Reveals a Novel, Biphasic Mechanism of Cell Locomotion", Molecular Biology of the Cell, Nov. 1999, vol. 10, pp. 3539-3547.

Moore, J. R. et al., "Does the Mysoin V Neck Region Act as a Lever?", J. Muscle Res. Cell Motil, 2004, vol. 25, pp. 29-35.

Warshaw, D. M. et al., "The Light Chain Binding Domain of Expressed Smooth Muscle Heavy Meromyosin Acts as a Mechanical Lever", Journal of Biology Chemistry, Nov. 2000, vol. 275, pp. 37167-37172.

Tyska, M. J. and D. M. Warshaw, "The Myosin Power Stroke", Cell Motil Cytoskeleton, Jan. 2002, vol. 51, pp. 1-15.

Trybus, K. M., "Regulation of Expressed Truncated Smooth Muscle Myosins" The Journal of Biological Chemistry, Aug. 19, 1994, vol. 269, pp. 20819-20822.

Pato, M. D., et al., "Baculovirus Expression of Chicken Nonmuscle Heavy Meromyosin II-B", The Journal of Biological Chemistry, Feb. 2, 1996, vol. 271, pp. 2689-2695.

De La Cruz, E. M. et al., "The Kinetic Mechanism of Myosin V", PNAS, Nov. 23, 1999, vol. 96, pp. 13726-13731.

Trybus, K. M. et al., "Kinetic Characterization of a Monomeric Unconventional Myosin V Construct", The Journal of Biological Chemistry, Sep. 24, 1999, vol. 274, pp. 27448-27456.

Wang, F. et al., "Effect of ADP and Ionic Strength on the Kinetic and Motile Properties of Recombinant Mouse Myosin V", The Journal of Biological Chemistry, Feb. 11, 2000, vol. 275, pp. 4329-4335.

Wells, A. L. et al., "Myosin VI is an Actin-based Motor that Moves Backwards", Nature, Sep. 30, 1999, vol. 401, pp. 505-508.

Yang, Y. et al., "Myosin VIIB from *Drosophila* Is a High Duty Ratio Motor", The Journal of Biological Chemistry, Sep. 16, 2005, vol. 280, pp. 32061-32068.

Chow, D. et al., "Folding of the Striated Muscle Myosin Motor Domain", The Journal of Biological Chemistry, Sep. 27, 2002, vol. 277, pp. 36799-36807.

Srikakulam, R. and D. A. Winkelmann, "Myosin II Folding is Mediated by a Molecular Chaperonin", The Journal of Biological Chemistry, Sep. 17, 1999, vol. 274, pp. 27265-27273.

Srikakulam, R. and D. A. Winkelmann, "Chaperone-mediated Folding and Assembly of Myosin in Striated Muscle" Journal of Cell Science, 2004, vol. 117, pp. 641-652.

Barral, J. M. et al., "Role of the Myosin Assembly Protein UNC-45 as a Molecular Chaperone for Myosin", Science, Jan. 25, 2002, vol. 295, pp. 669-671.

Liu, L. et al., "Unc45 Activates Hsp90-dependent Folding of the Myosin Motor Domain", The Journal of Biological Chemistry, May 9, 2008, vol. 283, pp. 13185-13193.

Srikakulam, R. et al., "Unc45b Forms a Cytosolic Complex with Hsp90 and Targets the Unfolded Myosin Motor Domain", PLoS One, May 2008, vol. 3, e2137.

Scheufler, C. et al., "Structure of TPR Domain-Peptide Complexes: Critical Elements in the Assembly of the Hsp70-Hsp90 Multichaperone Machine", Cell, Apr. 14, 2000, vol. 101, pp. 199-210.

Hutagalung, A. H. et al., "The UCS Family of Myosin Chaperones", Journal of Cell Science, 2002, vol. 115, pp. 3983-3990.

Trybus, K. M. "Biochemical Studies of Myosin", Methods, Dec. 2000, vol. 22, pp. 327-335.

Philo, J. , "A Method for Directly Fitting the Time Derivative of Sedimentation Velocity Data and an Alternative Algorithm for Calculating Sedimentation Coefficient Distribution Functions", Anal Biochem., Mar. 15, 2000, vol. 279, pp. 151-163.

Cronan, J. E., Jr., "Biotination of Proteins in Vivo", The Journal of Biological Chemistry, Jun. 25, 1990, vol. 265, pp. 10327-10333.

Beckingham, K., "Use of Site-directed Mutations in the Individual $Ca^{2+}$-binding Sites of Calmodulin to Examine $Cat^{2+}$-induced Conformational Changes", The Journal of Biological Chemistry, Apr. 5, 1991, vol. 266, pp. 5027-6030.

Bergman, L. W. et al., "Myosin A tail domain interacting protein (MTIP) localizes to the inner membrane complex of Plasmodium sporozoites", Journal of Cell Science, 2003, vol. 116, pp. 39-49.

Bosch, J. et al., "The closed MTIP-MyosinA-tail complex from the malaria parasite invasion machinery", Journal of Molecular Biology, Sep. 7, 2007, vol. 372, pp. 77-88.

Turley, S. et al., "The compact confirmation of the Plasmodium knowlesi myosin tail interacting protein (MTIP) in complex with the C-terminal helix of myosin A", Mol. Biochem. Parasitol., Aug. 2013, vol. 190, pp. 56-59.

Treeck, M. et al., "The Phosphoproteomes of Plasmodium falciparum and Toxoplasma gondii reveal unusual adaptations within and beyond the parasites' boundaries", Cell Host Microbe, Oct. 20, 2011, vol. 10, pp. 410-419.

Sakamoto, T. et al., "Neck Length and Processivity of Myosin V", The Journal of Biological Chemistry, Aug. 1, 2003, vol. 278, pp. 29201-29207.

Douse, C. H. et al., "Regulation of the Plasmodium Motor Complex; Phosphorylation of Myosin A Tail-Interacting Protein (MTIP) Loosens its Grip on MyoA", The Journal of Biological Chemistry, Oct. 26, 2012, vol. 287, pp. 36968-36977.

Lee, C. E et al., "X-ray crystal structure of the UCS domain-containing UNC-45 myosin chaperone from *Drosophila melanogaster*", Structure, Mar. 9, 2011, vol. 19, pp. 397-408.

Shi, H. and G. Blobel, "UNC-45/CR01/She4p (UCS) protein forms elongated dimer and joins two myosin heads near their actin binding region", PNAS, Dec. 14, 2010, vol. 107, pp. 21382-21387.

Mishra, M. et al., "Hsp90 Protein in Fission Yeast Swo1p and UCS Protein Rng3p Facilitate Myosin II Assembly and Function", Eukaryotic Cell, Mar. 2005, vol. 4, pp. 567-576.

Ni, W. et al., "The myosin-binding UCS domain but not the Hsp90-binding TPR domain of the UNC-45 chaperone is essential for function in Caenorhabditis elegans", The Journal of Cell Science, 2011, vol. 124, pp. 3164-3173.

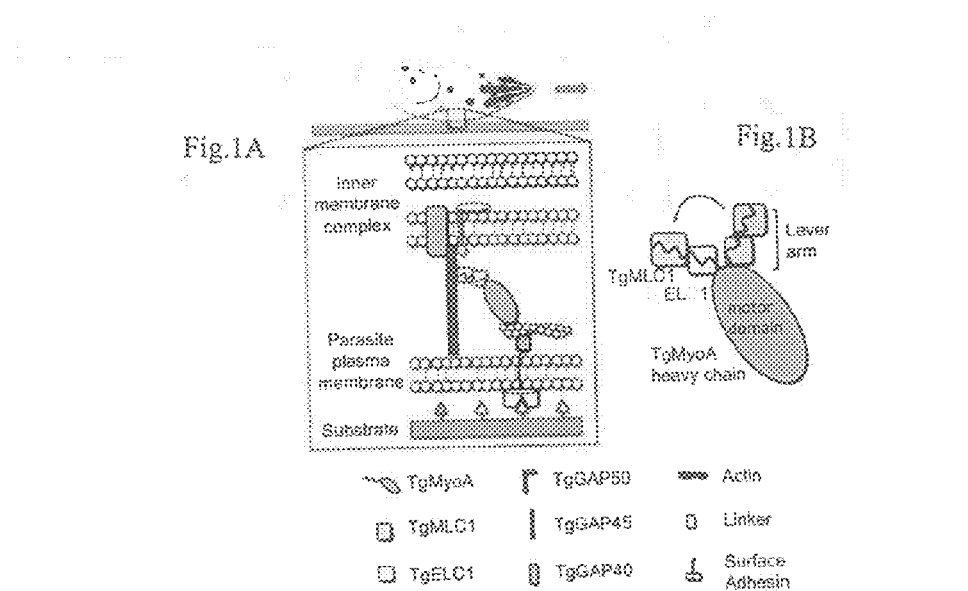
Fig. 1A
Fig. 1B
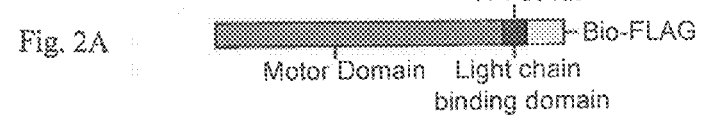
Fig. 2A
Fig. 2B
Fig. 3
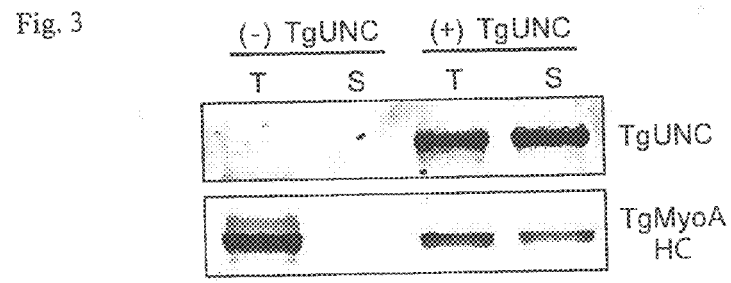

```
              10         20         30         40
DmUNC   MTNTINSEEVSDAGSYKDKGNEAFKASRWEEAVEKYGKAIKAGSK--------------
         :  .:   ..   . :..:: ::  ..:  :.: :..  .  .:
TgUNC   MEDLSNAM-LARLQALKEEGNAEFKRGKFESATEAYSRCLDDASDTLDKEPDVLGGACAA
              10         20         30         40         50

50              60         70         80
DmUNC   ------------HKELAVFYK-----------NRAAAYLKLGKYENAVEDCTESLKAAPG
                    .:: .. :           ::: :  ..  : :::...    :.
TgUNC   SLSSSDSQVAEPRKESPAILKRVAELKAQILCNRALCYQRTKQFAAAEADCTRAIALHPA
         60         70         80         90        100        110

90        100        110        120        130        140
DmUNC   DPKALFRRAQAYEALEKFEEAYKDATALFKADPGNKTVQPMLQ--RLHVVVEERSARNAK
         :. .:::  :.:    ..  .:  . ...:::: .: ::    : .:: ::..   .
TgUNC   YVKSYYRRAVALDAQGRRKECVEDLQTCLRLQPGNKEAQEMLAGVRDKVMKEEETRVEEQ
             120        130        140        150        160        170

150        160        170        180        190        200
DmUNC   TSTKVKQMMDLTFDLATPIDKRRAAANNLVVLAKEQTGAELLYKDHCIAKVASLTKVEKD
         ....     ..   ..: :.  .:  ....:    . .  .:  .::     :   . :
TgUNC   LP---ENLLTAGLNDVLTASKRVASLRQLGAFVQERKLRRQFLRDGGLRRVAVALKSQMD
         180        190        200        210        220        230

210        220        230        240
DmUNC   QDIYVN-MVHL-VAALCENSV------ERTKG---VLTELGVP---W--FMRVLDQKHEN
         ...  :  .:  .:  :...       :..:.        ..    :  . :...:. .
TgUNC   SELEGNGQPHRSLESLPETTASDPVASEESKSSADAVLPVSVEAACWELLLSVVQQHQAD
             240        250        260        270        280        290

250              260              270
DmUNC   CVSTAQFCLQT--------------ILN---ALSGLKNKPD-------------SKPDKE
         . :.  :::                .:.   :::::  .  :              .. :
TgUNC   DEDDANKALQTSVEAVNAPLQVDAPVLECRQALSGLWTPNDFLVRLRQLLRAGVARSDGL
             300        310        320        330        340        350

280              290        300        310
DmUNC   LCTRNNREI-----------DTLLT---CLVYSIT-----DRTISGAARDGVIELITRN
         :  :.:            :  ::    :.:  .      : .. .:.   .:.
TgUNC   AATAANEEAGKLRTVWRGEACDRLLRTMGCVVQLQAAQFDEDASFLEACAAGLECIDSRE
             360        370        380        390        400        410

320              330        340        350
DmUNC   VHYTAL--------EWAERL-------VEIR-GLCRLL-DVCSELEDYKYESAMDITGSSST
         :. .:.         .  .:         ...: :: . :   .  ::  ..:.
TgUNC   VQRAAVAALVGVADARRRLGGRVAAVRLRHGLEKCLEDALQVVSDAEHELAGEDARSQLA
             420        430        440        450        460        470

360            370              380        390
DmUNC   IASV-------CLARIYENMYY----------DEAKARFTDQIDEYIKDKLLAPDM------
         .:          ..:.  .  :           :. ...  . .: :.:.:
TgUNC   TASKKSDRLEAVSRLQGQTEYLIITLIALLADKDRGKEEPPDMSRLVDQLLSPYFRPCAD
             480        490        500        510        520        530
```

Fig. 11 continued

```
       400        410       420       430
DmUNC  ---ESKVRVTVAITAL----LNGPLDVGNQ-VVAREGILQMILAMA--------------TTD
       :: : .::,. :: :..  .:.  ...  .:: ..:: :           :.
TgUNC  PEESVVTLTVGLKALRLILTAAREVARAYLISASSILPYLLAAAAGGVGTAQSGAAGTAA
       540        550       560       570       580       590

440        450       460       470       480       490
DmUNC  DELQQRVACECLIAASSKKD-KAKALCEQGVDILKRL-YRSKNDG---IRVRALVGLCKLG
       . ::..: : ....: .   . ::..  .. . :.. .: : : .,:.  ..: .:
TgUNC  HRRQQEAALEVLLACMDFPELRATLLEANAVPVFAKVCSESANVGCWMRARLAAALARL-
       600        610       620       630       640       650

500                                510       520       530
DmUNC  SYGGQDAAIRPF-----------------GDG---AALKLAEACRRFLIKP-GKDKDI
       :  .:. :. :                  ::: .: ,::       .: ..
TgUNC  SVHDEDVRIQVFDSIDFYDVLDVLVSEIRAAGGDGRQVAEPSTEAKNAQKGQPMAVGEET
       660        670       680       690       700       710

540        550       560       570       580
DmUNC  RRWAADGLAYLTLDAECKEKLIEDKAS---IHALMDLARGGNQSCLYGVVTTFV----NLC
       :. ..:.:   .. .. ..:    .    ...:...: :....  ..           .:
TgUNC  FRFLLEIFFFLSLHGDFKARLVTGKKGARVLRTLLQVANGAGKKGASSSLTRYLLLQSLC
       720        730       740       750       760       770

590                600                 610       620
DmUNC  NAY-----EKQ---------------EMLPEMIELAKF------AKQHIPEEHELDDVDF
       :     ..:           :.: .. :: :      ::          ; .:: .
TgUNC  NIMRSREDRQRQRRKGEVGSPLADVDDEQLQQLEELFKKLPEGAKPAANGEVDLGDKAL
       780        790       800       810       820       830

630        640       650       660       670
DmUNC  INKRITVLANEGITTAL-----CALAKTESHNSQELIARVLNAVCGLKELRGKVVQEGGVK
       ,.   .:.  ... :.      :: . .. ::. .  ...: ::  ..  ::,,:::;..
TgUNC  ATQLRDMLLDLNVVHAIAVNVCA-TPFPSSNVLCAAAQALKFLCEDSRHRGRAVQEGGIR
       840        850       860       870       880       890

680        690       700       710       720       730
DmUNC  ALLRMA---LEGTEKGKRHATQALARIGITINPEVSFSGQRSLDVIRPLLNLLQQDCTALE
       .:: :  :: .::: ::  ::  .  ::  ..:::,. : :  : .:    :
TgUNC  TLLVAASGLEEFPDDQRNARQAAAQLCITTNPAL-FSYRESLDLV-PCLAPLLKDRHELL
       900        910       920       930       940       950

740        750       760       770       780       790
DmUNC  NFESLMALTNLASMNESVRQRIIKEQGVSKIEYYLMEDHLYLTRAAA--QCLCNLVMSEDV
       ..:. .::::::  ...: ::,:   ::   .:  .  .: :::,.  ::: : :  :
TgUNC  QYEGALALTNLCALSEEVRMRAWL-GGVWEGFEDLMFGENELLRAAGLEGWCNLSASPTV
       960        970       980       990       1000      1010

800        810       820       830       840
DmUNC  -------IKMFEGNNDRVK-----FLALLCEDEDEETATACAGALAII-TSVSVKCCEKIL
              ,. ::.....:.    .::.  :  .. .. .: ..:::::.. .. .: :
TgUNC  QAEIGKKMERFAAEKQEVQDVKLLIAFTRETNNPRAQSAAVAALAMLLANEKVARCLPAY
       1020       1030      1040      1050      1060      1070
```

Fig. 11 continued

```
        850       860       870          880       890
DmUNC  AIASWLDYLHTLIANPSPAVQHRGIVIILNMI------NAGEEIAKKLFETDIMELLSGL
       .. ..: .       . :.   :.  . .:.        .:: :    .. .:   :  .
TgUNC  SLFGNLALSLEEAKAEQEALIVRCVSALYNVWIELSSSEAGTETRMQIVKT----LQRNQ
         1080      1090      1100      1110      1120

900       910       920       930       940
DmUNC  GQLPDDTRAKAREVATQCLAAAERYRIIERSDNAEIPDVFAENSKISEIIDD
       .:  ...  :.:: :  :. ..  .    ::              ..
TgUNC  QKLTGDAQHLAKEVLTAELSQTNTHT------KESTPD-------------SS
         1130      1140     1150                    1160
```

METHODS AND COMPOSITIONS FOR EXPRESSING FUNCTIONAL CLASS XIV MYOSIN

RELATED APPLICATIONS

This application claims benefit under 35 U.S.C. §119(e) of U.S. Provisional Application No. 61/993,752, filed May 15, 2014 the content of which is incorporated by reference herein in its entirety.

GOVERNMENT INTEREST

This invention was made with government support under grant numbers AI054961 and R01 GM078097 awarded by the National Institutes of Health. The Government has certain rights in the invention.

FIELD OF THE INVENTION

The invention, in part, relates to methods to prepare, assess, and utilize functional class XIV myosin.

BACKGROUND OF THE INVENTION

Class XIV myosins play an important role in the life cycle of apicomplexan parasites of medical and/or veterinary importance, such as *Plasmodium* spp, *Toxoplasma gondii*, *Sarcocystis neurona* and *Cryptosporidium parvum*. One example of an apicomplexan parasite is *Toxoplasma gondii*, which is a member of the phylum Apicomplexa and is a common infectious agent of humans that can result in health risks to immune-compromised individuals and the developing fetus. This obligate intracellular parasite must penetrate a host cell and replicate to survive. The invasive stage of the parasite relies on a unique form of substrate-based motility called gliding motility, which is driven by a class XIVa myosin motor, TgMyoA that is powered by an actomyosin-based complex, which is called the "glideosome". The class XIV myosin TgMyoA heavy chain is one of eleven myosin heavy chains found in *T. gondii* (1) and is an essential component of the glideosome, which is necessary for efficient parasite motility, invasion, and egress from the host. Parasites lacking TgMyoA are avirulent in a mouse model of parasite infection (2).

The TgMyoA motor is located between the plasma membrane and the inner membrane complex (IMC), a double membrane that is continuous around most of the cell (3). TgGAP50 (a 50 kDa gliding associated protein), an integral membrane glycoprotein of the IMC, acts as a membrane receptor for the motor (4); TgMyoA is linked indirectly to TgGAP50 through an apicomplexan-specific N-terminal extension of its regulatory light chain, TgMLC1, and TgGAP45 (a 45 kDa gliding associated protein). Several other proteins, including TgGAP40 (a 40 kDa gliding associated protein), TgGAP70 (a 70 kDa gliding associated protein), and TgELC1 (a putative essential light chain) have recently been identified as additional components of this myosin motor complex (5, 6). The mechanism by which the motor complex generates motility has remained unclear.

SUMMARY OF THE INVENTION

In one aspect of the invention, methods for preparing a functional class XIV myosin are provided. Compositions that include functional class XIV myosin polypeptides and their encoding polynucleotides are also provided in some aspects of the invention. In some aspects of the invention, methods of using functional class XIV myosin are provided and may include, in some aspects, use in screening assays to identify candidate compounds that reduce the level of activity of a class XIV myosin polypeptide.

According to one aspect of the invention, methods of producing a functional class XIV myosin polypeptide are provided. The methods include co-expressing three or more polynucleotides in an expression-system cell, wherein the three or more polynucleotides comprise a class XIV heavy chain polypeptide-encoding polynucleotide, a first myosin light chain polypeptide-encoding polynucleotide, and a parasite co-chaperone polypeptide-encoding polynucleotide, wherein the three or more polynucleotides are co-expressed in the cell under conditions suitable to produce a functional class XIV myosin polypeptide comprising the class XIV heavy chain polypeptide and the first myosin light chain polypeptide. In some embodiments, the class XIV heavy chain polypeptide-encoding polynucleotide, the parasite co-chaperone polypeptide-encoding polynucleotide, and the first myosin light chain polypeptide-encoding polynucleotide are each independently selected from a *Toxoplasma*, *Plasmodium*, *Neospora*, *Sarcocystis*, *Eimeria*, or *Cryptosporidium* class XIV heavy chain polypeptide-encoding polynucleotide or a functional variant thereof; a parasite co-chaperone polypeptide-encoding polynucleotide or a functional variant thereof; and a myosin light chain polypeptide-encoding polynucleotide or a functional variant thereof, respectively. In certain embodiments, the *Toxoplasma* is *Toxoplasma gondii*; *Plasmodium* is *Plasmodium falciparum*, *P. vivax*, *P. knowlesi*. *P. ovale*, or *P. malariae*; *Neospora* is *Neospora caninu* or *Neospora hughesi*; *Sarcocystis* is *Sarcocystis neurona*, *bovihominis* (*S. hominis*,), or *S. suihominis*; *Eimeria* is *Eimeria tenella*, *E. bovis*, *E. necatrix*, *E. ellipsoidalis*, or *E. zuernii*; and *Cryptosporidium* is *Cryptosporidium parvum*, *C. hominis*, *C. canis*, *C. felis*, *C. meleagridis*, or *C. muris*. In some embodiments, co-expressing includes co-infecting the expression-system cell with one or more expression vectors each including one or more of the three or more polynucleotides. In certain embodiments, the one or more expression vectors is a viral expression vector. In some embodiments, co-infecting the expression-system cell includes co-infecting with one or more expression vectors comprising one or more of the class XIV heavy chain polypeptide-encoding polynucleotide operably linked to an independently selected promoter, the first myosin light chain polypeptide-encoding polynucleotide operably linked to an independently selected promoter, and the parasite co-chaperone polypeptide-encoding polynucleotide operably linked to an independently selected promoter. In some embodiments, co-infecting the expression-system cell includes co-infecting with a first expression vector comprising the class XIV heavy chain polypeptide-encoding polynucleotide operably linked to an independently selected promoter, a second expression vector comprising the first myosin light chain polypeptide-encoding polynucleotide operably linked to an independently selected promoter, and a third expression vector comprising the parasite co-chaperone polypeptide-encoding polynucleotide operably linked to an independently selected promoter. In some embodiments, the one or more of the expression vectors additionally comprises one or more polynucleotides that encode: a myosin light chain-1 (MLC1) polypeptide or functional variant thereof, a tail domain interacting protein (MTIP) or functional variant thereof, an essential light chain-1, (ELC1) polypeptide or functional variant thereof, an essential like light chain, calmodulin or a functional variant thereof, or a glideosome associated protein-45 (GAP45) or a functional variant thereof. In some embodiments, one or more of the expression vectors additionally comprise at least one polynucleotide sequence that encodes a detectable label. In some embodiments, the detectable label comprises one or more FLAG tags, biotin acceptor sites, Myc tags, His tags, or Ty1 tags. In certain embodiments, the amino acid sequence of the biotin acceptor site comprises the sequence set forth as SEQ ID NO:21 or a functional variant thereof; the amino acid sequence of one or more of the Myc tags comprises the sequence set forth as SEQ ID NO:22 or a functional variant thereof; and the amino acid sequence of the one or more of the Ty1 tags comprises the sequence set forth as SEQ ID NO:23 or a functional variant thereof. In some embodiments, the parasite co-chaperone polypeptide-encoding polynucleotide sequence comprises a UNC-45/Cro1/She4p (UCS) chaperone polynucleotide sequence, or functional variant thereof. In some embodiments, the parasite co-chaperone polypeptide is derived from the sequence of a *toxoplasma gondii* UCS-45 homolog, a *Toxoplasma* UNC (TgUNC) polypeptide, or a functional variant thereof. In some embodiments, the TgUNC polypeptide comprises the amino acid sequence set forth as SEQ ID NO:12, or a functional variant thereof. In certain embodiments, the TgUNC polypeptide encoded by the polynucleotide sequence set forth as SEQ ID NO:11, or a functional variant thereof. In some embodiments, the TgUNC polypeptide functional variant is a truncated TgUNC polypeptide. In certain embodiments, the truncated TgUNC polypeptide comprises the amino acid sequence set forth as SEQ ID NO:14. In some embodiments, the truncated TgUNC polypeptide is encoded by the polynucleotide sequence set forth as SEQ ID NO:13. In some embodiments, the parasite co-chaperone is derived from the sequence of a *Plasmodium falciparum* UCS-45 homolog, a *Plasmodium falciparum* UNC (PfUNC) polypeptide, or a functional variant thereof. In certain embodiments, the PfUNC parasite co-chaperone polypeptide comprises the amino acid sequence set forth as SEQ ID NO:4, or a functional variant thereof. In some embodiments, the polynucleotide sequence of the PfUNC parasite co-chaperone comprises the sequence set forth as SEQ ID NO:3, or a functional variant thereof. In some embodiments, the PfUNC functional variant is a truncated PfUNC polypeptide. In certain embodiments, the truncated PfUNC polypeptide comprises the amino acid sequence set forth as SEQ ID NO:42, or a functional variant thereof. In some embodiments, the expression system is a baculovirus/insect cell expression system. In some embodiments, the expression-system cell is a Sf9 cell. In certain embodiments, the class XIV myosin heavy chain polypeptide comprises a TgMyoA amino acid sequence set forth as SEQ ID NO:16 or a functional variant thereof. In some embodiments, the class XIV myosin heavy chain TgMyoA amino acid sequence is encoded by the polynucleotide sequence set forth as SEQ ID NO:15, or a functional variant thereof. In certain embodiments, the class XIV myosin heavy chain polypeptide comprises a PfMyoA amino acid sequence set forth as SEQ ID NO:2 or a functional variant thereof. In some embodiments, the class XIV myosin heavy chain PfMyoA amino acid sequence is encoded by the polynucleotide sequence set forth as SEQ ID NO:1, or a functional variant thereof. In some embodiments, the class XIV myosin heavy chain polypeptide is a truncated class XIV myosin heavy chain polypeptide derived from *Plasmodium falciparum* and comprises the amino acid sequence set forth as SEQ ID NO:24 or a functional variant thereof, or comprises the amino acid sequence set forth as SEQ ID NO:26 or a functional variant thereof. In certain embodiments, the class XIV myosin heavy chain polypeptide is a truncated class XIV myosin heavy chain polypeptide derived from *Toxoplasma gondii* and comprises the amino acid sequence set forth herein as SEQ ID NO:25 or a functional variant thereof, or comprises the amino acid sequence set forth as SEQ ID NO:27 or a functional variant thereof. In some embodiments, the first myosin light chain polypeptide is a regulatory light chain (MLC1) polypeptide sequence derived from a *Toxoplasma gondii* regulatory light chain polypeptide sequence, or derived from a *Plasmodium falciparum* regulatory light chain polypeptide sequence. In some embodiments, the first myosin light chain polypeptide comprises the amino acid sequence forth as SEQ ID NO:18 or a functional variant thereof. In some embodiments, the first myosin light chain polypeptide is encoded by the polynucleotide sequence set forth as SEQ ID NO:17 or a functional variant thereof. In certain embodiments, the first myosin light chain polypeptide comprises the amino acid sequence set forth as SEQ ID NO:6 or a functional variant thereof. In some embodiments, the first myosin light chain polypeptide is encoded by the polynucleotide sequence set forth as SEQ ID NO:5 or a functional variant thereof. In some embodiments, the method also includes isolating the expressed functional class XIV myosin polypeptide. In certain embodiments, the method also includes assaying the function of the expressed functional class XIV myosin polypeptide. In some embodiments, the assay comprises an in vitro motility assay, a binding assay, an ATP co-sedimentation assay, or an ATPase activity assay. In some embodiments, the method also includes additionally co-infecting the expression-system cell with an expression vector comprising a second myosin light chain encoding polynucleotide; and co-expressing the class XIV heavy chain polynucleotide, the first and second myosin light chain polynucleotides, and the parasite co-chaperone polynucleotide under conditions suitable to produce a functional class XIV myosin polypeptide comprising the class XIV heavy chain polypeptide and the first and second myosin light chain polypeptides. In certain embodiments, the second myosin light chain polypeptide-encoding polynucleotide encodes a *Toxoplasma, Plasmodium, Neospora, Sarcocystis, Eimeria,* or *Cryptosporidium* myosin light chain polypeptide or a functional variant thereof. In some embodiments, the *Toxoplasma* is *Toxoplasma gondii; Plasmodium* is *Plasmodium falciparum, P. vivax, P. knowlesi. P. ovale,* or *P. malariae; Neospora* is *Neospora caninu* or *Neospora hughesi; Sarcocystis* is *Sarcocystis neurona, bovihominis* (*S. hominis,*), or *S. suihominis; Eimeria* is *Eimeria tenella, E. bovis, E. necatrix, E. ellipsoidalis,* or *E. zuernii*; and *Cryptosporidium* is *Cryptosporidium parvum, C. hominis, C. canis, C. felis, C. meleagridis,* or *C. muris*. In some embodiments, the first myosin light chain polypeptide is a regulatory light chain polypeptide and the second myosin light chain polypeptide is an essential light chain polypeptide. In some embodiments, the second myosin light chain is derived from a *Toxoplasma gondii* myosin light chain sequence or a *Plasmodium falciparum* myosin light chain sequence. In certain embodiments, the second myosin light chain polypeptide comprises the amino acid sequence set forth as SEQ ID NO:6, 8, 18, or 48, or a functional variant thereof. In some embodiments, the second myosin light chain polypeptide is encoded by the polynucleotide sequence set forth as SEQ ID NO:5, 7, 17, or 47.

According to another aspect of the invention, a functional class XIV myosin polypeptide prepared by the method of any one of the embodiments of the aforementioned claims is provided. In some embodiments, the class XIV myosin polypeptide is an isolated functional class XIV myosin polypeptide.

According to yet another aspect of the invention, methods of determining an activity of a class XIV myosin polypeptide are provided. The methods include (a) preparing a functional class XIV myosin polypeptide as set forth in an embodiment of any of the aforementioned methods; (b) assaying an activity of the prepared functional class XIV myosin polypeptide; and (c) assessing the results of the assay as a determination of activity in the functional class XIV myosin polypeptide. In certain embodiments, the assay comprises an in vitro motility assay, a binding assay, or an ATPase activity assay. In some embodiments, the activity comprises actin movement.

According to yet another aspect of the invention, methods of identifying a candidate compound to inhibit a parasite that expresses a class XIV myosin polypeptide are provided. The methods including (a) preparing a functional class XIV myosin polypeptide as set forth in an embodiment of any of the aforementioned methods; (b) contacting the prepared class XIV myosin polypeptide with a candidate compound under conditions suitable to determine an activity of the class XIV myosin polypeptide; (c) determining the activity of the class XIV myosin polypeptide; and (d) comparing the determined activity with a control activity determination, wherein a decrease in the determined activity in the contacted class XIV myosin polypeptide compared to the control activity determination identifies the compound as a candidate compound to inhibit a parasite that expresses the class XIV myosin polypeptide. In some embodiments, the control activity is activity determined in a functional class XIV myosin polypeptide not contacted with the candidate compound. In certain embodiments, the determining the activity comprises determining at least one of a level of the activity or the presence or absence of the activity. In some embodiments, the candidate compound alters the folding of the class XIV heavy chain polypeptide by the parasite co-chaperone polypeptide. In certain embodiments, the candidate compound alters the interaction between the class XIV heavy chain polypeptide and the first light chain polypeptide. In some embodiments, a means of determining the level of function of the class XIV myosin polypeptide comprises an in vitro motility assay, a binding assay, or an ATPase activity assay.

According to yet another aspect of the invention, methods of producing a class XIV myosin polypeptide are provided. The methods including co-expressing two or more polynucleotides in an expression-system cell, wherein the two polynucleotides comprise a class XIV heavy chain polypeptide-encoding polynucleotide and a parasite co-chaperone polypeptide-encoding polynucleotide, wherein the two or more polynucleotides are co-expressed in the cell under conditions suitable to produce a class XIV myosin polypeptide comprising the class XIV heavy chain polypeptide. In some embodiments, the class XIV heavy chain polypeptide-encoding polynucleotide and the a parasite co-chaperone polypeptide-encoding polynucleotide are each independently selected from a *Toxoplasma, Plasmodium, Neospora, Sarcocystis, Eimeria*, or *Cryptosporidium* class XIV heavy chain polypeptide or a functional variant thereof; and a from a *Toxoplasma, Plasmodium, Neospora, Sarcocystis, Eimeria*, or *Cryptosporidium* parasite co-chaperone polypeptide-encoding polynucleotide or a functional variant thereof. In certain embodiments, the method also includes co-expressing an essential myosin light chain polypeptide-encoding polynucleotide independently selected from a *Toxoplasma, Plasmodium, Neospora, Sarcocystis, Eimeria*, or *Cryptosporidium* essential myosin light chain-encoding polynucleotide or a functional variant thereof. In some embodiments, the *Toxoplasma* is *Toxoplasma gondii; Plasmodium* is *Plasmodium falciparum, P. vivax, P. knowlesi. P. ovale*, or *P. malariae; Neospora* is *Neospora caninu* or *Neospora hughesi; Sarcocystis* is *Sarcocystis neurona, bovihominis (S. hominis,)*, or *S. suihominis; Eimeria* is *Eimeria tenella, E. bovis, E. necatrix, E. ellipsoidalis*, or *E. zuernii*; and *Cryptosporidium* is *Cryptosporidium parvum, C. hominis, C. canis, C. felis, C. meleagridis*, or *C. muris*.

This invention is not limited in its application to the details of construction and the arrangement of components set forth in the following description or illustrated in the drawings. The invention is capable of other embodiments and of being practiced or of being carried out in various ways. The present invention is not intended to be limited to a system or method that must satisfy one or more of any stated objects or features of the invention. The present invention is not limited to the exemplary or primary embodiments described herein. Modifications and substitutions by one of ordinary skill in the art are considered to be within the scope of the present invention. Also, the phraseology and terminology used herein is for the purpose of description and should not be regarded as limiting. The use of 'including,' "comprising," or "having," "containing," "involving," and variations thereof herein, is meant to encompass the items listed thereafter and equivalents thereof as well as additional items.

Partial Listing of Sequences

SEQ ID NO: 1 *Plasmodium falciparum* 3D7 myosin A (MyoA) mRNA, complete cds, nucleotide sequence: XM_001350111, (also referred to herein as PfMyoA heavy chain)

```
atggctgttacaaatgaagaaataaaaacggcaagtaagattgttagaagagtttcaaatgtagaagcatttga
caaaagtggttcagtttttaagggttatcaaatatggactgatatatctccgacaatagaaaatgatccaaata
ttatgtttgtaaaatgtgttgtacaacaaggatcaaaaaaagaaaaattaaccgttgtacaaattgatccaccc
ggaacaggaactccatacgatattgatccaactcacgcatggaactgcaactctcaagtagaccccatgtcttt
tggtgatattggtcttttaaatcacaccaacatcccatgtgttcttgacttttaaagcacagatatttaaaaa
atcaaatatacaccactgctgttccccttattgttgcaataaacccatacaaggatttaggaaacacaactaat
gaatggattcgtagatatcgtgatacagctgatcatactaagttgccaccacacgtgttcacatgtgctaggga
agctttgtctaatctccatggtgtaaacaagagccaaactattattgtatctggtgaatctggtgcaggaaaaa
ccgaagcaacaaaacaaatcatgagatattttgcttcttctaagagtggaaatatggatttacgtattcagaca
gcaataatggctgcaaatccagttcttgaagcttttggtaatgcgaaaactataagaaataacaattcatctcg
ttttggtcgtttcatgcagttggttatatcccatgaaggaggtataagatacggttccgttgttgcttttctgt
tggaaaaatctagaattattacacaagatgataatgaaaggtcatatcatatattttatcaatttcttaagggt
gcaaatagtacgatgaaatctaaatttggtttaaaaggagttactgaatacaaattattgaacccaaattcaac
agaggtaagtggagtagatgatgtaaaagattttgaagaggtaattgaatcgttgaaaaatatggaattaagtg
aatcagatattgaagtaatattttcaatagtagctggtatattaacattaggaaatgtaagattaattgagaag
caagaagctggattaagtgatgctgctgctattatggatgaggatatgggtgtgtttaataaagcttgtgaatt
gatgtatttagaccctgaattaataaaaagggaaatattaattaaggtaactgttgctggaggaacaaaaattg
aaggtagatggaataaaaatgatgcagaagtgttgaaatcttccttatgtaaagctatgtatgagaaattgttt
ttatggataataagacatttgaattcaagaattgaaccagaaggaggatttaaaacatttatgggtatgttaga
```

| Partial Listing of Sequences |
|---|
| tattttggttttgaagtatttaaaaataattcattggaacaattatttattaacattactaacgaaatgcttc
agaaaaattttgtagatattgtttttgaaagagaatcaaaattatataaagacgaaggaatatcaacagctgaa
ttaaagtacaccagtaataaggaagtaataaaacgtactttgtgagaagggtaaatcagtactttcatacttaga
ggaccaatgtttagcacctggaggaaccgatgaaaagtttgtaagttcctgtgctacaaatttaaaggaaata
ataagtttaccccagcaaaagtagcatcgaataaaaattttataatacaacatactataggaccaattcaatat
tgtgctgaaagcttttttgcttaaaaacaaggatgtcttaagaggtgatttagttgaagtaattaaggattcccc
caatccaatagtacaacagttatttgaaggtcaagtaattgagaagggtaaaatagctaaaggttcattaatag
gttctcaattttaaatcaattgacatctttaatgaacttgataaatagtactgaaccacatttcatacgttgt
attaaaccaaatgaaaataaaaaaccattagaatggtgtgaaccaaaaatattaattcagcttcatgccttatc
aattttagaagcattagtattaagacaattaggatattcttatagaagaacctttgaagaattcttatatcaat
ataaatttgtggacattgctgctgctgaagattcatcagttgaaaaccaaaataaatgtgttaatatattaaag
ttgtctggactatctgaatccatgtataagataggaaaaagcatggtcttttttgaaacaagaaggtgcaaaaat
attgacaaaaatacaaagagagaaacttgttgaatgggaaaattgtgtgagtgtaattgaagctgctatactta
aacacaaatacaaacaaaaggttaacaaaaatataccttctcttttgagagtacaagctcatataagaaaaaaa
atggtagctcaataa. |

SEQ ID NO: 2 *Plasmodium falciparum* 3D7 myosin A (MyoA), amino acid sequence:
XP_001350147.1, (also referred to herein as PfMyoA heavy chain)
MAVTNEEIKTASKIVRRVSNVEAFDKSGSVFKGYQIWTDISPTIENDPNIMFVKCVVQQGSKKEKLTVVQIDPP
GTGTPYDIDPTHAWNCNSQVDPMSFGDIGLLNHTNIPCVLDFLKHRYLKNQIYTTAVPLIVAINPYKDLGNTTN
EWIRRYRDTADHTKLPPHVFTCAREALSNLHGVNKSQTIIVSGESGAGKTEATKQIMRYFASSKSGNMDLRIQT
AIMAANPVLEAFGNAKTIRNNNSSRFGRFMQLVISHEGGIRYGSVVAFLLEKSRIITQDDNERSYHIFYQPLKG
ANSTMKSKFGLKGVTEYKLLNPNSTEVSGVDDVKDFEEVIESLKNMELSESDIEVIFSIVAGILTLGNVRLIEK
QEAGLSDAAAIMDEDMGVFNKACELMYLDPELIKREILIKVTVAGGTKIEGRWNKNDAEVLKSSLCKAMYEKLF
LWIIRHLNSRIEPEGGFKTFMGMLDIFGFEVFKNNSLEQLFINITNEMLQKNFVDIVFERESKLYKDEGISTAE
LKYTSNKEVINVLCEKGKSVLSYLEDQCLAPGGTDEKFVSSCATNLKENNKFTPAKVASNKNFIIQHTIGPIQY
CAESFLLKNKDVLRGDLVEVIKDSPNPIVQQLFEGQVIEKGKIAKGSLIGSQFLNQLTSLMNLINSTEPHFIRC
IKPNENKKPLEWCEPKILIQLHALSILEALVLRQLGYSYRRTFEEFLYQYKFVDIAAAEDSSVENQNKCVNILK
LSGLSESMYKIGKSMVFLKQEGAKILTKIQREKLVEWENCVSVIEAAILKHKYKQKVNKNIPSLLRVQAHIRKK
MVAQ.

SEQ ID NO: 3 *Plasmodium falciparum* 3D7 Tetratricopeptide repeat family protein
(PFUNC), putative (PF14_0196) Nucleotide sequence: XM_001348333 mRNA, CDS (also
referred to herein as PFUNC, PFUNC and/or PfUnc)
atgcaggaatttgttatgaatattcttagtaaagaaaaaattgggaaaatagaaaaactaaaaaatgatgggaa
tgaattatatcgaaataaaaaatataaggaggctttatgtatatatgataatgctgtttgtgagttttgtggag
gttcaggtgatagtttaaaaattaaggaaatggtgaaagaattttcaaaaaatgatgagactaatgataataat
aaattatcagatgataataataataataatatgattgatgaaaataataagaaatgtgattttcttatatatg
tgaaattcaaaattttattcataaaaatatgccataatatcattatgttattatttcttagaagattttgaaa
aatctattgaatattgtttatatattaatgaaatgaacaataatcattataaaagttaccacacgcttgggttg
tgttatgagaaattaaaagattatcaaaagagtatacattattttgtaaggtgtaaaagtagtactttttaaaaaa
tcaaaacaataaaaataaagacaataataataaaagtgaaattaatcgaattaatgaaaagttacgtgatatta
tgaaaattatagatcaaaataaaaatgatccatataaaaatataagcaacattaaaaaatatcttcttgatgaa
aatacaaataatataaatgacattgaagaaaataataaaaaaattaaattgttacattctatttataatcaaaa
gttttatatactacttaaggaaaatattttttatttcttttttgaattttttaaaaaaaataatgacatatcaa
actatgacgattgcaataataataataataataataatttttatatagtcataatattaatagtttattattgaa
aaaacagccatttatgttatttataaaatattatccaaattagataatgaacatattatattgaaaattccaa
agatgataactataataaaaatcgtaatatatgtattaacaaattagataattcaaagcttcaatattattatg
atctagattatattaaaatgatttttatcctttaatgaatattttacaaaagattggatatatatttatataaaa
aaaaaaatcaatatattagaaaatttaaagtttttcaaaagatgaaaccttatataaagaacatgtagacatttt
aatctatatcataaatattatgaaatatgctcatgttataaaataatgattatattttaaatattattaattcct
attatttaaatagcgataattctaatattaataactctggtattaatgctcttacattcttatgtaaaaaaaaa
caattttttaacacaaaatagtaaggataataagaaaaaaaaaaaatgatttattagaaaatgcttaaaaaagaaaa
ttacttaaatatacaaaataataatacaaaataataataataataataatttattttttataagaatgaattta
ttgaatttcacttttcggactctcataaatatccattgtgtatcaattccgaaatcaaaaaaattttatacaaaat
gttattggtatgtatgaacacttttctagtagtatagaatataccttaattttaattttacttattatacatga
cccacaaagacctaaggaaaaagacatagaaatgaatgatgtaattttatgattgtatagataattattttcatc
ataatgaaaatattttgatagaatggtttgtatgtattaaatgtcttttcttagtagataaaaatattatatta
aattatttaataggaaaacagaatatattgtaaaaatcttacattttattacgaactgtataggaagaaaaac
taaagaagaattatccatatatatcgatgtcttattacttttattgaatatatcagaaatacgtttttatgttta
ctaattatattgatatgtatataaatataatgaaatctttaaattatgatcaatgcttttttgaaacttttacta
ggtacatttaaattatacatgcacaacatagactttaaacaacaaaatcaagataatgtggatttgttcttttta
tgcgaaagaaatattaaagcaattcttattaacatatgataatgatgcggacggaaaaaataacacgaataatg
ataaaagagaagaaaatgaggaacagacaagccatttgaattattctaatttaaattcgtacacatgctgtgtg
aaaaaatgtgatgataatgatacaaagaaaaaagatattataaaccaaagaaagatgaaaagaataagaaaca
ttgtgaacttgtagataagaaaaaaaaagatcatacatatacattcgaatatgagttgtgaaaaaacgttaa
aagatttaatagaaatgttatttttaagtttgcatattgaatattagtaaaacaattattagaggaaaaaaat
aattatattttatttttcttaataaaagtttggacatgatataaataaaaagaaattagataacacatatataata
tatatattgcaacactataaataatttaattttaacaaaaaaatgatgaaaaaataaaaagaagagaaattaata
aaactaatttatcaaattttgataatgaacaaatagaagctttagaacaattttatgataaaattaccaaaagaa
gctagacctaaaacagatccattatatgattatgagatgaagaaacaagtaacaaattaattgatttattatt
atataatgaaaaatatcaaatgaatcatattaatgataaaaataaaaataataataataatattaata
atggtaacgtatctccttttgtcatctaaatgttcctatacaaatggtaccattatcaatattatatataactttt
attaatagcaatttttttacaacaaatatagctgaatctgtatgtgaaataattcaaagtttgttaaaaatac
aaataatattggtatagttttagttaataatggattaaaaactttattattagcatctaagcatataacaaata
aaaagaattgtgctttagcattaagtgaaatatttatttatacgaacccgaaactttattcatttttatgaagca
tatgattctttaccttttattaattgaacaactaaagagtgatgaagaattattaatctttaaaacgttaatggc -continued Partial Listing of Sequences aataactaatattttaactattgatgaaaatgtagcaataaaagctatgcaattaaatttatggtataaatgtt
ttgatattctttcaacagaaaatgaatacataaaatctgctagcttagaatgtatatgcaatttatgttcccaa
tcacatgtacatcaatatatttatgataaatatcaaacaattatgaaatcaaaaaatgaatcagataaagatat
tttatttgttgatattcaaataatttattcatttaccatggaatatcaaaattataaatgtgttttttgcagcaa
ctggagctttaggtatgttgtcatctgatttgcgtttgccatattatttagttagaactaaagggattgatcat
attttctcatctttcaataataccaccgaccaaaatattttattacgtattttaacattttttcaacaacataat
gacgtgtgatgatataccggatgatatattaaagaaaataaagacttatgtggagaaaaagaaggatttaaatg
aagagaatactcaaatggcaaattttatactccagtag.

SEQ ID NO: 4 *Plasmodium falciparum* 3D7 Tetratricopeptide repeat family
protein, putative (PF14_0196) Amino acid sequence XP_001348369.1
(also referred to herein as PFUnc, PfUNC, and/or PFUNC)
MQEFVMNILSKEKIGKIEKLKNDGNELYRNKKYKEALCIYDNAVCEFCGGSGDSLKIKEMVKEFSKNDETNNIN
KLSDDNNNNNMIDENNKKCDFSYICEIQNLFIKICHNISLCYYFLEDFEKSIEYCLYINEMNNNHYKSYHTLGL
CYEKLKDYQKSIHYFDRCKIVLLKNQNNKNKDNNNKSEINRINEKLRDIMKIIDQNKNDPYKNISNIKKYLLDE
NTNNINDIEENNKKIKLLHSIYNQKFYILLKENIFLFLFDFIKKNNDISNYDDCNNNNNNNNNLYSHNINSLLLE
KTAIYVIYKILSKLDNEHIIIENSKDDNYNKNRNICINKLDNSKLQYYYDLDYIKMILSFNEYFTKDWIYNYIK
KKINILENLKFSKDETLYKEHVDILIYIINIMKYVYVINNDYILNIINSYYLNSDNSNINNSGINALTFLCKKK
QFLTQNSKDNRKKKNDLLEMLKKENYLNIQNNIQNNNNNNNYYFYKNEFIEFHFSDSHKYPLCINSEIKKIIQN
VIGMYEHFSSSIEYTLILIFTLLHDPQRPKEKDIEMNDVIYDCIDNYFHHNENILIEWFVCIKCLFLVDKNIIL
NYLIGKTEYIVKILHFITNCIGRKTKEELSIYIDVLLLLLNISEIRFMFTNYIDMYINIMKSLNYDQCFLKLLL
GTFKLYMHNIDFKQQIQDNVDLFFYAKEILKQFLLTYDNDADGKNNTNNDKREENEEQTSHLNYSNLNSYTCCV
KKCDDNDTKKKDIINQKKDEKNKKHCELVDKKKKDHTYIHSNMSCEKTLKDLIEMLFYLSLHIEFKKQLLEEKN
NYILFFLIKVGHDINKKKLDNTYKYIYCNTINNLILTKNDEKIKRREINKTNLSNFDNEQIEALEQFYDKLPKE
ARPKTDPLYDYGDEETSNKLIDLLLYNEKYQMNHINDKNKNNNNNNNINNGNVSPLSSKCSYTNGTIINIIYNF
INSNFFTTNIAESVCEIISKFVKNTNNIGIVLVNNGLKTLLLASKHITNKKNCALALSEIFIYTNPKLIHFYEA
YDSLPLLIEQLKSDEELLIFKTLMAITNILTIDENVAIKAMQLNLWYKCFDILSTENEYIKSASLECICNLCSQ
SHVHQYIYDKYQTIMKSKNESDKDILFVDIQIIYSFTMEYQNYKCVFAATGALGMLSSDLRLPYYLVRTKGIDH
IFSSFNNTTDQNILLRILTFFNNIMTCDDIPDDILKKIKTYVEKKKDLNEENTQMANFILQ.

SEQ ID NO: 5 *Plasmodium falciparum* 3D7 myosin A tail domain interacting
protein (MTIP) mRNA, complete cds, nucleotide sequence: XM_001350813.1
(referred to herein as Pf MTIP, *Plasmodium falciparum* MLC1,
or *Plasmodium falciparum* regulatory light chain)
atgaaacaagaatgcaatgtatgttattttaacttgcctgacccagagtccaccttaggtccatatgataatga
attaaattatttcacttggggaccaggatttgaatatgaacctgaaccacaaagaaagccattgtcaattgaag
aaagttttgaaaactctgaagaatccgaagaatcagttgctgacatacaacaacttgacgaaaaagtagatgaa
agtgatgtgaggattattttaatgaaaagagtagtggtgggaaaataagtatagacaatgcatcttacaatgc
tcgaaagttaggtttagctccatcaagtatcgatgaaaagaaattaaagaattatatggagataacttaacat
atgaacaatatttagaatatttgtctatatgtgtccatgataaagataatgtagaagaacttattaaaatgttt
gcacactttgataataattgtactggttacttaactaagagccaaatgaaaaatattcttacaacttggggtga
tgcattaacggatcaagaagccatagatgctcttaatgccttttcatcagaagataacattgattacaaattat
tctgtgaagatatattacaataa.

SEQ ID NO: 6 *Plasmodium falciparum* 3D7 myosin A tail domain interacting protein
(MTIP) amino acid sequence: XP_001350849.1 (also referred to herein as Pf MTIP,
*Plasmodium falciparum* MLC1, or *Plasmodium falciparum* regulatory light chain)
MKQECNVCYFNLPDPESTLGPYDNELNYFTWGPGFEYEPEPQRKPLSIEESFENSEESEESVADIQQLEEKVDE
SDVRIYFNEKSSGGKISIDNASYNARKLGLAPSSIDEKKIKELYGDNLTYEQYLEYLSICVHDKDNVEELIKMF
AHFDNNCTGYLTKSQMKNILTTWGDALTDQEAIDALNAFSSEDNIDYKLFCEDILQ .

SEQ ID NO: 7 *Plasmodium falciparum* 3D7 calmodulin, putative (PF14 0181) mRNA,
complete cds, nucleotide sequence: XM 001348318.1 (also referred to
herein as PfELC or *Plasmodium falciparum* essential light chain)
atgcgcatagtagataagcaaataaaagaatccttccttttagcagacagaaattttgatgggcatatttcatc
gaatgaattattatacgctttaagattccttggagtggaatctgattattctctaatggaaatgaaagtgggg
caacttattcaatgaatgattatgttaaaatagctaagaaacattaggtgcacacacaccaaaagaaagaatt
acaaattccttaaaaaaaatggataaaaataacaatggaactatatcagttgacgcattagttcatttagttat
gactatgagtgatattttaacagaaatgattacagaaaatttaaaaaatttgttgatcctgaaagcagaaata
tcataccgttacatgtatttgtagaaaaaatactttcgtaa.

SEQ ID NO: 8 *Plasmodium falciparum* 3D7 calmodulin, putative (PF14 0181),
amino acid sequence: XP_001348354.1 (also referred to herein as PfELC (also
referred to herein as PfELC or *Plasmodium falciparum* essential light chain)
MRIVDKQIKESFLLADRNFDGHISSNELLYALRFLGVESDYSLMENKSGATYSMNDYVKIAKKHLGAHTPKERI
TNSLKKMDKNNNGTISVDALVHLVMTMSDILTENDYRKFKKFVDPESRNIIPLHVFVEKILS .

SEQ ID NO: 9 *Plasmodium falciparum* 3D7 calmodulin, putative (PF14 0181) mRNA,
complete cds, nucleotide sequence: XM_001348318.1 (also referred to herein as
PfCalmodulin)
atgcgcatagtagataagcaaataaaagaatccttccttttagcagacagaaattttgatgggcatatttcatc
gaatgaattattatacgctttaagattccttgggagtggaatctgattattctctaatggaaatgaaagtgggg
caacttattcaatgaatgattatgttaaaatagctaagaaacattaggtgcacacacaccaaaagaaagaatt
acaaattccttaaaaaaaatggataaaaataacaatggaactatatcagttgacgcattagttcatttagttat
gactatgagtgatattttaacagaaatgattacagaaaatttaaaaaatttgttgatcctgaaagcagaaata
tcataccgttacatgtatttgtagaaaaaatactttcgtaa.

-continued

Partial Listing of Sequences

SEQ ID NO: 10 *Plasmodium falciparum* 3D7 calmodulin, puatative (PF13_0181)
amino acid sequence: XP_001348497 (also referred to herein as PfCalmodulin)
MADKLTEEQISEFKEAFSLEFDKDGDGTITTKELGTVMRSLGQNPTEAELQDMINEIDTDGNGTIDFPEFLTLMA
RKLKDTDTEEELIEAFRVFDRDGDGYISADELRHVMTNLGEKLTNEEVDEMIREADIDGDGQINYEEFVKMMIAK.

SEQ ID NO: 11 *Toxoplasma gondii* TPR AK Seq, TPR domain-containing protein, CDS,
length = 3486 nucleotide sequence (also referred to herein as TgUNC)
atggaggatttgtcaaacgctacgttagctcgcctccaggcgctgaaagaggaaggaaatgcggagtttaagcg
gggcaagttcgagtccgcgatcgaagcgtattcgcgatgcctggctgatgcctcagacactctggataaagaac
cagacgtcctgggaggcgcgtgtgcggccagcctctcttcctcgactctcaggtcgcagaacctcgcaaagaa
agccctgccattctgaagcgcgtggccgaactgaaggcgcaaatcctgtgcaatcgcgccctgtgctaccagcg
gacgaagcagttcgccggcgccgaggcggactgtacgcgcgccatcgctctccatccggcctacgtgaagagtt
actaccgacgcgcggttgcgctggacgcccagggaaggcgtaaagagtgtgtggaggatctgcagacgtgtctg
cgcctgcagcctggaaacaaggaggcgcaggagatgctcgcgggggttcgcgacaaggtgatgaaggaggagga
gacgcgcgtcgaagagcagctgcccgagaacctgctgactgccggcctcaacgacgtgctcacggcctcgaagc
gagtcgcctcccttcgccaactcggcgccttcgttcaggagcggaagctgccggcgtcagttccttcgagacggc
ggtctgcgacgcgttgccgttgccctgaagagccaaatggacagtgagctcgagggcaacgccagcctcaccg
gtcgctcgagtctcttccggagaccacggcctcggacccgtggcttctgaagagagcaaaagcagcgcagacg
ccgttctccccgtcagcgtcgaagcagcgtgctgggagttgctcttgtccgtcgtccagcagcaccaggcggac
gacgaagacgacgcaaacaaggctctgcagacctctgtgaggccgtgaacgcgccgcttcaggtcgacgcgcc
ggtcctcgagtgccgcaagctctctccggcctctggactcccaacgacttcctcgtgcgtctgcggcagctcc
tgcgtgcaggcgtcgcgcgctccgacggcctcgctgcgaccgccgcaacgaagaagctgggaaactgcggacc
tgcgtgcaggcgtcgcgcgctccgacggcctcgctgcgaccgccgcaacgaagaagctgggaaactgcggacc
gtctggcgcggcgaagcctgtgacaggctcctgcgcacgatgggctgcgtggtgcaggcggcgcagtt
cgacgaggacgcctccttcctcgaggcctgcgccgccggcctggagtgtatagactcccgagaggtccagccgg
cggctgtcgcggcgcttgtgggcgtcgcacgacgcgcggcgccgcctgggcggcagagttgcggccgtgcggctg
cggcatggactcgaaaagtgtctcgaggacgccttgcaggtcgtctcggacgcagaacacgaactcgcgggcga
agacgctcgctctcagctggccaccgcgtccaagaaaagcgacagcttgaagcggtgagtcgtctacagggcc
agaccgagtacttgatcatcacgctaatcgctcttctcgcagacaaagaccgcggcaaggaggagcctcccgac
atgagtcgcctggtcgaccagctgctgtcgccgtacttccggccgtgcgcagaccccgaggagagcgtcgtcac
cctgacagttgggttgaaggcgctgcgtttgattctgactgcggcgcgaagttgcgcgggcgtacctgattt
ccgcgtcttcgattctccccctacctcctggctgccgccgcgggcggtgtaggtacagcgcagagcggggccgcg
gggactgcagcgcatcggcgccagcaggaagctgcattggaggtcttgctggcctgcatggatttcccagaact
gcgtgcgacgttgctcgaggcgaacgcggtgccggtcttcgcgaaagtgtgcagcgagagcgcgaatgtcggt
gttggatgagggcgcgtctggcggctgcactcgctcggctgtctgttcacgacgaggacgtccggatccaggta
tttgactcgatcgacttctacgacgtcctcgatgtgctcgtgtcggaaattcgcgcggcaggtggcgacggccg
ccaggttgcggagccgagcaccgaagccaagaacgcgcagaaaggccagccgatggctgttggagagggacgt
ttcggtctctgcttgagatcttcttcttcctcagtctccacggcgacttcaaagcgcggctcgtgaccggaag
aagggcgcgagggtgctgcggacgcttctgcaagttgcgaacggggctgggaaaaaaggcgcttcttcgagtct
gacgcggtatctccttctccagagtctgtgcaacatcatgcggtcgcgagaagaccgacagagacagcggagaa
ggaaaggcgaggtcggaagtccactcgcagacgagcagctgacgacgagcagctgaggagttgttcaag
aagctgccggaaggcgcgaagccggctgcgaacggcgaggtcgatctcggagacaaggccctcgcaacgcagct
ccgcgacatgctcctagacctgaacgtggttcatgcaatcgccgtgaacgtctgcgcgacccgccgccgtctt
ccaacgtcctgtgtgccgcggcgcaggcgctgaagttcctttgcgaggactcgcggcaccgaggcagagctgtt
caggagggggcattcggacgctcttgacggcggcttgggcgcgagtggggctcgaggaattcccagacgaccagaggaacgc
gcgacaagctgcggcgcagctctgcatcaccaccaacccggccctgttctcttaccgcgagagcttagacctcg
tccctgcctcgcgccgcttcaaggaccgccacgagttgctgcagtacgaaggcgcgctcgcgttgacgaat
ctctgtgccctcagcgaggaggtccgcatgcgtgcgtggctcggcggcgtctgggaaggcttcgaggacctcat
gttcggggagaacgagttgctgcgcgccgcggggttggagggatggtgcaacttgtcggcctcgccgacggtcc
aaacggagatcgggaagaagatggaacgtttcgcggcggagaaacaagaagttcaagatatgaaactcttgctc
gcgttcacgcgggaaacgaacaaccctcgtgcgcagtccgccgccgtcgcggctctcgcgatgctttctcgcgaa
cgagaaggtcgcacgctgtcttccggcctacagcctctttggcaacctcgctttgagcctcgaggaagcgaagg
ccgagcaggaagctctgatcgtgaggtgcgtctccgccctctacaacgtctggatcgagttgagcagttctgag
gcgggagctgagacccgcatgcagatcgtgaaaacctgcagagaaaccaacaaaaactcactggagacgcaca
acacctcgccaaggaagtcctcacggcagaactctcccaagcaaacacacacgaaagaatccaccccagact
caagctaacggc.

SEQ ID NO: 12 TGGT1_249480, *Toxoplasma gondii* GT1, tetratricopeptide repeat-
containing protein, length = 1161, amino acid sequence, (also referred to
herein as TgUNC)
MEDLSNATLARLQALKEEGNAEFKRGKFESAIEAYSRCLADASDTLDKEPDVLGGACAASLSSSDSQVAEPRKE
SPAILKRVAELKAQILCNRALCYQRTKQFAAAEADCTRAIALHPAYVKSYYRRAVALDAQGRRKECVEDLQTCL
RLQPGNKEAQEMLAGVRDKVMKEEETRVEEQLPENLLTAGLNDVLTASKRVASLRQLGAFVQERKLRRQFLRDG
GLRRVAVALKSQMDSELEGNGQPHRSLESLPETTASDPVASEESKSSADAVLPVSVEAACWELLLSVVQQHQAD
DEDDANKALQTSVEAVNAPLQVDAPVLECRQALSGLWTPNDFLVRLRQLLRAGVARSDGLAATAANEEAGKLRT
VWRGEACDRLLRTMGCVVQLQAAQFDEDASFLEACAAGLECIDSREVQRAAVAALVGVADARRRLGGRVAAVRL
RHGLEKCLEDALQVVSDAEHELAGEDARSQLATASKKSDRLEAVSRLQGOTEYLIITLIALLADKDRGKEEPPD
MSRLVDQLLSPYFRPCADPEESVVTLTVGLKALRLILTAAREVARAYLISASSILPYLLAAAAGGVGTAQSGAA
GTAAHRRQQEAALEVLIACMDFPELRATLLEANAVPVFAKVCSESANVGCWMRARLAAALARLSVHDEDVRIQV
FDSIDFYDVLDVLVSEIRAAGGDGRQVAEPSTEAKNAQKGQPMAVGEETFRSLLEIFFFLSLHGDFKARLVTGK
KGARVLRTLLQVANGAGKKGASSSLTRYLLLQSLCNIMRSREDRQRQRRRKGEVGSPLADVDDEQLQQLEELFK
KLPEGAKPAANGEVDLGDKALATQLRDMLLDLNVVHAIAVNVCATPPPSSNVLCAAAQALKFLCEDSRHRGRAV
QEGGIRTLLVAASGLEEFPDDQRNARQAAAQLCITTNPALFSYRESLDLVPCLAPLLKDRHELLQYEGALALTN
LCALSEEVRMRAWLGGVWEGFEDLMFGENELLRAAGLEGWCNLSASPTVQTEIGKKMERFAAEKQEVQDMKLLL
AFTRETNNPRAQSAAVAALMLLANEKVARCLPAYSLFGNLALSLEEAKAEQEALIVRCVSALYNVWIELSSSE
AGAETRMQIVKTLQRNQQKLTGDAQHLAKEVLTAELSQANTHTKESTPDSS.

-continued

Partial Listing of Sequences

SEQ ID NO: 13 Truncated *Toxoplasma gondii* TgUNC nucleotide sequence, CDS:
atgggactcgcgggggttcgcgacaaggtgatgaaggaggaggagacgcgcgtcgaagagcagctgcccgagaa
cctgctgactgccggcctcaacgacgtgctcacggcctcgaagcgagtcgcctcccttcgccaactcggcgcct
tcgttcaggagcggaagctgcggcgtcagttccttcgagacggcggtctgcgacgcgttgccgttgccctgaag
agccaaatggacagtgagctcgagggcaacggccagcctcaccggtcgctcgagtctcttccggagaccacggc
ctcggaccccgtggcttctgaagagagcaaaagcagcgcagacgccgttctccccgtcagcgtcgaagcagcgt
gctgggagttgctcttgtccgtcgtccagcagcaccaggcggacgacgaagacgacgcaaacaaggctctgcag
acctctgtggaggccgtgaacgcgccgcttcaggtcgacgcgccggtcctcgagtgccgccaagctctctccgg
cctctggactcccaacgacttcctcgtgcgtctgcggcagctcctgcgtgcaggcgtcgcgcgctccgacggcc
tcgctgcgaccgccgcgaacgaagaagctgggaaactgcggaccgtctggcgcggcgaagcctgtgacaggctc
ctgcgcacgatgggctgcgtggtgcagctgcaggcggcgcagttcgacgaggacgcctccttcctcgaggcctg
cgccgccggcctggagtgtatagactcccgagaggtccagcgcgcggctgtcgcggcgcttgtgggcgtcgcag
acgcgcggcgccgcctgggcggcagagttgcggccgtgcggctgcggcatggactcgaaaagtgtctcgaggac
gccttgcaggtcgtctcggacgcagaacacgaactcgcgggcgaagacgctcgctctcagctggccaccgcgtc
caagaaaagcgacagacttgaagcggtgagtcgtctacagggccagaccgagtacttgatcatcacgctaatcg
ctcttctcgcagacaaagaccgcggcaaggaggagcctcccgacatgagtcgcctggtcgaccagctgctgtcg
ccgtacttccggccgtgcgcagaccccgaggagagcgtcgtcaccctgacagttgggttgaaggcgctgcgttt
gattctgactgcggcgcgcgaagttgcgcgggcgtacctgatttccgcgtcttcgattctcccctacctcctgg
ctgccgccgcgggcggtgtaggtacagcgcagagcggggccgcggggactgcagcgcatcggcgccagcaggaa
gctgcattggaggtcttgctggcctgcatggatttcccagaactgcgtgcgacgttgctcgaggcgaacgcggt
gccggtcttcgcgaaagtgtgcagcgagagcgcgaatgtcgggtgttggatgagggcgcgtctggcggctgcac
tcgctcggctgtctgttcacgacgaggacgtccggatccaggtatttgactcgatcgacttctacgacgtcctc
gatgtgctcgtgtcggaaattcgcgcggcaggtggcgacggccgccaggttgcggagccgagcaccgaagccaa
gaacgcgcagaaaggccagccgatggctgttggagaggagacgtttcggtctctgcttgagatcttcttcttcc
tcagtctccacggcgacttcaaagcgcggctcgtgaccgggaagaagggcgcgagggtgctgcggacgcttctg
caagttgcgaacggggctgggaaaaaaggcgcttcttcgagtctgacgcggtatctccttctccagagtctgtg
caacatcatgcggtcgcgagaagaccgacagagacagcggagaaggaaaggcgaggtcggaagtccactcgcag
acgttgacgacgagcagctgcagcagctcgaggagttgttcaagaagctgccggaaggcgcgaagccggctgcg
aacggcgaggtcgatctcggagacaaggccctcgcaacgcagctccgcgacatgctcctagacctgaacgtggt
tcatgcaatcgccgtgaacgtctgcgcgaccccgccgccgtcttccaacgtcctgtgtgccgcggcgcaggcgc
tgaagttcctttgcgaggactcgcggcaccgaggcagagctgttcaggagggggcattcggacgctcttggtg
gccgcgagtgggctcgaggaattcccagacgaccagaggaacgcgcgacaagctgcggcgcagctctgcatcac
caccaacccggccctgttctcttaccgcgagagcttagacctcgtcccctgcctcgcgccgcttctcaaggacc
gccacgagttgctgcagtacgaaggcgcgctcgcgttgacgaatctctgtgccctcagcgaggaggtccgcatg
cgtgcgtggctcggcggcgtctgggaaggcttcgaggacctcatgttcggggagaacgagttgctgcgcgccgc
ggggttggagggatggtgcaacttgtcggcctcgccgacggtccaaacggagatcgggaagaagatggaacgtt
tcgcggcggagaaacaagaagttcaagatatgaaactcttgctcgcgttcacgcgggaaacgaacaaccctcgt
gcgcagtccgccgccgtcgcggctctcgcgatgcttctcgcgaacgagaaggtcgcacgctgtcttccggccta
cagcctctttggcaacctcgctttgagcctcgaggaagcgaaggccgagcaggaagctctgatcgtgaggtgcg
tctccgccctctacaacgtctggatcgagttgagcagttctgaggcgggagctgagacccgcatgcagatcgtg
aaaaccctgcagagaaaccaacaaaaactcactggagacgcacaacacctcgccaaggaagtcctcacggcaga
actctcccaagcaaacacacacacgaaagaatccaccccagactcaagctaa.

SEQ ID NO: 14 Truncated *Toxoplasma gondii* TgUNC amino acid sequence:
MGLAGVRDKVMKEEETRVEEQLPENLLTAGLNDVLTASKRVASLRQLGAFVQERKLRRQFLRDGGLRRVAVALK
SQMDSELEGNGQPHRSLESLPETTASDPVASEESKSSADAVLPVSVEAACWELLLSVVQQHQADDEDDANKALQ
TSVEAVNAPLQVDAPVLECRQALSGLWTPNDFLVRLRQLLRAGVARSDGLAATAANEEAGKLRTVWRGEACDRL
LRTMGCVVQLQAAQFDEDASFLEACAAGLECIDSREVQRAAVAALVGVADARRRLGGRVAAVRLRHGLEKCLED
ALQVVSDAEHELAGEDARSQLATASKKSDRLEAVSRLQGQTEYLIITLIALLADKDRGKEEPPDMSRLVDQLLS
PYFRPCADPEESVVTLTVGLKALRLILTAAREVARAYLISASSILPYLLAAAAGGVGTAQSGAAGTAAHRRQQE
AALEVLLACMDFPELRATLLEANAVPVFAKVCSESANVGCWMRARLAAALARLSVHDEDVRIQVFDSIDFYDVL
DVLVSEIRAAGGDGRQVAEPSTEAKNAQKGQPMAVGEETFRSLLEIFFFLSLHGDFKARLVTGKKGARVLRTLL
QVANGAGKKGASSSLTRYLLLQSLCNIMRSREDRQRQRRRKGEVGSPLADVDDEQLQQLEELFKKLPEGAKPAA
NGEVDLGDKALATQLRDMLLDLNVVHAIAVNVCATPPPSSNVLCAAAQALKFLCEDSRHRGRAVQEGGIRTLLV
AASGLEEFPDDQRNARQAAAQLCITTNPALFSYRESLDLVPCLAPLLKDRHELLQYEGALALTNLCALSEEVRM
RAWLGGVWEGFEDLMFGENELLRAAGLEGWCNLSASPTVQTEIGKKMERFAAEKQEVQDMKLLLAFTRETNNPR
AQSAAVAALAMLLANEKVARCLPAYSLFGNLALSLEEAKAEQEALIVRCVSALYNVWIELSSSEAGAETRMQIV
KTLQRNQQKLTGDAQHLAKEVLTAELSQANTHTKESTPDSS.

SEQ ID NO: 15 TGGT1_235470 (toxodb.org), *Toxoplasma gondii* GT1, CDS DNA, myosin A, TgMyoA heavy chain
ATGGCGAGCAAGACCACGTCTGAGGAGCTGAAAACGGCCACGGCGCTGAAGAAGAGGTCGTCCGATGTCCACGC
GGTCGACCACTCCGGCAATGTGTACAAAGGATTTCAAATCTGGACGGACTTGGCGCCGTCGGTGAAGGAGGAGC
CGGACCTGATGTTTGCCAAGTGCATCGTGCAGGCGGGGACAGACAAGGGGAACTTGACCTGCGTCCAGATCGAT
CCACCGGGCTTCGACGAACCGTTCGAAGTCCCGCAGGCGAATGCGTGGAACGTAAACAGCCTGATCGACCCCAT
GACGTACGGAGACATCGGCATGTTGCCTCACACGAACATTCCTTGCGTCCTCGACTTCCTCAAGGTGCGCTTCA
TGAAGAATCAAATCTACACGACTGCGGACCCGCTCGTCGTCGCCATCAATCCCTTCCGCGACCTCGGGAACACC
ACGCTCGACTGGATTGTTCGATACAGAGACACTTTCGACCTCTCCAAACTCGCGCCCCATGTTTTCTACACCGC
CCGACGCGCGCTCGACAACCTCCACGCCGTCAACAAGTCGCAAACGATCATCGTGTCCGGTGAGTCTGGCGCGG
GCAAGACGGAGGCGACGAAGCAGATTATGAGGTATTTTGCGGCGGCGAAGACGGGGTCGATGGATTTGCGGATT
CAGAACGCGATCATGGCGGCGAATCCAGTGCTTGAGGCATTTGGAAATGCGAAGACGATTCGCAACAACAACTC
GTCGCGTTTCGGACGCTTCATGCAGCTGGATGTGGGTCGCGAAGGAGGCATCAAGTTTGGCTCCGTCGTCGCCT
TTCTCCTGGAAAAGTCGCGTGTTCTCACGCAGGACGAACAGGAGCGGTCGTACCACATCTTCTACCAAATGTGC
AAGGGGGCGGACGCGGCGATGAAGGAGCGCTTCCATATCCTGCCGCTCTCGGAGTACAAGTACATCAATCCGTT
GTGCCTGGACGCGCCAGGGATCGACGACGTCGCGGAGTTCCACGAAGTCTGCGAGTCGTTCCGGTCGATGAATC
TGACGGAGGACGAAGTCGCGAGCGTGTGGAGCATCGTGAGTGGAGTGCTGCTGCTTGGCAACGTCGAGGTGACA
GCGACGAAGGATGGGGGATCGACGACGCCGCGGCGATCGAGGGGAAGAACTTGGAGGTTTTCAAAAAGGCCTG

Partial Listing of Sequences

```
CGGGCTGCTCTTCCTCGACGCGGAGCGCATTCGCGAAGAGCTGACGGTGAAGGTTTCGTATGCGGGGAATCAGG
AGATCCGCGGCCGGTGGAAGCAGGAAGACGGAGACATGCTCAAGTCGTCGCTCGCGAAGGCGATGTACGACAAG
TTGTTCATGTGGATCATTGCCGTGTTGAACCGCAGCATCAAGCCTCCGGGCGGCTTCAAGATCTTCATGGGCAT
GCTCGACATCTTCGGCTTCGAAGTCTTCAAGAACAACTCGCTGGAGCAGTTCTTCATCAACATCACGAACGAAA
TGCTGCAGAAGAACTTCGTCGACATCGTCTTCGACCGCGAGAGCAAGCTGTATCGTGACGAGGGTGTCTCCTCC
AAGGAGTTGATTTTCACCTCGAACGCAGAAGTGATCAAGATCTTGACGGCGAAGAACAACTCGGTGCTCGCTGC
GCTCGAGGACCAGTGCCTCGCCCCTGGAGGCAGCGACGAAAAGTTCCTCTCGACCTGCAAGAACGCGCTGAAAG
GAACCACCAAGTTCAAGCCTGCGAAGGTCTCTCCGAACATCAATTTCCTCATCTCGCACACTGTCGGCGACATC
CAGTACAACGCCGAAGGCTTCCTCTTCAAAAACAAAGATGTCCTGCGAGCAGAAATCATGGAAATCGTGCAGCA
AAGCAAGAACCCCGTCGTCGCGCAACTCTTCGCTGGCATCGTCATGGAGAAGGGGAAGATGGCCAAGGGACAAC
TGATTGGGTCGCAGTTCCTCTCGCAGCTGCAGAGCCTCATGGAACTTATCAACAGCACCGAGCCTCACTTCATT
CGCTGCATCAAGCCGAACGACACGAAGAAGCCCTCGACTGGGTGCCGTCGAAAATGCTCATTCAGCTGCACGC
GCTCTCCGTCCTCGAGGCTCTTCAGCTCCGTCAACTCGGCTACTCTTACAGACGTCCGTTCAAGGAGTTCCTCT
TCCAGTTCAAGTTTATCGACCTCTCGGCTTCTGAAAATCCAAATCTGGACCCCAAAGAAGCTGCGCTGAGACTC
CTCAAAAGCAGCAAACTGCCCAGCGAAGAATACCAGCTCGGGAAGACAATGGTTTTCCTCAAGCAGACGGGCGC
GAAAGAACTGACGCAGATTCAGAGAGAATGCCTTTCTTCTTGGGAGCCTCTCGTCTCAGTGCTCGAGGCGTACT
ACGCTGGCAGACGCCACAAGAAGCAGCTGCTGAAAAAGACCCCCTTCATCATTCGCGCCCAGGCTCACATCCGC
AGACACCTGGTGGACAACAACGTCAGCCCCGCGACTGTTCAGCCGGCGTTCTAG.
```

SEQ ID NO: 16 TGGT1_235470 (toxodb.org), *Toxoplasma gondii* GT1, amino acid sequence, myosin A, TgMyoA heavy chain
MASKTTSEELKTATALKKRSSDVHAVDHSGNVYKGFQIWTDLAPSVKEEPDLMFAKCIVQAGTDKGNLTCVQID
PPGFDEPFEVPQANAWNVNSLIDPMTYGDIGMLPHTNIPCVLDFLKVRFMKNQIYTTADPLVVAINPFRDLGNT
TLDWIVRYRDTFDLSKLAPHVFYTARRALDNLHAVNKSQTIIVSGESGAGKTEATKQIMRYFAAAKTGSMDLRI
QNAIMAANPVLEAFGNAKTIRNNNSSRFGRFMQLDVGREGGIKFGSVVAFLLEKSRVLTQDEQERSYHIFYQMC
KGADAAMKERFHILPLSEYKYINPLCLDAPGIDDVAEFHEVCESFRSMNLTEDEVASVWSIVSGVLLLGNVEVT
ATKDGGIDDAAAIEGKNLEVFKKACGLLFLDAERIREELTVKVSYAGNQEIRGRWKQEDGDMLKSSLAKAMYDK
LFMWIIAVLNRSIKPPGGFKIFMGMLDIFGFEVFKNNSLEQFFINITNEMLQKNFVDIVFDRESKLYRDEGVSS
KELIFTSNAEVIKILTAKNNSVLAALEDQCLAPGGSDEKFLSTCKNALKGTTKFKPAKVSPNINFLISHTVGDI
QYNAEGFLFKNKDVLRAEIMEIVQQSKNPVVAQLFAGIVMEKGKMAKGQLIGSQFLSQLQSLMELINSTEPHFI
RCIKPNDTKKPLDWVPSKMLIQLHALSVLEALQLRQLGYSYRRPFKEFLFQFKFIDLSASENPNLDPKEAALRL
LKSSKLPSEEYQLGKTMVFLKQTGAKELTQIQRECLSSWEPLVSVLEAYYAGRRHKKQLLKKTPFIIRAQAHIR
RHLVDNNVSPATVQPAF.

SEQ ID NO: 17 TgMLC1 (ToxoDB TgGT1_257680, toxodb.org) CDS DNA, myosin light chain MLC1
```
atgagcaaggtcgagaagaaatgcccggtgtgctaccagaagctgccgaacccggcagatgttctgggtccgat
ggacaaggagttgaactatttcatgtggatgccaggcttcgagtggcgcccggaaccgaaggtgggggagtacg
atggtgcctgtgagtcgccctcttgccgcgagggggggcgccctgcggcagacgaagacatgcaggaggctctc
gaggagatggtggaggccgacgaaatgtatgcgcgcttcaacgcgagagcttccggaggaaaggtatccacggg
agacgccatgattctcgcgcgccagctcggacttgccccgtcctacgcagacaaacaggcctttgaggaaaaga
gcggcgacaaccttgactacgccagcttccagaaattcgttggcaccagcaccccaccccgaagacaacatcgag
gacctcgtcgaagccttcgcatactttgacgtctctaagcacggttacctgacgcgcaagcagatggggaacat
cctcatgacctacggagagcctctcaccagaagagtttaatgccttggctgcggagtacttcacaagtgacc
agatcgactacaggcaattctgcaaggcaatgctcgagcgaagggagtaa.
```

SEQ ID NO: 18 TgMLC1 (ToxoDB TgGT1_257680, toxodb.org) amino acid sequence, myosin light chain MLC1
MSKVEKKCPVCYQKLPNPADVLGPMDKELNYFMWMPGFEWRPEPKVGEYDGACESPSCREGGRPAADEDMQEAL
EEMVEADEMYARFNARASGGKVSTGDAMILARQLGLAPSYADKQAFEEKSGDNLDYASFQKFVGTSTHPEDNIE
DLVEAFAYFDVSKHGYLTRKQMGNILMTYGEPLTTEEFNALAAEYFTSDQIDYRQFCKAMLERRE.

SEQ ID NO: 19 TGGT1_269442, *Toxoplasma gondii* gt1, putative calmodulin, cds, length = 264
```
atgtcaatggcgtggcctgattttgaggcgtggatgtcgaagaaactggcgtcctacaaccctgaggaggagtt
gatcaaatcttttcaaggcttttgaccggtcgaacgacggcaccgtgtctgcggacgagctttctcaagttatgc
tcgctctcggcgagttgcttccgacgaagaagtcaaggccatgatcaaggaagccgacccgaacggcactggc
aagatccagtacgccaactttgtcaagatgctgctgaaataa.
```

SEQ ID NO: 20: TGGT1_269442, *Toxoplasma gondii* gt1, putative calmodulin, amino acid sequence
MSMAWPDFEAWMSKKLASYNPEEELIKSFKAFDRSNDGTVSADELSQVMLALGELLSDEEVKAMIKEADPNGTG
KIQYANFVKMLLK.

SEQ ID NO: 21 A biotin acceptor site amino acid sequence
SMEAPAAAEISGHIVRSPMVGTFYRTPSPDAKAFIEVGQKVNVGDTLCIVEAMKMMNQIEADKSGTVKAILVES
GQPVEFDEPLVVIERS.

SEQ ID NO: 22 A Myc tag amino acid sequence
EQKLISEEDL.

SEQ ID NO: 23 A Ty1 tag amino acid sequence
EVHTNQDPLD.

-continued

Partial Listing of Sequences

SEQ ID NO: 24
*Plasmodium falciparum* motor domain amino acid sequence; PfMyoA heavy chain ending at Lys 773
MAVTNEEIKTASKIVRRVSNVEAFDKSGSVFKGYQIWTDISPTIENDPNIMFVKCVVQQGSKKEKLTVVQIDPP
GTGTPYDIDPTHAWNCNSQVDPMSFGDIGLLNHTNIPCVLDFLKHRYLKNQIYTTAVPLIVAINPYKDLGNTTN
EWIRRYRDTADHTKLPPHVFTCAREALSNLHGVNKSQTIIVSGESGAGKTEATKQIMRYFASSKSGNMDLRIQT
AIMAANPVLEAFGNAKTIRNNNSSREGREMQLVISHEGGIRYGSVVAFLLEKSRIITQDDNERSYHIFYQFLKG
ANSTMKSKFGLKGVTEYKLLNPNSTEVSGVDDVKDFEEVIESLKNMELSESDIEVIFSIVAGILTLGNVRLIEK
QEAGLSDAAAIMDEDMGVFNKACELMYLDPELIKREILIKVTVAGGTKIEGRWNKNDAEVLKSSLCKAMYEKLF
LWIIRHLNSRIEPEGGEKTFMGMLDIFGFEVEKNNSLEQLFINITNEMLQKNFVDIVFERESKLYKDEGISTAE
LKYTSNKEVINVLCEKGKSVLSYLEDQCLAPGGTDEKFVSSCATNLKENNKFTPAKVASNKNFIIQHTIGPIQY
CAESFLLKNKDVLRGDLVEVIKDSPNPIVQQLFEGQVIEKGKIAKGSLIGSQFLNQLTSLMNLINSTEPHFIRC
IKPNENKKPLEWCEPKILIQLHALSILEALVLRQLGYSYRRTFEEFLYQYKFVDIAAAEDSSVENQNKCVNILK
LSGLSESMYKIGKSMVFLKQEGAKILTKIQREK.

SEQ ID NO: 25
*Toxoplasma gondii* motor domain amino acid sequence; TgMyoA heavy chain ending at Cys 775
MASKTTSEELKTATALKKRSSDVHAVDHSGNVYKGFQIWTDLAPSVKEEPDLMFAKCIVQAGTDKGNLTCVQID
PPGFDEPFEVPQANAWNVNSLIDPMTYGDIGMLPHTNIPCVLDFLKVRFMKNQIYTTADPLVVAINPFRDLGNT
TLDWIVRYRDTFDLSKLAPHVEYTARRALDNLHAVNKSQTIIVSGESGAGKTEATKQIMRYFAAAKTGSMDLRI
QNAIMAANPVLEAFGNAKTIRNNNSSREGREMQLDVGREGGIKEGSVVAELLEKSRVLTQDEQERSYHIFYQMC
KGADAAMKERFHILPLSEYKYINPLCLDAPGIDDVAEFHEVCESFRSMNLTEDEVASVWSIVSGVLLLGNVEVT
ATKDGGIDDAAAIEGKNLEVEKKACGLLELDAERIREELTVKVSYAGNQEIRGRWKQEDGDMLKSSLAKAMYDK
LFMWIIAVLNRSIKPPGGFKIFMGMLDIFGFEVEKNNSLEQFFINITNEMLQKNEVDIVEDRESKLYRDEGVSS
KELIFTSNAEVIKILTAKNNSVLAALEDQCLAPGGSDEKFLSTCKNALKGTTKFKPAKVSPNINFLISHTVGDI
QYNAEGFLEKNKDVLRAEIMEIVQQSKNPVVAQLFAGIVMEKGKMAKGQLIGSQFLSQLQSLMELINSTEPHFI
RCIKPNDTKKPLDWVPSKMLIQLHALSVLEALQLRQLGYSYRRPFKEFLFQFKFIDLSASENPNLDPKEAALRL
LKSSKLPSEEYQLGKTMVFLKQTGAKELTQIQREC.

SEQ ID NO: 26
*Plasmodium falciparum* motor domain including the ELC binding site, amino acid sequence, PfMyoA heavy chain ending at Asn798
MAVTNEEIKTASKIVRRVSNVEAFDKSGSVFKGYQIWTDISPTIENDPNIMFVKCVVQQGSKKEKLTVVQIDPP
GTGTPYDIDPTHAWNCNSQVDPMSFGDIGLLNHTNIPCVLDFLKHRYLKNQIYTTAVPLIVAINPYKDLGNTTN
EWIRRYRDTADHTKLPPHVFTCAREALSNLHGVNKSQTIIVSGESGAGKTEATKQIMRYFASSKSGNMDLRIQT
AIMAANPVLEAFGNAKTIRNNNSSREGREMQLVISHEGGIRYGSVVAFLLEKSRIITQDDNERSYHIFYQFLKG
ANSTMKSKFGLKGVTEYKLLNPNSTEVSGVDDVKDFEEVIESLKNMELSESDIEVIFSIVAGILTLGNVRLIEK
QEAGLSDAAAIMDEDMGVFNKACELMYLDPELIKREILIKVTVAGGTKIEGRWNKNDAEVLKSSLCKAMYEKLF
LWIIRHLNSRIEPEGGEKTFMGMLDIFGFEVEKNNSLEQLFINITNEMLQKNFVDIVFERESKLYKDEGISTAE
LKYTSNKEVINVLCEKGKSVLSYLEDQCLAPGGTDEKFVSSCATNLKENNKFTPAKVASNKNFIIQHTIGPIQY
CAESFLLKNKDVLRGDLVEVIKDSPNPIVQQLFEGQVIEKGKIAKGSLIGSQFLNQLTSLMNLINSTEPHFIRC
IKPNENKKPLEWCEPKILIQLHALSILEALVLRQLGYSYRRTFEEFLYQYKFVDIAAAEDSSVENQNKCVNILK
LSGLSESMYKIGKSMVFLKQEGAKILTKIQREKLVEWENCVSVIEAAILKHKYKQKVN.

SEQ ID NO: 27
*Toxoplasma gondii* motor domain including the ELC binding site, amino acid sequence, TgMyoA heavy chain ending at Leu 800
MASKTTSEELKTATALKKRSSDVHAVDHSGNVYKGFQIWTDLAPSVKEEPDLMFAKCIVQAGTDKGNLTCVQID
PPGFDEPFEVPQANAWNVNSLIDPMTYGDIGMLPHTNIPCVLDFLKVRFMKNQIYTTADPLVVAINPFRDLGNT
TLDWIVRYRDTFDLSKLAPHVFYTARRALDNLHAVNKSQTIIVSGESGAGKTEATKQIMRYFAAAKTGSMDLRI
QNAIMAANPVLEAFGNAKTIRNNNSSRFGRFMQLDVGREGGIKFGSVVAFLLEKSRVLTQDEQERSYHIFYQMC
KGADAAMKERFHILPLSEYKYINPLCLDAPGIDDVAEFHEVCESFRSMNLTEDEVASVWSIVSGVLLLGNVEVT
ATKDGGIDDAAAIEGKNLEVFKKACGLLFLDAERIREELTVKVSYAGNQEIRGRWKQEDGDMLKSSLAKAMYDK
LFMWIIAVLNRSIKPPGGFKIFMGMLDIFGFEVFKNNSLEQFFINITNEMLQKNFVDIVFDRESKLYRDEGVSS
KELIFTSNAEVIKILTAKNNSVLAALEDQCLAPGGSDEKFLSTCKNALKGTTKFKPAKVSPNINFLISHTVGDI
QYNAEGFLFKNKDVLRAEIMEIVQQSKNPVVAQLFAGIVMEKGKMAKGQLIGSQFLSQLQSLMELINSTEPHFI
RCIKPNDTKKPLDWVPSKMLIQLHALSVLEALQLRQLGYSYRRPFKEFLFQFKFIDLSASENPNLDPKEAALRL
LKSSKLPSEEYQLGKTMVFLKQTGAKELTQIQRECLSSWEPLVSVLEAYYAGRRHKKQLL.

SEQ ID NO: 28
*C. elegans* Unc45b amino acid sequence (Genbank Accession No. AAD01976.1)
mvarvqtaee irdegnaavk dqdyikadel ytealqlttd edkalrpvly rnramarlkr
ddfegaqsdc tkalefdgad vkalfrrsla reqlgnvgpa fqdakealrl spndkgivev
lqrlvkannd kikqttslan kvtdmeklaf rgeakdteqk mtalnnllvl cresesgatq
vwnqgalvpf vinlindase neevtvtair ildetiknsv rcmkflamhd pdgpksvrfv
crlmckkstk dfvdatgilv qrvfnamakm drqkemkpdp evaeankiwi irvllelqem
lqdpkvgavq retcidlflk nlmhmdggip rgwswkfvee rgllalldva sqipelceyp
vsaetrqhva iclqrleedm vfdtkrtifk ekvdmffnal isrctnddeg hkyriklscf
litmlqgpvd iginlitndq ltpimlemaa sqdhlmqgia aelivatvsk herainmlkv
gipvlralyd sedptvkvra lvglckigaa ggddiskatm keeavislak tckkfllete
kysvdirrya ceglsylsld advkewivdd slllkalvll akkagalcvy tlatiyanls
nafekpkvde emvklaqfak hhvpethpkd teeyvekrvr alveegavpa cvaysktesk
naleliarsl lafaeyedlr griiaeggtv lclrltkeas gegkikagha iaklgakadp
misfpgqray evvkplcdll hpdvegkany dslltltnla sysdsirgri lkekaipkie
efwfmtdheh lraaaaelll nllffekfye etvapgtdrl klwvlysaev eeerlsrasa
agfailtede nacarimdei kswpevfkdi amhedaetqr rglmgianim hssnklcsei vssevfrvlv avtklgtinq eragsteqak rgleaaekfg likatdreiy erenqmstiq
e.

SEQ ID NO: 29
*Podospora anserina* CRO1 amino acid sequence (Genbank Accession No. CAA76144.1)
matvaeaaaa apeplgrldq tllifaglme ggkedeetvr elgeltrlln ddvevtkkge
tsvttvidsd cvdtilcyld mrqpdvvrah aalctsaylk aagedggkkl aeffhdrvrr
gtyddyivaf cvaatifpiv pdltselfls egflaslgpl mrrkwksrkv etaclemina
acmnsacrea vqkyctewle eiveqdpdda vksmhtvdpd mhlqegsism rrhslqvqnl
aavvlaklra vpstaatagp eariqpatts iedlskrftr mlldedeieh vqpsieglay
aslqpkvkes lskdsktlkr lvkaldeapp rspmiygals iftnitryrp ietdeekrir
qlkayanaag klqqvdpine dehvterckr vfeagltpvl ikqsksgsaa slaliisiih
alstppplrg qlaqqgavrl liaawtalpe tengpkraaa qalarilist npalvfggtr
pipqsaairp lasiltpdpt adrrdllptf eslmaltnla stdddtrksi irtawddvee
qlfnpnsrvc taavelvcnl vqdpeqtlal fgdgspkakn rvkvivalad aedpktrsaa
ggalasltgf devvravmgl ergvevvlgl crderedlrh rgavvvrnmv fsegevgrla
rgklveggav ealmecakgs krrevvevvv qaaeglmgeg gk.

SEQ ID NO: 30
*S. cerevisiae* She4p amino acid sequence (Genbank Accession No. DAA10818.1)
mplcekgndp idsstidslc aafdktlkst pdvqkyndai ntifqlrqks esgkmpadlt
nsealkdrqk ieeiltrsyq dhsesrvhls kliqndipfa lnlfeilsrs sihvfvgcfs
nkdatialln elqirihyge dthvtyllsi ilqllnkfky nfkevrflvk elilrisede
vksmmliifa elqssfqkdf dkavvdfmss liveaeidvg ndplsiivkt lselypsltt
lcseifltkg lsklfkkrvf eeqdlqftke llrllssaci detmrtyite nylqllersl
nvedvqiysa lvlvktwsft kltcinlkql seifinaisr rimpkienvn esavkleevp
kvemsveala ylslkasvki mirsnesfte illtmiksqk mthclygllv imanlstlpe
esngssqsin dlknyadlkg pgadkvgaek eskedillfn ekyilrteli sflkremhnl
spnckqqvvr viynitrskn fipqcisqgg ttiileylan kqdigepiri lgcraltrml
iftnpglifk kysalnaipf lfellprstp vddnplhnde qikltdnyea llaltnlass
etsdgeevck hivstkvyws tienlmlden vplqrstlel isnmmshplt iaakffnlen
pqslrnfnil vkllqlsdve sqravaaifa niattiplia kelltkkeli enaiqvfadq
iddielrqrl lmlffglfev ipdngtnevy pllqenqklk dalnmslkrg dsgpefsaai
pvilakikv.

SEQ ID NO: 31
*Drosophila melanogaster* UNC-45 amino acid sequence (DmUNC) (Genbank
Accession No. AAK93568)
mtntinseev sdagsykdkg neafkasrwe eavehygkai kagskhkela vfyknraaay
lklgkyenav edcteslkaa pgdpkalfrr aqayealekf eeaykdatal fkadpgnktv
qpmlqrlhvv veersarnak tstkvkqmmd ltfdlatpid krraaannlv vlakeqtgae
llykdhciak vasltkvekd qdiyvnmvhl vaalcensve rtkgvltelg vpwfmrvldq
khencvstaq fclqtilnal sglknkpdsk pdkelctrnn reidtlltcl vysitdrtis
gaardgviel itrnvhytal ewaerlveir glcrlldvcs eledykyesa mditgsssti
asvclariye nmyydeakar ftdqideyik dkllapdmes kvrvtvaita llngpldvgn
qvvaregilq milamattdd elqqrvacec liaasskkdk akalceqqvd ilkrlyhskn
dgirvralvg lcklgsyggq daairpfgdg aalklaeacr rflikpgkdk dirrwaadgl
ayltldaeck ekliedkasi halmdlargg nqsclygvvt tfvnlcnaye kqemlpemie
lakfakqhip eeheldvdf inkritvlan egittalcal akteshnsqe liarvinavc
glkelrgkvv qeggvkallr malegtekgk rhatqalari gitinpevsf sgqrsldvir
pllnllqqdc talenfeslm altnlasmne svrqriikeq gvskieyylm edhlyltraa
aqclonlvms edvikmfegn ndrvkflall cededeetat acagalaiit sysvkcceki
laiaswldil htlianpspa vqhrgiviil nminageeia kklfetdime llsglgqlpd
dtrakareva tqclaaaery riiersdnae ipdvfaensk iseiidd.

SEQ ID NO: 42
Truncated PfLINC lacking N-terminal TPR domain (Genbank Accession No.
XP_001348369.1 beginning at N178)
NKDNNNKSEINRINEKLRDIMKIIDQNKNDPYKNISNIKKYLLDENTNNINDIEENNKKIKLLHSIYNQKFYIL
LKENIFLFLFDFIKKNNDISNYDDCNNNNNNNLYSHNINSLLLEKTAIYVIYKILSKLDNEHIIIENSKDDNY
NKNRNICINKLDNSKLQYYYDLDYIKMILSFNEYFTKDWIYIKKKINILENLKFSKDETLYKEHVDILIYII
NIMKYVYVINNDYILNIINSYYLNSDNSNINNSGINALTFLCKKKQLFTQNSKDNRKKKNDLLEMLKKENYLNI
QNNIQNNNNNNNYYFYKNEFIEFHFSDSHKYPLCINSEIKKIIQNVIGMYEHFSSSIEYTLILIFTLLHDPQRP
KEKDIEMNDVIYDCIDNYFHHNENILIEWFVCIKCLFLVDKNIILNYLIGKTEYIVKILHFITNCIGRKTKEEL
SIYIDVLLLLLNISEIRFMFTNYIDMYINIMKSLNYDQCFLKLLLGTFKLYMHNIDFKQQIQDNVDLFFYAKEI
LKQFLLTYDNDADGKNNTNNDKREENEEQTSHLNYSNLNSYTCCVKKCDDNDTKKKDIINQKKDEKNKKHCELV
DKKKKDHTYIHSNMSCEKTLKDLIEMLFYLSLHIEFKKQLLEEKNNYILFFLIKVGHDINKKKLDNTYKYIYCN
TINNLILTKNDEKIKRREINKTNLSNFDNEQIEALEQFYDKLPKEARPKTDPLYDYGDEETSNKLIDLLLYNEK
YQMNHINDKNKNNNNNNINNGNVSPLSSKCSYTNGTIINIIYNFINSNFFTTNIAESVCEIISKFVKNTNNIG
IVLVNNGLKTLLLASKHITNKKNCALALSEIFIYTNPKLIHFYEAYDSLPLLIEQLKSDEELLIFKTLMAITNI
LTIDENVAIKAMQLNLWYKCFDILSTENEYIKSASLECICNLCSQSHVHQYIYDKYQTIMKSKNESDKDILFVD
IQIIYSFTMEYQNYKCVFAATGALGMLSSDLRLPYYLVRTKGIDHIFSSFNNTTDQNILLRILTFFNNIMTCDD
IPDDILKKIKTYVEKKKDLNEENTQMANFILQ.

Partial Listing of Sequences

SEQ ID NO: 43
PfGAP 45 *Plasmodium falciparum* GAP45 Sequence, CDS, Genbank Accession No. XM_001350588.1
atgggaaataaatgttcaagaagcaaagtaaaggaacccaaacgtaaagatattgatgaattagctgaac
gtgaaaatttaaaaaaacaatctgaagaaataattgaagaaaaaccagaagaagttgttgagcaagtaga
agaaacacatgaagaacctcttgaacaagaacaggaactggatgaacagaaaatagaagaagaagaagaa
gaacctgaacaagtaccaaaagaagaaatagattatgcaactcaagaaaataaatcatttgaagaaaaac
atttagaagatttagaaagatctaattcagatattttattcagaatctcaaaaatttgataatgctagtga
taaattagaaacaggaactcaattaaccttatctactgaagccactggtgccgtacaacaaataactaaa
ttaagtgaacccgcccatgaagaaagtatatattttacttatagatctgtaaccaccttgtgatatgaata
aactcgatgaaaccgctaaagttttttcaagaagatgtggatgtgatcttggtgaacgtcatgatgaaaa
tgcatgtaaaatttgtagaaaaattgatttatccgatacacctttattgagctaa.

SEQ ID NO: 44
PfGAP 45 *Plasmodium falciparum* GAP45 amino acid sequence; Genbank Accession No. XP_001350624.1
MGNKCSRSKVKEPKRKDIDELAERENLKKQSEEIIEEKPEEVVEQVEETHEEPLEQEQELDEQKIEEEEE
EPEQVPKEEIDYATQENKSFEEKHLEDLERSNSDIYSESQKFDNASDKLETGTQLTLSTEATGAVQQITK
LSEPAHEESIYFTYRSVTPCDMNKLDETAKVFSRRCGCDLGERHDENACKICRKIDLSDTPLLS.

SEQ ID NO: 45
TgGAP 45 *Toxoplasma gondii* GAP45 Sequence, CDS, Genbank Accession No. XM_002366039.1
gtgagatttcctttcagcgaattttgtgatctcaagagcgagaggcacaactgtatttgagaactttttgc
tttttcagcgttgcacgagttttaaatctcggtgtgactgttcgaaaccctgtcatttccctccgagaag
atcggtcgacggcgcgcggacaaccgcgtgcgtaaaaggtgtttgctatttcgccggggagaaaagcggc
cgtaaagtcggaagacttgccagacgagacgagaaactgggtgcggcacggcatttcatcattctgtatg
tgttgttttccattcgaagaaagttttgtttctcgcggcagagggaaaggcgcgcaccgaacctgcccgc
agtttccggtacatccacgcacacacttcggtggctgaaacgccgcgattgttccgttcttgtgttcgcg
acttcgactctctgaatcgctcccccacacatcttttgttgtcgcccctcaactttttcgcacttttttc
gattcgaaatgggaaacgcgtgcaagaagaacacggccaagacgccgacccggaaggaggcggaggacct
ggctgagaaggagcggcaggagcgggaggcgaaggagaaggctgaggctgaagagaaggctcgcgccgaa
gcggagaagaacgcagcagacaaagcggaggctgaacgtagagcggcagaggcgcgagagcgcgaagaat
cagccaggaaggaggcggaggctgaggcggcccgcaaggccgaagcagaggcggctgaggccgagcgcct
ccggaaggaagcagagaagaaaaaggcggaggaggcgaaacgcaaggcggaggaggagcagcgcgccgca
gccgaggaagccggagcaaagagccgggaggaggccgagcgccgcaaagctgaagctgcggcggcagcgg
agcgcgagcgccagatgcaggaggcgctgaagcaagaggaaatgtcaccgagagagaagtacgacaagtt
agccagccccgaagactccgcatccgagaccacgatggcgacacagccgcagaaagtcgccgagcacagc
agcgcggcggtcacagacagatcagtggtggggtacaccgtgactccatgcgacatggcatcaattgacg
agacagctaagtacttgtcaaagcgctgcggttgcgacctaggcgaccaacacgacgaaaacgagtgccc
tatttgccgccacatcgacttgtcggatgcacccttgttgaactggtcgtaactgtttctgtgtttttt
ctactctacggccccggcttcgggatctgtgtctgtatagcgtgcgcttataaacgcgtaaacttcgtgt
ttaagaaagattagcaagggttaggacggtgaagaagagtttgggaccgtgtttttttcgacaaacgtcgg
gttgctagtatcgcacgtaggtgtgcactaccccgctctccatgtaggcgtagtctgtgtagcaacagga
cggttggcggcaaacagaaagggaggaaatttctgcgggttcttcgagtctgagctgtcgcgaaaagctc
caaaagcgaactggctcccgcagtctatgggggacgcacccgccgtagggtgaagtggctcacaggc
ttcgcccgcctgtccgtacgtgcagggcagaatcctgcccgaacgtgagaacaaccgtcattcccgtcg
tcacatagttcttttctcgaccatccccacgtgacaccactggtgtgcgaatgcggcgcagcgttcgac
tgtcttccgcgaaaggcgatgcttacaaacgcacgctcgcatgacatacgtgccgtaaagaggaaaccct
tet.

SEQ ID NO: 46
TgGAP 45 *Toxoplasma gondii* GAP45 amino acid sequence, Genbank Accession No. XP_002366080.1
MGNACKKNTAKTPTRKEAEDLAEKERQEREAKEKAEAEEKARAEAEKNAADKAEAERRAAEAREREESARKEAE
AEAARKAEAEAAEAERLRKEAEKKKAEEAKRKAEEEQRAAAEEAEQRAREEAERRKAEAAAAAERERQMQEALK
QEEMSPREKYDKLASPEDSASETTMATQPQKVAEHSSAAVTDRSVVGYTVTPCDMASIDETAKYLSKRCGCDLG
DQHDENECPICRHIDLSDAPLLN.

SEQ ID NO: 47
*Toxoplasma gondii* ELC1 nucleotide sequence, also referred to herein as TgELC1 nucleotide sequence (ToxoDB v7.3 TgGT1_107770)
Atgacctgccctccccgcgtccgtgaggccttcgccctcttcgacactgacggagatggtgagatctctggccg
cgacctcgtcctcgccatccgctcatgcggtgtgtctcccaccccagacgaaatcaaggcactcccatgtcaa
tggcgtggcctgattttgaggcgtggatgtcgaagaaactggcgtcctacaaccctgaggaggagttgatcaaa
tctttcaaggcttttgaccggtcgaacgacggcaccgtgtctgcggacgagctttctcaagttatgctcgctct
cggcgagttgctttccgacgaagaagtcaaggccatgatcaaggaagccgacccgaacggcactggcaagatcc
agtacgccaactttgtcaagatgctgctgaaataaggatccattgt.

SEQ ID NO: 48
*Toxoplasma gondii* ELC1 amino acid sequence, also referred to herein as TgELC1
MTCPPRVREAFALFDTDGDGEISGRDLVLAIRSCGVSPTPDEIKALPMSMAWPDFEAWMSKKLASYNPEEELIK
SFKAFDRSNDGTVSADELSQVMLALGELLSDEEVKAMIKEADPNGTGKIQYANFVKMLLK.

-continued

Partial Listing of Sequences

SEQ ID NO: 49: *Plasmodium falciparum* 3D7 myosin light chain, (may
also be referred to herein as an "essential type light chain", an
"essential light chain", a PfELC, and/or an ELC1) putative (PFF1320c) mRNA,
Genbank Accession No. XP_966255.2:
MEEIINEVELTSLFNKISEGSRTIHFEDAMEIIYKMGYVPSKEDINEFNNMTKGVCSLS
NIKKFCNKIRSLNYSTEGLLDIFHFYDTNKTGKISKEKLKLLFTTVGSKMSVDEMDTII
NELCNNDENIDYKEFLNRILN.

SEQ ID NO: 50: *Plasmodium falciparum* 3D7 myosin light chain (may also be
referred to herein as an "essential type light chain", an "essential light
chain", a PfELC, and/or an ELC1), putative (PFF1320c) mRNA,
NCBI Reference Sequence: XM_961162.2:
atggaggaaa taattaatga agtggaattg acttctcttt ttaacaagat atcagaaggg tcgagaacta
tccattttga ggatgccatg gaaataatat ataaaatggg ttatgttcct tcaaaagaag atataaatga
atttaacaac atgacaaaag gtgtttgttc tttatccaat ataaaaaagt tctgcaataa aataaggtca
ttgaattatt ccactgaagg tttgttggat atatttcatt tttatgatac aaataaaaca ggaaaaattt
ctaaagaaaa acttaaactc ttatttacaa cagttggttc aaaaatgtcg gttgatgaaa tggatacaat
aataaatgaa ttatgtaata acgatgaaaa catagactat aaggaatttc taaacaggat attaaattag.

BRIEF DESCRIPTION OF THE DRAWINGS

FIGS. 1A and 1B provide schematic diagrams of *T. gondii* myosin motor complex and subunit structure of TgMyoA. FIG. 1A shows TgMyoA (i.e., TgMyoA heavy chain with its bound light chains, TgMLC1 and TgELC1) and TgGAP45 are anchored to the inner membrane complex (IMC) via transmembrane protein TgGAP50. This multiprotein complex is referred to as the myosin motor complex. Short actin filaments are located between the parasite plasma membrane and the IMC, and are thought to be connected to ligands on the host cell surface through linker protein(s) that bind to the cytosolic tails of surface adhesins. TgMyoA (attached to the IMC) displaces the actin filaments (attached to the substrate) causing the parasite to move relative to the substrate. Note that alternative models of parasite motility are emerging (47, 48) in which TgMyoA plays a different but still important role in generating the force required for motility. Figure adapted from (12). FIG. 1B shows the subunit structure of TgMyoA. The heavy chain motor domain contains the actin and ATP binding sites, followed by the lever arm, to which the light chains TgMLC1 and TgELC1 are believed to bind. Rotation of the TgMyoA lever arm produces a power stroke that moves actin filaments and propels the parasite forward.

FIGS. 2A and 2B show schematics of the expressed proteins. FIG. 2A shows a TgMyoA heavy chain construct that contains the motor domain (red) and the light chain-binding region (black), followed by a Bio-tag and a FLAG-tag. FIG. 2B shows that TgUNC consists of three domains: TPR (at left end), central (middle section) and the UCS region (at right end), followed by a Myc tag. The three different TgUNC constructs used during coexpression with TgMyoA heavy chain are shown below the schematic.

FIG. 3 shows a Western blot of results demonstrating co-expression of TgMyoA with the chaperone TgUNC in Sf9 cells produces soluble heavy chain. Sf9 cells were co-infected with recombinant baculovirus coding for the TgMyoA heavy chain (HC) and its light chain TgMLC1. The Western blot shows the total (T) and soluble (S) protein fractions after 72 h infection in the absence (left two lanes) or presence (right two lanes) of co-expressed TgUNC. TgUNC was detected using anti-Myc antibody, while TgMyoA heavy chain was detected with anti-FLAG antibody.

FIG. 4A shows results of SDS-gel analysis of purified motor proteins. Lane 1, purified protein resulting from co-expression of TgMyoA heavy chain (HC), TgMLC1 light chain, and TgUNC. TgUNC only binds to unfolded protein and does not co-purify with TgMyoA. Lane 2, molecular weight standards. Lane 3, purified protein resulting from coexpression of TgMyoA heavy chain, TgMLC1 and TgELC1 light chains, and TgUNC. FIG. 4B shows a graph of results demonstrating sedimentation velocity of TgMyoA heavy chain expressed with TgMLC1. A sedimentation coefficient of 7.7S was determined by curve-fitting to one species. The symmetrical nature of the boundary indicates that a homogeneous species is present. OD, optical density.

(~29 kDa) with anti-Myc on left panels, anti TgMLC1 on right panels and 3×HA-ELC1 (~18 kDa) with anti-HA.

Figure 7A:
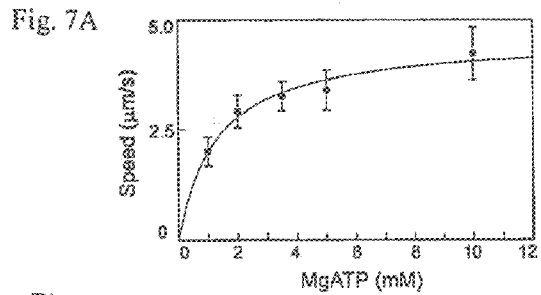
Figure 7B:
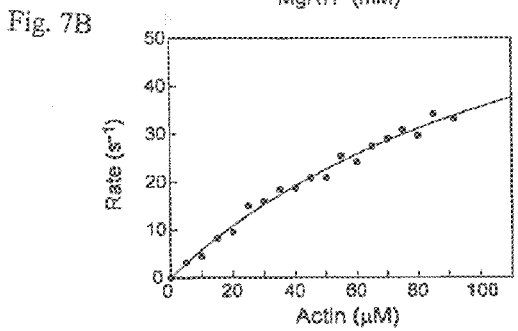

FIGS. 7A and 7B provide graphs of results of in vitro motility and steady-state actin-activated ATPase assays. FIG. 7A shows in vitro motility speed as a function of MgATP concentration. Solid line is a fit to Michaelis-Menten kinetics. Vmax=4.6±0.3 μm/s and KM=1.3±0.3 mM MgATP. FIG. 7B shows steady-state actin-activated ATPase assay as a function of skeletal actin concentration. Data were fit to the Michaelis-Menten equation: Vmax=84±9.5 s−1 and Km=136±22 04. Conditions: 10 mM imidazole, pH 7.0, 5 mM NaCl, 1 mM MgCl$_2$, 1 mM NaN$_3$, 5 mM MgATP and 1 mM DTT at 30° C.

Figure 8:
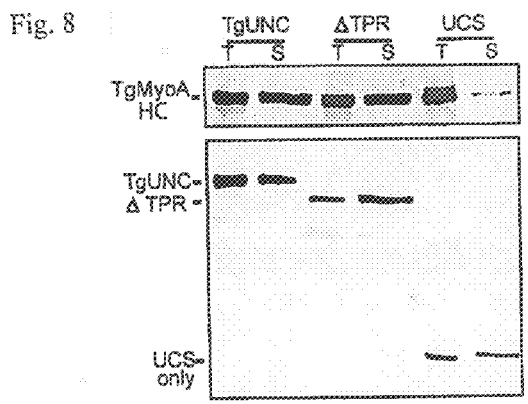

FIG. 8 shows Western blot results demonstrating that the TPR domain of TgUNC is not required for solubility of TgMyoA. Sf9 cell infections were performed with three TgUNC constructs (see FIG. 2B). Expression and solubility of TgMyoA were determined by Western blotting. Total (T) and soluble (S) fractions were probed with either anti-FLAG (top panel) for TgMyoA heavy chain (HC) or anti-Myc (bottom panel) for TgUNC and its truncations.

Figure 9:
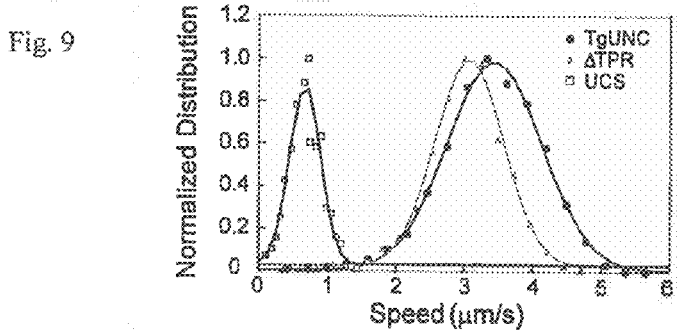

FIG. 9 provides a graph illustrating in vitro motility speeds of purified TgMyoA expressed with various TgUNC constructs. When TgMyoA was expressed with either full-length TgUNC or ΔTPR, the sliding speed with skeletal actin was similar: full-length TgUNC (3.4±0.7 μm/s, mean±SD, n=4, 774 filaments) and ΔTPR (3.1±0.5 μm/s, mean±SD, n=2,048 filaments). Speed decreased when TgMyoA was expressed in the presence of the UCS domain only (0.7±0.2 μm/s, mean±SD, n=1,296 filaments). The bin with the highest speed was normalized to one for presentation purposes. Data were obtained from three preparations of TgMyoA co-expressed with TgUNC, two protein preparations of TgMyoA co-expressed with ΔTPR, and one protein preparation of TgMyoA co-expressed with the UCS domain.

Figure 10:
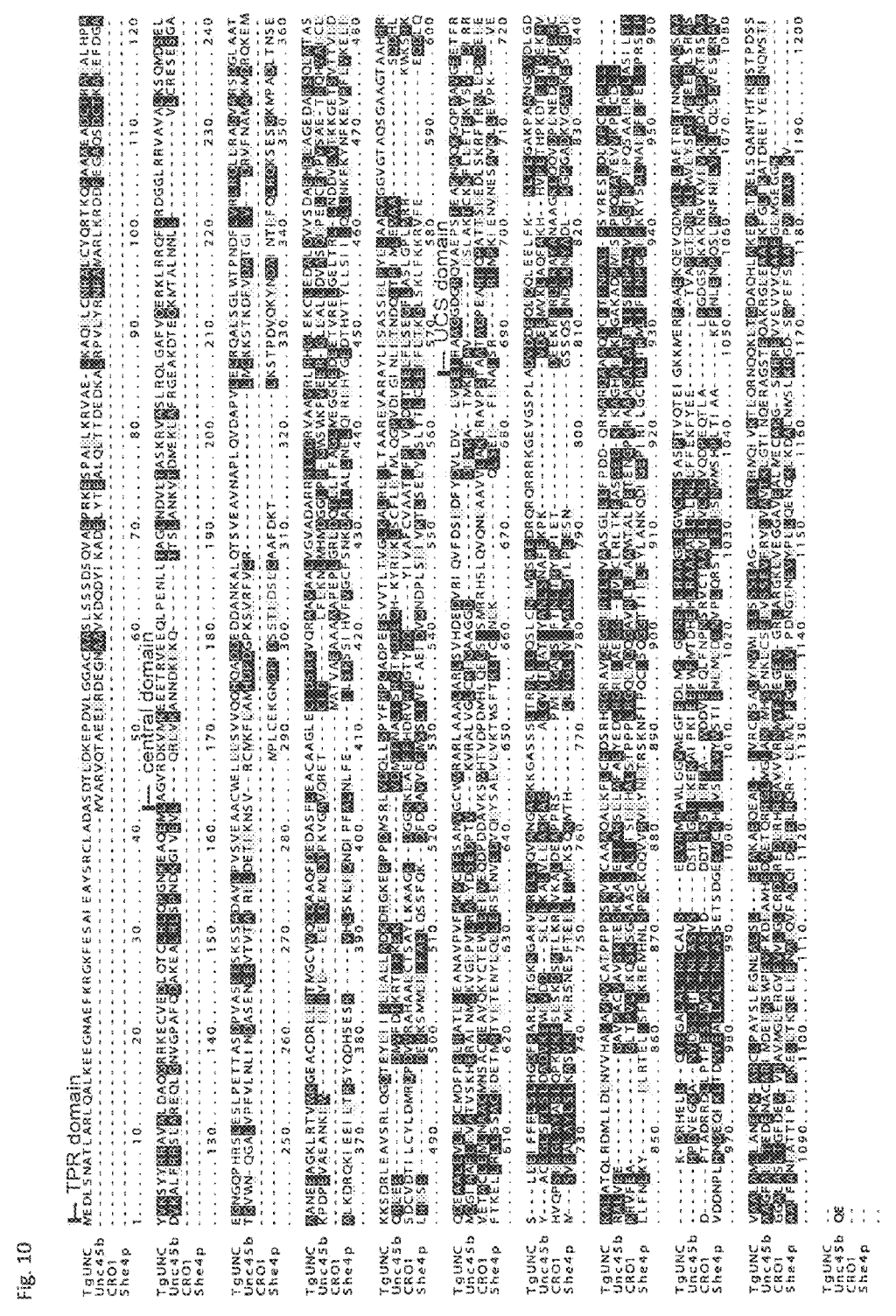

FIG. 10 shows a multiple sequence alignment of TgUNC (ToxoDB TgGT1_249480; GenBank Accession Number EPR63428.1, SEQ ID NO:12) with the three canonical members of the UCS family of myosin chaperones, i.e., *Caenorhabditis elegans* Unc45b [(AAD01976.1); SEQ ID NO:28], *Podospora anserina* CRO1 [(CAA76144.1); SEQ ID NO:29] and *Saccharomyces cerevisiae* She4p [(DAA10818.1); SEQ ID NO:30]. The alignment was generated using Multalin (http://multalin.toulouse.inra.fr/multalin/) (49) and processed using BoxShade v3.31C (http://mobyle.pasteur.fr/cgi-bin/portal.py#forms::boxshade). Identical residues are highlighted in black, similar residues in grey, and the start of the three domains (TPR domain, Central domain, and UCS domain) are shown above the sequence alignment. In TgUNC, L161 marks the start of the central domain, and E682 the start of the UCS domain. The percent identity/percent similarity of full-length TgUNC with the other UCS family members are: Unc45b, 17.4/28.7; CRO1, 9.5/16.3; She4p, 9.3/17.4. Comparing only the UCS domains, the percent identity/percent similarity with TgUNC is: Unc45b, 20.4/31.1; CRO1, 17.4/27.3; She4p, 15.3%/25.3.

FIG. 11 shows an amino acid sequence comparison of ARM motif residues in *Drosophila* UNC-45 and TgUNC. Sequence alignment of *Drosophila melanogaster* UNC-45 (DmUNC) [(accession number AAK93568); SEQ ID NO:31] with TgUNC [(ToxoDB TgGT1_249480; GenBank Accession Number EPR63428.1); SEQ ID NO:12], using the program ALIGN (http://xylian.igh.cnrs.fr/bin/align-guess.cgi) (50), shows 22.5% identity. The crystal structure of DmUNC has been determined (PDB ID: 3NOW) (51). Amino acid positions that conform to the ARM repeat consensus sequence and structural requirements proposed by Andrade et al. (52) were previously identified by Lee et al. (51), and are highlighted here. 40.4% of these ARM consensus residues (63 of 156) are identical in TgUNC (also highlighted). The last five ARM motifs (17-21, motif 17 starts around Arg715) are the proposed sites of interaction with myosin (51).

DETAILED DESCRIPTION

The invention, in part, relates to methods of preparing functional class XIV myosin and use of the prepared class XIV myosin in assays such as functional assays, drug screening assays, etc. In addition, the invention in some embodiments includes methods of preparing and using class XIV myosin, which may in some embodiments be associated with one or more myosin light chains. It has now been discovered that co-expression of a class XIV heavy chain polypeptide-encoding polynucleotide expressed with a parasite co-chaperone polypeptide-encoding polynucleotide can be used to prepare a functional class XIV myosin.

Myosins make up a family of ATP-dependent motor proteins and are involved in a number of motility processes. Motor proteins are a class of molecular motors that are able to move along the surface of a suitable substrate. Motor proteins are powered by the hydrolysis of ATP and are responsible for actin-based motility. The myosin genes are part of a large superfamily of genes whose protein products share the basic properties of actin binding, ATP hydrolysis (ATPase enzyme activity), and force transduction. Virtually all eukaryotic cells contain myosin isoforms, and the structure and function of myosin is strongly conserved across species. Most myosin molecules are include three domains, (1) the head domain that binds actin and uses ATP hydrolysis to generate force to move the actin, (2) the neck domain that is a binding region for one or more myosin light polypeptide chains and can also act as a "lever" to transduce force generated by the catalytic motor domain, and (3) the tail domain. Class XIV myosins are a myosin group that is found in the Apicomplexa phylum, including, importance, including *Toxoplasma gondii* (toxoplasmosis) and *Plasmodium* spp. (malaria). TgMyoA, the class XIV myosin in *T. gondii*, is necessary for efficient parasite motility, for invasion into and egress from host cells, and for virulence in a mouse model of infection. The speed of actin movement by myosin depends on both the kinetics of nucleotide binding and release from the motor domain, as well as the length of the lever arm, which is determined by the number of bound light chains.

It has now been discovered that expression of functional TgMyoA in a heterologous system requires co-expression with a co-chaperone of the UCS family. In some embodiments of the invention the co-chaperone is a *T. gondii* co-chaperone. The motor needs to bind two light chains (TgMLC1 and TgELC1) to propel actin at fast speeds. Heterologous expression of this unique myosin is the only way to obtain sufficient purified protein for structure-function studies as well as drug testing but not limited to Aplicomplexa members *Toxoplasma gondii* and *Plasmodium falciparum*.

Expression of Class XIV Myosin

A strategy of co-expression of a co-chaperone polypeptide with a class XIV heavy chain has now been used to prepare and isolate functional TgMyoA, a class XIVa myosin from the parasite *Toxoplasma gondii*, in expression system cells. Functional TgMyoA, also referred to herein as a "motor protein" or a "motor complex", is required for the parasite to efficiently move and invade host cells. The *T. gondii* genome contains one myosin co-chaperone of the UNC-45/Cro1/She4p (UCS) family, which is referred to herein as TgUNC. Functional protein was obtained when the TgMyoA heavy and light chain(s) were co-expressed with TgUNC. The tetratricopeptide repeat (TPR) domain of TgUNC was not essential to obtain fully functional myosin. It has now been identified that purified TgMyoA heavy chain complexed with its regulatory light chain (TgMLC1) moved actin in an ensemble motility assay at a speed of ~1.5 µm/s. When a putative essential light chain (TgELC1) was also co-expressed, TgMyoA moved actin at more than twice that speed (~3.4 µm/s). This indicated that both light chains bind to and stabilize the lever arm, which is the myosin domain that amplifies small motions at the active site into the larger motions needed to propel actin at fast speeds. These methods resulted in successful expression of milligram quantities of a class XIV myosin in a heterologous system, and the methods and the prepared class XIV myosin can be used to perform both detailed structure-function analysis of TgMyoA and to identify compounds that inhibit the class XIV myosin.

In one aspect the invention includes methods for producing a functional class XIV myosin polypeptide. The method in some embodiments may include co-expressing three or more polynucleotides in an expression-system cell, wherein the three or more polynucleotides comprise a class XIV heavy chain polypeptide-encoding polynucleotide, one or more myosin light chain polypeptide-encoding polynucleotides, and a parasite co-chaperone polypeptide-encoding polynucleotide. In certain embodiments of the invention, the three or more polynucleotides are co-expressed in the cell under conditions suitable to produce a functional class XIV myosin polypeptide comprising the class XIV heavy chain polypeptide and the first myosin light chain polypeptide.

Myosin Components

Some aspects of the invention include methods of preparing a functional class XIV myosin polypeptide. The term "class XIV myosin" as used herein, means a class XIV myosin heavy chain polypeptide complexed with at least one of a regulatory light chain (MLC1) and an essential light chain (ELC1). As used herein the term "complexed" or "complex" used in conjunction with myosin means binding together of various components such as a heavy chain and one or more light chain polypeptides to make up a class XIV myosin. For example, one or more light chains may bind to a myosin heavy chain, thus forming a myosin complex. Additional components and/or molecules may be included in a myosin complex include, but are not limited to actin, calmodulin, glideosome polypeptide, etc.

In certain embodiments of the invention, a functional myosin comprises a class XIV myosin heavy chain polypeptide complexed with an MLC1 polypeptide. In certain embodiments, a functional myosin of the invention comprises a class XIV myosin heavy chain polypeptide complexed with an ELC1 polypeptide. In certain embodiments, a functional myosin of the invention comprises a class XIV myosin heavy chain polypeptide complexed with an MLC1 polypeptide and an ELC1 polypeptide. MLC1 and ELC1 polypeptides may be collectively referred to herein as "light chain polypeptides".

Heavy Chain

Prepared functional myosins of the invention may in some embodiments comprise a sequence of a *Plasmodium falciparum* class XIV myosin heavy chain or a variant thereof. A non-limiting example of a nucleotide sequence that encodes a *Plasmodium falciparum* polypeptide referred to herein as a PfMyoA heavy chain, is set forth herein as SEQ ID NO:1, which encodes the *Plasmodium falciparum* class XIV heavy chain polypeptide having an amino acid sequence set forth herein as SEQ ID NO:2. In some embodiments of the invention, the heavy chain in a prepared functional class XIV myosin of the invention comprises a sequence of a *Toxomplasma gondii* class XIV myosin heavy chain or a variant thereof. A non-limiting example of a nucleotide sequence that encodes a *Toxomplasma gondii* polypeptide referred to herein as a TgMyoA heavy chain, is set forth herein as SEQ ID NO:15, which encodes the *Toxomplasma gondii* class XIV heavy chain polypeptide having an amino acid sequence set forth herein as SEQ ID NO:16. Sequences from additional apicomplexan organisms may also be used in methods of the invention to prepare class XIV myosins. Non-limiting examples of class XIV heavy chain polypeptide-encoding polynucleotides that may be used in methods of the invention to prepare a class XIV myosin include, but are not limited to polynucleotides that encode a *Toxoplasma, Plasmodium, Neospora, Sarcocystis, Eimeria,* or *Cryptosporidium* class XIV heavy chain polypeptide or a functional variant thereof.

Light Chains

Prepared functional myosins of the invention may in some embodiments comprise one, two, or more sequences of a light chain polypeptide or a variant thereof. As described herein, a light chain may be a "regulatory" light chain, referred to herein as an MLC1 polypeptide, which is also referred to in *P. falciparum* as Myosin A tail domain interacting protein (MTIP). In some embodiments of the invention, a regulatory light chain comprises the sequence of a *Plasmodium falciparum* regulatory light chain or a variant thereof. A non-limiting example of a nucleotide sequence that encodes a *Plasmodium falciparum* regulatory light chain polypeptide referred to herein as a MTIP light chain, is set forth herein as SEQ ID NO:5, which encodes the *Plasmodium falciparum* regulatory light chain polypeptide having an amino acid sequence set forth herein as SEQ ID NO:6. In some embodiments of the invention, the regulatory light chain in a prepared functional class XIV myosin of the invention comprises a sequence of a *Toxomplasma gondii* regulatory light chain or a variant thereof. A non-limiting example of a nucleotide sequence that encodes a Toxomplasma *gondii* polypeptide referred to herein as a MLC1, is set forth herein as SEQ ID NO:17, which encodes a *Toxomplasma gondii* MLC1 light chain polypeptide having an amino acid sequence set forth herein as SEQ ID NO:18.

As described herein, a light chain may be an "essential" light chain, referred to herein as an ELC1 polypeptide. In some embodiments of the invention, an essential light chain comprises the sequence of a *Plasmodium falciparum* essential light chain, or a variant thereof. A non-limiting example of a nucleotide sequence that encodes a *Plasmodium falciparum* essential light chain polypeptide referred to herein as an ELC1 light chain, is set forth herein as SEQ ID NO:7, which encodes the *Plasmodium falciparum* essential light chain polypeptide having an amino acid sequence set forth herein as SEQ ID NO:8. Another non-limiting example of a nucleotide sequence that encodes a *Plasmodium falciparum* essential type light chain polypeptide, which may also be referred to herein as an ELC1 light chain, is set forth herein as SEQ ID NO:50, which encodes the *Plasmodium falciparum* essential light chain polypeptide having an amino acid sequence set forth herein as SEQ ID NO:49. In some embodiments of the invention, the essential light chain in a prepared functional class XIV myosin of the invention comprises a sequence of a *Toxomplasma gondii* essential light chain or a variant thereof. A non-limiting example of a nucleotide sequence that encodes a *Toxomplasma gondii* essential light chain polypeptide, is set forth herein as SEQ ID NO:47, which encodes a *Toxomplasma gondii* essential light chain polypeptide having an amino acid sequence set forth herein as SEQ ID NO:48.

In certain embodiments of the invention, sequences from additional apicomplexan organisms may be used in methods of the invention to prepare class XIV myosins. Non-limiting examples of regulatory and/or essential light chain polypeptide-encoding polynucleotides that may be used in methods of the invention to prepare a class XIV myosin include, but are not limited to polynucleotides that encode a *Toxoplasma, Plasmodium, Neospora, Sarcocystis, Eimeria,* or *Cryptosporidium* light chain polypeptide or a functional variant thereof.

It will be understood that each apicomplexan polypeptide, or variant thereof, that is included in a class XIV myosin prepared using a method of the invention may be independently selected relative to other polypeptides included in the prepared functional class XIV myosin. For example, although not intended to be limiting, in certain embodiments of the invention a class XIV myosin heavy chain sequence may be a *Toxoplasma* sequence, or functional variant thereof; a MLC1 sequence may be a *Plasmodium* sequence, or functional variant thereof; and an ELC1 sequence may be a *Neospora* sequence or functional variant thereof. In additional non-limiting examples, in certain embodiments of the invention, each of the class XIV myosin heavy chain sequence, a MLC1 sequence, and/or an ELC1 sequence may be a *Plasmodium* sequence, or functional variant thereof; each may be a *Toxoplasma* sequence, or functional variant thereof; each may be an *Eimeria* sequence, or functional variant thereof, etc.

Additional Polypeptide Components

In certain aspects of the invention, methods of preparing a functional class XIV myosin includes expressing one or more additional polypeptides with a class XIV myosin heavy chain polypeptide and one or more light chain polypeptides. Examples of additional types of polypeptides that may be expressed with the heavy chain and one or more light chains include, but are not limited to calmodulin polypeptides and Glideosome Associated Protein-45 (GAP45) polypeptides. The TgMyoA motor is located between the plasma membrane and the inner membrane complex (IMC), a double membrane that is continuous around most of the cell. TgGAP50 (a 50 kDa gliding associated protein), an integral membrane glycoprotein of the IMC, acts as a membrane receptor for the motor. TgMyoA is linked indirectly to TgGAP50 through an apicomplexan-specific N-terminal extension of its regulatory light chain, TgMLC1, and TgGAP45 (a 45 kDa gliding associated protein). A similar linkage exists in other apicomplexan parasites, for example with PfMyoA, PfMTIP, PfGAP45, and PfGAP50 in *plasmodium falciparum*, and equivalent polypeptides present in other apicomplexan parasites MyoA complexes. Thus, certain embodiments of the invention may include expression of a GAP45 polypeptide. Such expression may enable an expressed myosin motor complex to express an increased level of activity. In certain embodiments of the invention, inclusion of a GAP45 polypeptide may be useful in methods and systems of the invention to screen and determine class XIV myosin activity, and in methods of the invention to screen for and to assess a candidate drug or agent's ability to alter activity of a functional class XIV myosin. Disruption of the connection between the MyoA motor and GAP45, mediated by TgMLC1 (or PfMTIP) may also be detrimental for glideosome function.

In some embodiments a calmodulin polypeptide comprises an amino acid sequence of a *Plasmodium falciparum* putative calmodulin sequence such as the amino acid sequence set forth herein as SEQ ID NO:10, or a variant thereof. The polypeptide set forth as SEQ ID NO:10 may be encoded by a nucleotide sequence set forth herein as SEQ ID NO:9. In some embodiments the calmodulin polypeptide comprises an amino acid sequence of a *Toxoplasma gondii* putative calmodulin sequence such as the amino acid sequence set forth herein as SEQ ID NO: 20, or a variant thereof. The polypeptide set forth as SEQ ID NO:20 may be encoded by a nucleotide sequence set forth herein as SEQ ID NO:19. Calmodulin (and putative calmodulin) sequences, and variants thereof, from additional apicomplexan organisms may also be used in methods of the invention to prepare class XIV myosins. Non-limiting examples of calmodulin polypeptide-encoding polynucleotides that may be expressed with a myosin heavy chain and light chain(s) in methods of the invention to prepare a class XIV myosin include, but are not limited to polynucleotides that encode a *Toxoplasma, Plasmodium, Neospora, Sarcocystis, Eimeria,* or *Cryptosporidium* calmodulin polypeptide or functional variant thereof.

In some embodiments a and glideosome Associated Protein-45 (GAP45) polypeptide comprises an amino acid sequence of a *Plasmodium falciparum* GAP45 sequence such as the amino acid sequence set forth herein as SEQ ID NO:44, or a variant thereof. The polypeptide set forth as SEQ ID NO:44 may be encoded by a nucleotide sequence set forth herein as SEQ ID NO:43. In some embodiments the GAP45 polypeptide comprises an amino acid sequence of a *Toxomplasma gondii* GAP45 sequence such as the amino acid sequence set forth herein as SEQ ID NO:46, or a variant thereof. The polypeptide set forth as SEQ ID NO:46 may be encoded by a nucleotide sequence set forth herein as SEQ ID NO:45. GAP45 sequences, and variants thereof, from additional apicomplexan organisms may also be used in methods of the invention to prepare class XIV myosins. Non-limiting examples of GAP45 polypeptide-encoding polynucleotides that may be expressed with a myosin heavy chain and light chain(s) in methods of the invention to prepare a class XIV myosin include, but are not limited to polynucleotides that encode a *Toxoplasma, Plasmodium, Neospora, Sarcocystis, Eimeria,* or *Cryptosporidium* GAP45 polypeptide or functional variant thereof.

Co-Chaperone Molecules

It has now been discovered that by co-expressing a class XIV myosin heavy chain polypeptide, one or more light chain polypeptide(s), and a parasite co-chaperone in a suitable cell system a functional class XIV myosin can be prepared. As used herein, the term "parasite co-chaperone" means a myosin co-chaperone that is a member of the UCS (UNC-45/Cro1/She4p) family. The UCS family is a group of proteins that are necessary for a variety of myosin- and actin-dependent functions in eukaryotic organisms. Methods of the invention, in some aspects include co-expression of a class XIV myosin heavy chain and at least one light chain with a member of the UCS family or a variant thereof.

In some embodiments of the invention, a UCS family co-chaperone that is expressed with a class XIV myosin heavy chain and one or more light chains is a UNC polypeptide variant. In some embodiments of the invention, a chaperone polypeptide encoding polynucleotide sequence comprises a homolog of the sequence of the C. elegans UNC-45 sequence and may be derived from a *Toxoplasma, Plasmodium, Neospora, Sarcocystis, Eimeria,* or *Cryptosporidium* organism.

In some embodiments the UNC polypeptide comprises an amino acid sequence of a *Plasmodium falciparum* UNC sequence such as the amino acid sequence set forth herein as SEQ ID NO:4, or a variant thereof. The polypeptide set forth as SEQ ID NO:4 may be encoded by a nucleotide sequence set forth herein as SEQ ID NO:3. In some embodiments the UNC polypeptide comprises an amino acid sequence of a *Toxomplasma gondii* UNC sequence such as the amino acid sequence set forth herein as SEQ ID NO: 12, or a variant thereof. The polypeptide set forth as SEQ ID NO:12 may be encoded by a nucleotide sequence set forth herein as SEQ ID NO:11. In certain embodiments of the invention, a truncated UNC polypeptide may be used to prepare a class XIV myosin using methods of the invention. A non-limiting example of a truncated UNC polypeptide, and its encoding nucleotide are set forth herein as SEQ ID NO:14 and SEQ ID NO:13, respectively. UNC sequences, and variants thereof, from additional apicomplexan organisms may also be used in methods of the invention to prepare class XIV myosins. Non-limiting examples of UNC polypeptide-encoding polynucleotides that may be used as a co-chaperone in methods of the invention to prepare a class XIV myosin include, but are not limited to polynucleotides that encode a *Toxoplasma, Plasmodium, Neospora, Sarcocystis, Eimeria*, or *Cryptosporidium* UNC polypeptide or functional variant thereof.

Labels/Tags

Expression constructs used in methods of the invention may comprise one or more of a detectable label, also referred to herein as a "tag". Thus, in certain embodiments, one or more polynucleotides that each encodes a polypeptide label may be included in a construct of the invention. Examples of polypeptide labels that may be encoded by a polynucleotide sequence included in a construct of the invention include, but are not limited to: a FLAG tag, a biotin acceptor site, a Myc tag, a His tag, or a Ty1 tag. Using standard methods, a skilled artisan will be able to identify and utilize additional types of detectable labels in embodiments of methods and constructs of the invention.

Expressed Polypeptides

It will be understood that various combinations of the polypeptide components described herein as being possible to include in a prepared myosin of the invention may be utilized in methods of the invention and in myosins prepared using such methods. In a non-limiting example, expression of a class XIV myosin polypeptide with a parasite co-chaperone may be suitable to prepare a class XIV myosin for assays such as structural assessment using crystallography, etc. Similarly, in other non-limiting examples methods of the invention, in some embodiments may include (1) expression of a class XIV myosin polypeptide, a parasite co-chaperone polypeptide and a regulatory myosin light chain polypeptide; (2) expression of a class XIV myosin polypeptide, a parasite co-chaperone polypeptide, and an essential myosin light chain polypeptide; (3) expression of a class XIV myosin polypeptide, a parasite co-chaperone polypeptide, a regulatory myosin light chain polypeptide, and an essential myosin light chain polypeptide; (4) expression of a class XIV myosin polypeptide, a parasite co-chaperone polypeptide, a regulatory myosin light chain polypeptide, and calmodulin; (5) expression of a class XIV myosin polypeptide, a parasite co-chaperone polypeptide; an essential myosin light chain polypeptide, and calmodulin; etc. Additional combinations of the components including, but not limited to those described herein may be used in embodiments of methods of the invention.

Polynucleotides, Polypeptides, and Modified/Variant Sequences

One aspect of the invention involves use of nucleic acid molecules that encode components of a functional class XIV myosin, a co-chaperone, or another polypeptide that may be complexed with a class XIV myosin as prepared using methods of the invention. As used herein, the terms "nucleic acid molecule" or "polynucleotide" are intended to include DNA molecules (e.g., cDNA or genomic DNA) and RNA molecules (e.g., mRNA). A nucleic acid molecule may be single-stranded or double-stranded or may be a double-stranded DNA molecule. An "isolated" nucleic acid molecule is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, may be free of other cellular material.

The invention further encompasses nucleic acid molecules that differ from the sequences set forth herein for a class XIV myosin heavy chain, light chains, UNC, calmodulin, GAP45, etc. (and portions thereof) due to degeneracy of the genetic code and thus encode the same polypeptide as that encoded by the disclosed sequences. Accordingly, in another embodiment, an isolated nucleic acid molecule of the invention has a nucleotide sequence encoding a protein having an amino acid sequence as set forth herein as a class XIV myosin heavy chain, light chains, UNC, calmodulin, GAP45, etc. (and portions thereof).

Aspects of the invention may include expression of class XIV myosin polypeptide sequences. Non-limiting examples of polypeptide sequences that may be used in embodiments of methods of the invention, include a class XIV myosin heavy chain polypeptide, a light chain, a UNC polypeptide, calmodulin, GAP45, etc. Such polypeptide sequences may comprise a wild-type polypeptide sequence or may be a modified polypeptide sequence that is a variant of a wild-type sequence.

As used herein the term "modified" or "modification" in reference to a variant nucleic acid or polypeptide sequence refers to a change of one, two, three, four, five, six, or more nucleotides or amino acids in the sequence as compared to the sequence from which it was derived. In a non-limiting example, a modified polypeptide sequence may be identical to a wild-type polypeptide sequence except that it has one, two, three, four, five, or more amino acid substitutions, deletions, insertions, or combinations thereof. In some embodiments a modified or variant sequence may be a truncated sequence that is shorter than the sequence from which it was derived. As used herein the term "derived" and "derived from" may mean a specific sequence may be obtained from a particular source albeit not necessarily directly from that source. In some embodiments of the invention a modified or variant sequence may include one, two, three, four, or more amino acid substitutions in a wild-type apicomplexan sequence. The term "functional variant" as used herein means a modified or variant sequence that retains at least a portion of the function or activity of the sequence from which it was derived. It will be understood that sequences of functional class XIV myosins as prepared using methods of the invention may be derived from various members of the apicomplexan family and may be independently selected relative to the other sequences used in the methods. Non-limiting examples of different wild-type amino acid sequences and nucleotide sequences and variant sequences are provided herein.

Routine sequence alignment methods and techniques can be used to align two or more substantially similar apicomplexan sequences, including but not limited to sequences from *Toxoplasma, Plasmodium, Neospora, Sarcocystis, Eimeria*, or *Cryptosporidium*, etc., thus providing a means by which a corresponding location of a modification made in one sequence can be identified in another corresponding apicomplexan sequence.

A polypeptide sequence used in methods of the invention, for example a heavy chain, a light chain, an UNC polypeptide, calmodulin, GAP45, etc. may include amino acid variants (e.g., polypeptides having a modified sequence) of the naturally occurring wild-type sequences, as set forth herein. Modified polypeptide sequences may have at least about 75%, 80%, 85%, 90%, 95%, 96%, 97%, 98%, 99%, or 100% residue similarity to the polypeptide sequence disclosed herein. Methods of the invention may in some embodiments, include use of homologs of polypeptides disclosed herein. Such sequence homology can be determined using standard techniques known in the art. Polypeptide and nucleotide sequences useful in embodiments of methods of the present invention include the polypeptide and nucleotide sequences provided herein and variants that have more than about 50%, 55%, 60%, 65%, 70%, 75%, 80%, 85%, 90%, 95%, 96%, 97%, or 98% sequence similarity to a provided sequence. The percent similarity between the two sequences is a function of the number of identical positions shared by the sequences (i.e., % similarity=number of identical positions/total number of positions×100). Such an alignment can be performed using any one of a number of well-known computer algorithms designed and used in the art for such a purpose.

Polypeptides useful in embodiments of the invention may be shorter or longer than their corresponding polypeptide sequences set forth herein. Thus, in some embodiments, a polypeptide included in a functional class XIV myosin is a full-length polypeptide or a functional fragment thereof. Similarly, one or more of a class XIV myosin heavy chain, a light chain, an UNC polypeptide, calmodulin, GAP45, or other polypeptides used in methods of the invention may be full-length polypeptides or functional fragments thereof. A fragment of a polypeptide may also be referred to herein as a truncated polypeptide.

In some aspects of the invention, substantially similar apicomplexan polypeptide sequences may have at least 80%, 85%, 90%, 91%, 92%, 93%, 94%, 95%, 96%, 97%, 98%, or 99% or 100% similarity to an apicomplexan sequence disclosed herein. Art-known alignment methods and tools can be used to align substantially similar sequences permitting positional identification of amino acids that may be modified as described herein to prepare additional polypeptides useful in methods of the invention to prepare functional class XIV myosin.

Sequence modifications can be in one or more of three classes: substitutions, insertions or deletions. These modified sequences, (which may also be referred to as variants) ordinarily are prepared by site specific mutagenesis of nucleic acids in the DNA encoding a polypeptide, using cassette or PCR mutagenesis or other techniques known in the art, to produce DNA encoding the modified polypeptide, and thereafter expressing the DNA in recombinant cell culture. Amino acid sequence variants are characterized by the predetermined nature of the variation, a feature that sets them apart from naturally occurring allelic or interspecies variation of the polypeptides used in various embodiments of the invention. Modified polypeptides used in embodiments of the invention generally exhibit the same qualitative biological activity as the naturally occurring analogue, although variants can also be selected which have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed modified polypeptide screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; and insertions usually will be on the order of from about 1 to 20 amino acids, although considerably larger insertions may be tolerated. Deletions may range from about 1 to about 20 residues, although in some cases deletions may be much larger. Substitutions, deletions, insertions or any combination thereof may be used to arrive at a final variant polypeptide used in methods and functional class XIV myosin of the invention. Generally these changes are done on a few amino acids to minimize the alteration of the molecule. However, larger changes may be tolerated in certain circumstances.

In some embodiments of the invention conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a polypeptide may be replaced with another amino acid residue from the same side chain family. Alternatively, in another embodiment, mutations can be introduced randomly along all or part of a polypeptide coding sequence, such as by saturation mutagenesis, and the resultant mutants can be screened for activity of the resulting polypeptide to identify mutants that retain activity when expressed to prepare a class XIV myosin in an embodiment of a method of the invention. Following mutagenesis of a sequence such as a nucleotide or polypeptide sequence set forth herein, the encoded protein can be expressed with components to prepare a class XIV myosin as described herein and the activity of the polypeptide can be determined, for example using an assay such as those described herein to assess function and activity of a prepared class XIV myosin.

Variants of polypeptides set forth herein, may exhibit the same qualitative class XIV myosin functionality activity as one or more of the sequences set forth herein, such as a class XIV myosin heavy chain polypeptide, a regulatory light chain polypeptide, an essential light chain polypeptide, a UNC polypeptide, a calmodulin polypeptide, etc. but may show some altered characteristics such as altered speed of actin movement, recovery, compatibility, and toxicity, or a combination thereof. For example, the polypeptide can be modified such that when used to prepare a class XIV myosin, the prepared class XIV myosin has an increased speed of actin movement or a higher level of complexing than when using another polypeptide.

A polypeptide of the invention such as a class XIV myosin heavy chain, a regulatory light chain, an essential light chain, a UNC polypeptide, a calmodulin polypeptide, etc. can incorporate unnatural amino acids as well as natural amino acids. An unnatural amino acid can be included in a polypeptide of the invention to enhance a characteristic (such of speed of actin movement, etc.) of a class XIV myosin that prepared with the polypeptide. Some embodiments of the invention include compositions that include one or more polypeptides of the invention, including but not limited to: a class XIV myosin heavy chain, a regulatory light chain, an essential light chain, a UNC polypeptide, and a calmodulin polypeptide. A composition may also include a carrier such as a buffer, solvent, solute, etc.

Another aspect of the invention provides nucleic acid sequences that code for a polypeptide used in methods of the invention to prepare a class XIV myosin. It would be understood by a person of skill in the art that the polypeptides of the present invention can be coded for by various nucleic acids. Each amino acid in the polypeptide is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for a polypeptide of the invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide. Some embodiments of the invention include compositions that include one or more nucleic acid sequences that encode a polypeptide of the invention, including but not limited to: a class XIV myosin heavy chain, a regulatory light chain, an essential light chain, a UNC polypeptide, and a calmodulin polypeptide. A composition may also include a carrier such as a buffer, solvent, solute, etc.

Amino acid and/or polynucleotide sequences that may be used in methods and expression systems of the invention, include, but are not limited to sequences that are derived from *Toxoplasma, Plasmodium, Neospora, Sarcocystis, Eimeria,* or *Cryptosporidium* amino acid and/or nucleic acid sequences. Sequences derived from sequences of various types of apicomplexan organisms can be used in methods and systems of the invention, including but not limited to *Toxoplasma*, including but not limited to *Toxoplasma gondii; Plasmodium*, including but not limited to *Plasmodium falciparum, P. vivax, P. knowlesi. P. ovale,* or *P. malariae; Neospora*, including but not limited to *Neospora caninu* or *Neospora hughesi; Sarcocystis*, including but not limited to *Sarcocystis neurona, bovihominis (S. hominis,),* or *S. suihominis; Eimeria*, including but not limited to *Eimeria tenella, E. bovis, E. necatrix, E. ellipsoidalis,* or *E. zuernii*; and *Cryptosporidium*, including but not limited to *Cryptosporidium parvum, C. hominis, C. canis, C. felis, C. meleagridis,* or *C. muris*. Those skilled in the art will readily recognize how to utilize sequences from these types of organisms to prepare functional class XIV myosin polypeptide using methods and systems of the invention. The term "protein" and "polypeptide" are used interchangeably herein.

Expression Systems

Vectors

Methods of the invention, in some embodiments, include use of recombinant expression systems. In embodiments of the invention, expression systems comprises host cells (prokaryotic or eukaryotic cells) that are transformed by vectors and recombinants and that are capable of expressing said RNA and/or DNA fragments. In certain aspects, the invention provides methods for preparing a functional class XIV myosin polypeptide comprising the steps of: (a) culturing a host cell containing a vector under conditions that provide for expression of the functional class XIV myosin polypeptide and (b) recovering the expressed functional class XIV myosin polypeptide sequence. This method, in some embodiments, may also include additional methods of (c) subjecting the prepared polypeptide to protein purification.

Some aspects of the invention also relate to methods for production/preparation of a recombinant functional class XIV myosin polypeptide, wherein the methods may include steps of: a) transforming an appropriate cellular host with one or more recombinant vectors, in which at least a class IX myosin heavy chain polynucleotide sequence or functional fragment thereof, a co-chaperone polynucleotide sequence or functional fragment thereof, and one or more light chain polynucleotide sequences or functional fragments thereof, have been inserted under the control of appropriate regulatory elements, b) culturing the transformed cellular host under conditions suitable for the expression of the insert, and, c) harvesting (e.g., isolating) a class XIV myosin polypeptide.

Vectors provided by the present invention may typically comprise a class IX myosin heavy chain polynucleotide sequence or functional fragment thereof, a co-chaperone polynucleotide sequence or functional fragment thereof, and one or more light chain polynucleotide sequences or functional fragments thereof encoding the desired amino acid sequence and preferably transcription and translational regulatory sequences operably linked to the amino acid encoding sequences so as to allow for the expression of the class XIV myosin polypeptide in the cell. In some embodiments of the invention, a vector will include appropriate prokaryotic, eukaryotic or viral promoter sequence followed by a nucleotide sequence as defined above. The recombinant vector of the invention may allow the expression of a class XIV myosin polypeptide in a prokaryotic, or eukaryotic host or in living mammals when injected as naked RNA or DNA.

The vector may comprise a plasmid, a cosmid, a phage, or a virus or a transgenic animal. In some embodiments of the invention, the vector is a baculovirus vector. Examples of such expression vectors and insect cell expression systems and methods are described in *The Baculovirus Expression System: A Laboratory Guide*, Linda King, Springer; 2012, the content of which is incorporated by reference herein. Many useful vectors are known in the art and may be obtained from such vendors as Stratagene, New England Biolabs, Promega Biotech, and others.

In certain embodiments of the invention vectors may include regulatory control sequences that allow for inducible expression of a class XIV myosin polypeptide, for example in response to the administration of an exogenous molecule. Alternatively, temporal control of expression of the class XIV myosin polypeptide may occur by only introducing the polynucleotide into the cell when it is desired to express the polypeptide.

Expression vectors may also include, for example, an origin of replication or autonomously replicating sequence and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate. Vectors of the invention may be prepared using methods described herein and with additional art-known standard recombinant techniques well known in the art and discussed, for example, in Molecular Cloning: a laboratory manual, Green, M. R., J. Sambrook, 2012 Cold Spring Harbor Laboratory Press, 4$^{th}$ Edition; *The Baculovirus Expression System: A Laboratory Guide*, Linda King, Springer; 2012, the content of which are incorporated by reference herein.

An appropriate promoter and other necessary vector sequences may be selected to be functional in the host, and may include, when appropriate, those naturally associated with apicomplexan (or other organism) sequences.

Expression and cloning vectors useful in embodiments of methods of the invention may contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

Vectors containing a class XIV myosin heavy chain polynucleotide sequence or functional fragment thereof, a co-chaperone polynucleotide sequence or functional fragment thereof, and one or more light chain polynucleotide sequences or functional fragments thereof sequences can be transcribed in vitro and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of a class XIV myosin heavy chain polynucleotide sequence or functional fragment thereof, a co-chaperone polynucleotide sequence or functional fragment thereof, and one or more light chain polynucleotide sequences or functional fragments thereof sequences into a host cell may be achieved by any method known in the art, including, inter alia, those described herein.

In certain embodiments of the invention a class XIV myosin heavy chain polynucleotide sequence or functional fragment thereof, a co-chaperone polynucleotide sequence or functional fragment thereof, and one or more light chain polynucleotide sequences or functional fragments thereof are part of a viral vector, such as a baculovirus vector, or infectious virus, such as a baculovirus. In certain embodiments of the invention, one, two, three, or more vectors are inserted into a cell for expression and in some embodiments of the invention, a viral transfer vector may be used that allows 1, 2, 3, 4, 5, or more polynucleotide sequences that a polypeptide to be inserted into the same vector so they can be co-expressed by the same recombinant virus.

Host Cells

To produce a cell capable of expressing a functional class XIV myosin polypeptide, polynucleotide sequences such as those that encode a class XIV myosin heavy chain polypeptide, a co-chaperone polypeptide, a calmodulin polypeptide, a GAP45 polypeptide, or one or more light chain polypeptides are incorporated into a recombinant vector, which is then introduced into a host prokaryotic or eukaryotic cell.

The invention, in some aspects, also provides host cells transformed or transfected with a one or more of an exogenous class XIV myosin heavy chain polynucleotide sequence, a co-chaperone polynucleotide sequence, a calmodulin polynucleotide sequence, a GAP45 polynucleotide sequence, or one or more light chain polynucleotide sequences. A host cell useful in embodiments of the invention may include but are not limited to a cell from yeast, filamentous fungi, a plant, insect, amphibian, avian species, bacteria, mammals, and human cells in tissue culture. In certain embodiments of the invention, a host cell may be a cell from *E. coli, Pseudomonas, Bacillus, Streptomyces*, yeast, CHO, R1.1, COS 1, COS 7, BSC1, BSC40, or BMT10 cells. In certain embodiments of the invention, a host cell is an Sf9 cell.

Large quantities of class XIV myosin polypeptide produced/prepared by expressing a class XIV myosin heavy chain polynucleotide sequence with a co-chaperone polynucleotide sequence and optionally with one or more of a calmodulin polynucleotide sequence, a GAP45 polynucleotide sequence, one or more light chain polynucleotide sequences—(or fragments of any of the listed polynucleotide sequences) in vectors or other expression vehicles in compatible prokaryotic or eukaryotic host cells.

In certain embodiments of the invention a prepared class XIV myosin polypeptide is isolated. As used herein, the term "isolated" when used in reference to a prepared polypeptide of the invention includes such polypeptides that are separated from the system in which they are expressed. Isolated prepared class XIV myosin polypeptides may be used in various assays to determine and measure activity of the myosin, to test the effect of contacting the myosin polypeptide with one or more candidate compounds, to assess function of the myosin polypeptide, etc.

Function and Assays

As used herein the term "functional" when used in regard to a class XIV myosin polypeptide means a class XIV myosin polypeptide that under suitable conditions will move actin. Actin movement may be detected and assessed using assays, such as, but not limited to, an ensemble motility assay. Such assays can be used to assess whether a prepared myosin polypeptide is functional, and also to determine a speed at which the functional myosin moves actin. In some embodiments a functional class XIV myosin moves actin at a speed of up to about 0.5, 1.0, 1.5, 2.0, 2.5, 3.0, 3.5, or 4.0 µm/s.

A number of different assays may be used to assess function of prepared class XIV myosin. Non-limiting examples include actin-activated APTase assays, which may include sensitive colorimetric methods that use malachite green and are compatible with high throughput plate screening, for example, 96-well plate screening. See for example Henkel, R. D., et al., (1988) *Anal. Biochem.* 169, 312-318. Actin pelleting methods may also be used in some aspects may include centrifugation of actin and myosin for 25 min at 350,000×g or other suitable conditions. Following centrifugation, myosin bound to actin is quantified using a method such as SDS-gel densitometry or by protein concentration determination in the supernatant. Another non-limiting example of an activity assay is an in vitro motility assay, as described in Trybus, K. M. (2000) *Methods* 22, 327-335. Additional assays are also suitable for determining and assessing function of a class XIV myosin, such as one prepared using a method of the invention, or other control class XIV myosins.

Methods of Activity/function Assessment

It has been identified that class XIV myosin activity may contribute to onset of infection of a subject by a parasite such as an apicomplexan organism. Function class XIV myosin prepared using methods of the invention may be useful in assays to identify compounds useful to prevent or treat an infection of a subject by a parasite such as an apicomplexan parasite. A compound that when contacted with a functional class XIV myosin reduces the myosin's activity by at least 1%, 5%, 10%, 20%, 30%, 40%, 50%, 60%, 70%, 80%, 90%, or 100%, may be a compound useful to prevent or treat an apicomplexan infection or to prevent contamination of a substrate by an apicomplexan organism. Methods of the invention, in some embodiments, include methods of identifying a compound as a candidate compound to inhibit a parasite that expresses a class XIV myosin polypeptide.

In certain embodiments of the invention, prepared myosin of the invention may be used to assess compounds that when contacted with a functional class XIV myosin increase the myosin's activity by at least 1%, 5%, 10%, 20%, 30%, 40%, 50%, 60%, 70%, 80%, 90%, or 100%, or more and thus enhance one or more functions or activities of an apicomplexan organism that expresses a class XIV myosin. Thus, the invention, in some embodiments, may include methods of identifying a compound as a candidate compound to enhance a parasite that expresses a class XIV myosin polypeptide.

Identification of Candidate Compounds

The invention, in some aspects also includes methods to identify candidate compounds that decrease (or increase) class XIV myosin activity when contacted with a cell, tissue, subject, or substrate. The invention, in part, may also include methods to assess the efficacy of candidate class XIV myosin activity-modulating compounds to decrease the level of expression and/or to reduce the level of an activity/function of a class XIV myosin polypeptide in a cell or organism. Such methods may be carried out in vivo in human or animal subjects; or using in vitro assays of the invention such as in cells from culture—e.g., as screening assays to assess compounds that may—modulate class XIV myosin directly or indirectly, for example by modifying level or activity of a co-chaperone, or other molecule. Such modulating compounds that directly or indirectly alter class XIV myosin polypeptide activity in a cell, tissue, or organism may be used in the treatment or prevention of an apicomplexan infection or contamination of a substrate by an apicomplexan organism.

Assays for assessing activity levels of a prepared class XIV myosin in embodiments of the invention may include determining one or more class XIV myosin levels and/or activities, including but not limited to determining levels of function/activity of components of a class XIV myosin polypeptide (e.g., a heavy chain, a light chain), or other polypeptides described herein such as a co-chaperone, calmodulin, a GAP45 polypeptide etc. that are co-expressed in methods of the invention useful to prepare a functional class XIV myosin. For example, assay methods of the invention may be used to determine whether a candidate compound interferes with (e.g., reduces) an interaction between a myosin heavy chain polypeptide and one or more light chains. In another non-limiting example of assays for candidate compounds, methods of the invention may also be used to determine whether a candidate compound interferes (e.g., reduces) an interaction between a co-chaperone and folding of the heavy chain. Such interference may reduce the function/activity of the prepared class XIV myosin and thus, contacting an apicomplexan organism with the compound may be useful to reduce the organism's ability to cause an infection and this prevent or treat an apicomplexan infection of a subject or apicomplexan contamination of a substrate.

As used herein, aspects of the invention may include assessment of interactions between component polypeptides that are part of a class XIV myosin complex or are used to prepare a functional class XIV myosin. Examples of such component polypeptides include, but are not limited to, a class XIV myosin heavy chain, a regulatory light chain, an essential light chain, calmodulin, a co-chaperone, a UCS polypeptide, a GAP45 polypeptide, etc. Assay methods of the invention may be used to assess whether a candidate compound interferes with interactions between one or more component polypeptides.

In some embodiments of the invention, a level of activity or interaction of one or more component polypeptides is measured in relation to a control level of the activity or interaction of the one or more component polypeptides. One possible measurement of the level a component polypeptide may be a measurement of an absolute level of a component polypeptide or its encoding nucleotide. This could be expressed, for example, in the level of a component polypeptide or encoding nucleotide per unit of cells or unit volume in an assay. Another measurement of a level of a component polypeptide or its encoding nucleotide may be a measurement of the change in the level of the component polypeptide or its encoding nucleotide over time. This may be expressed in an absolute amount or may be expressed in terms of a percentage increase or decrease over time.

In some aspects, the invention includes methods that provide information on the efficacy of a candidate compound to treat an apicomplexan infection or contamination. In certain aspects, the invention includes methods to assess activity and efficacy of compounds administered to a subject to prevent or treat an apicomplexan infection. Similarly, the invention in some embodiments may include methods to assess activity and efficacy of compounds contacted with an apicomplexan organism. Information about the stage or status of an infection or contamination by an apicomplexan organism and the efficacy of a compound or treatment of an infection by the organism can be used to assist a health-care provided to select a treatment for administration to a subject at risk or known to have an apicomplexan infection or can be used by a health-care professional to adjust (e.g., increase, decrease, or stop) a treatment that is being provided to such a subject.

As used herein a "subject" refers to any animal, such as, but not limited to a human, a non-human primate, a rodent, a dog, cat, bird, horse, or other animal. Thus, in addition to human medical application, some aspects of the invention include veterinary application of methods described herein.

In some aspects of the invention, methods are provided to identify candidate compounds for preventing or treating an apicomplexan infection of a subject and/or to reduce apicomplexan contamination of a substrate. Methods of the invention may be used to determine the efficacy of a compound for prevention and/or treatment of the infection or contamination. Such methods may include, for example, determining one or more levels of activity of a prepared functional class XIV myosin and contacting the class XIV myosin with a candidate compound and determining whether there is an increase, decrease, or no change in the activity of the class XIV myosin.

As described herein, a level of function/activity in a class XIV myosin prepared using methods of the invention can be determined using assay methods of the invention to measure the amount and/or activity of a prepared class XIV myosin molecule in an in vitro assay. As used herein, the term "measure" may refer to a determination of the presence or absence of activity of a prepared class XIV myosin and may refer to a determination of a level of activity of a prepared class XIV myosin. Methods of measuring activity of a class XIV myosin polypeptide are known in the art, and non-limiting examples of measuring means are provided herein.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Expression Constructs

Full length (FL) TgUNC was amplified from *T. gondii* cosmid #p559; (http://toxodb.org/toxo/; cosmid generously provided by Dr. M J Gubbels) using the primer pair TPR-ForANcoI and TPRRevAFullMycStpKpnI (see Table 1 for primer sequences). A Myctagged TgUNC PCR product was cloned into the baculovirus transfer vector pAcSG2 (BD Biosciences). TgUNC pAcSG2 was truncated to make two other constructs. TgUNCΔTPR starts at residue Leu161, eliminating the tetra-trico-peptide repeat region (TPR) but keeping the central and UCS domains along with the C-terminal Myc tag. The TgUNC UCS only construct starts with residue Glu682, thus eliminating both the TPR and central domains.

TABLE 1

List of oligonucleotides used for cloning.

| Gene | Primer name | Primer sequence | SEQ ID NO |
|---|---|---|---|
| TgUNC | TPR | cggcggtaccttacaggtcttc | 32 |
| | RevAFullMyc | ttcagagatcagtttctgtt | |
| | STPKpnI | cgcttgagtctgg. | |
| | TPRForANcol | agca ccatgg aggatttg tcaaacgc. | 33 |
| TgMyoA | EcoR1-FLAG-MyoF1 | gggggaattcatggactacaa agacgatgacgacaagatggc. | 34 |
| | c-TgMyoA-EcoRI | gggggaattcctactactag aacgccggctgaacagtc. | 35 |
| TgMLC1 | MLC-F | catggaattcatgagcaa ggtcgagaaga. | 36 |
| | MLC-R | catgagatcttgattactc ccttcgctcgag. | 37 |
| | 6HISMLC 1NdeIF | gcacaatcatatgcatca ccaccatcatcacagca aggtcgagaagaaatgc. | 38 |
| | MLC1BamHIR | gcacaatggatccttactcccttt cgctcgagcatt. | 39 |
| TgELC1 | 6HISELC 1NdeIF | gcacaatcatatgcatcacc accatcat cacacctgccctccccgcgt ccgt. | 40 |
| | ELC1BamHIR | gcacaatggatccttatttcag cagcatcttgacaaagt. | 41 |

The plasmid pEB2-FLAG-MyoA (Lucas Tilley and GEW, unpublished) was used as a template to amplify nFLAG tagged TgMyoA heavy chain (ToxoDB TgGT1_235470) using primer pair EcoR1-FLAG-MyoF1 and c-TgMyoA-EcoR1. The PCR product was cloned into the baculovirus transfer vector pAcUW51 (BD Biosciences). TgMyoA-cBiocFLAG was constructed by digesting TgMyoA heavy chain from pVL1392FLAGTgMyoA (Aoife Heaslip and GEW, unpublished) with BamHI/EcoRV and inserting the cleavage fragment into a modified version of pAcSG2 containing both a biotin acceptor site and FLAG tag at the C-terminus.

The TgMLC1 gene (ToxoDB TgGT1_257680) was PCR amplified from parasite cDNA using primers MLC-F and MLC-R and cloned untagged by ligation of the digested, gel extracted PCR product at the EcoRI and BglII restriction sites in pAcSG2. The 6×His tagged MLC1 gene was amplified from pAcSG2 TgMLC1 (Aoife Heaslip and GEW, unpublished) using the primer pair 6HISMLC1NdeIF and MLC1BamHIR. The resulting PCR product was cloned into the bacterial expression vector pET3a (Novagen).

The TgELC1 gene (ToxoDB v 7.3 TgGT1_107770) was PCR amplified from T. gondii RH strain cDNA. This entry codes for a 134 aa (~15 kDa) protein as described in (6) and can be viewed at http://v7-3.toxodb.org/toxo.b15/showRecord.do?name=GeneRecordClasses.GeneRecordClass& project_id=ToxoDB&source_id=TGGT1_107770 (last accessed Apr. 2, 2014). The PCR product was ligated downstream of the p10 promoter in vector pAcUW51 for baculovirus expression. In addition, a PCR product of TgELC1 with a 6×His tag using the primer pair 6HisELC1NdeIF and ELC1BamHIR was cloned into the bacterial expression vector pET3a (Novagen).

A dual light chain plasmid was constructed for immunoprecipitation studies. TgELC1 with a C terminus 3×HA tag was cloned into vector pAcUW51 downstream of the p10 promoter, while TgMLC1 with an N-terminal 3×Myc tag was cloned downstream of the polH promoter. All constructs were sequenced prior to transfection Co-Immunoprecipitations—

Sf9 cells were harvested 72 h after infection with recombinant baculoviruses (TgMyoA heavy chain and tagged light chains), and lysed with 10 mM imidazole Ph 7.4, 150 mM NaCl, 1 mM EGTA, 5 mM MgCl2, 7% (w/v) sucrose, 3 mM NaN3, 1% (v/v) NP-40, 1 mM DTT and 1× protease inhibitor cocktail (Sigma-Aldrich, catalog# P8340). Following addition of 5 mM MgATP, the lysate was spun at 350,000×g for 20 min at 4° C. The supernatant was incubated with either rabbit anti-TgMLC1 (a generous gift from Dr. Con Beckers) or rat anti-HA (Roche #11867423001) overnight at 4° C. Rec-Protein ASepharose beads (Invitrogen) were added and the samples incubated at 4° C. for 60 min. The beads were washed four times with lysis buffer. Bound proteins were eluted by boiling in SDS-PAGE sample buffer, centrifuged at 100×g for 2 min and resolved on 4-12% gradient gels. The protein was transferred to Immobilon-FL (Millipore, Bedford, Mass.) and probed with mouse anti-Myc 9E10 (1:2,000; Developmental Studies Hybridoma Bank, University of Iowa), rat anti-HA (1:400) or rabbit anti-HA (1:2,000, AbCam #9110) and mouse anti-FLAG (1:7,500, Sigma-Aldrich). LI-COR secondary antibodies (anti-Mouse IRDye680RD, anti-Rabbit IRDye800CW and anti-Rat IRDye800CW) were used according to manufacturer's instructions and blots were scanned using an Odyssey CLx Infrared Imaging System (LI-COR, Lincoln, Nebr.).

Protein Expression and Purification—

Sf9 cells were co-infected with recombinant baculovirus coding for TgMyoA heavy chain (tagged at the Cterminus with a Bio-tag and FLAG-tag), untagged light chain(s), and the co-chaperone TgUNC. The cells were grown in media supplemented with 0.2 mg/ml biotin. After 72 hours, the cells were lysed by sonication in 10 mM imidazole, pH 7.4, 0.2 M NaCl, 1 mM EGTA, 5 mM MgCl2, 7% (w/v) sucrose, 2 mM DTT, 0.5 mM AEBSF, 5 µg/ml leupeptin, and 5 mM benzamidine. To determine TgMyoA heavy chain solubility, the extracts were centrifuged at 350,000×g for 20 min. For motor purification, 25 µg/ml each of bacterially expressed TgMLC1 and TgELC1 (see below) and 5 mM MgATP were added to the lysate, which was then clarified at 200,000×g for 30 min. The supernatant was applied to a FLAG affinity resin column (Sigma-Aldrich) and washed with 10 mM imidazole, pH 7.4, 0.2 M NaCl, 1 mM EGTA, and 1 mM NaN3. TgMyoA was eluted from the column with 0.1 mg/ml FLAG peptide in the column buffer. The fractions of interest were combined and concentrated with an Amicon centrifugal filter device (Millipore) and dialyzed against 10 mM imidazole, pH 7.4, 0.2 M NaCl, 50% (v/v) glycerol, 1 mM DTT, and 1 µg/ml leupeptin for storage at −20° C.

HIS-tagged light chains (TgELC1 or TgMLC1) in pET3a (Novagen) were expressed in BLR(DE3) competent cells grown in LB broth. The cultures were induced with 0.4 mM IPTG and grown overnight at 27° C. before being pelleted and frozen. The pellets were lysed by sonication in 10 mM sodium phosphate, pH 7.4, 0.3 M NaCl, 0.5% (v/v) glycerol, 7% (w/v) sucrose, 7 mM β-mercaptoethanol, 0.5 mM AEBSF, and 5 µg/ml leupeptin. The cell lysate was clarified at 200,000×g for 30 min. TgELC1, which is found in the supernatant, was boiled for 10 min in a double boiler, and then clarified at 26,000×g for 30 min. Soluble protein was applied to a HIS-Select® nickel affinity column (Sigma-Aldrich). Non-specifically bound protein was removed by washing the resin with buffer A (10 mM sodium phosphate, pH 7.4, 0.3 M NaCl). TgELC1 was then eluted from the column with buffer A containing 200 mM imidazole. The protein was dialyzed overnight against 10 mM imidazole, pH 7.4, 150 mM NaCl, 1 mM EGTA, 1 mM MgCl2, and 50% (v/v) glycerol.

Bacterially expressed TgMLC1 is found in the insoluble inclusion bodies. The cell lysate was clarified at 26,000×g for 10 min. The pellet was dissolved in 20 ml of 8 M guanidine, 150 mM NaCl, 10 mM NaPO$_4$, pH 7.5, 10 mM DTT and stirred at room temperature until dissolved. It was then clarified at 200,000×g for 30 min and dialysed overnight against 2×1 liter of buffer A containing 7 mM β-mercaptoethanol and 1 µg/ml leupeptin. The next day the sample was clarified at 26,000×g for 30 min and the supernatant was applied to a HIS-Select® nickel affinity column (Sigma-Aldrich). The column was washed with 15 ml of dialysis buffer and TgMLC1 was eluted with buffer A containing 200 mM imidazole. The protein was dialyzed overnight against 10 mM Imidazole pH 7.4, 150 mM NaCl, 1 mM EGTA, 1 mM MgCl2, and 50% (v/v) glycerol. Both purified light chains were stored at −20° C.

Gels—

Proteins were separated on a 4-12% Bis-Tris NuPAGE gel (Invitrogen) run in MES buffer, per NuPAGE technical guide.

In Vitro Motility—

To prepare the flow cell, 0.2 mg/ml biotinylated BSA in buffer B (150 mM KCl, 25 mM imidazole, pH 7.5, 1 mM EGTA, 4 mM MgCl$_2$, 10 mM DTT) was added to the nitrocellulose-coated flow cells for 1 min, followed by 3 rinses with 0.5 mg/ml BSA in buffer B. Neutravidin (50 µg/ml; Thermo Scientific) in buffer B was applied for 1 min, followed by 3 rinses with buffer B. Before introduction into the flow cell, TgMyoA was mixed with a 2-fold molar excess of F-actin and 10 mM MgATP in buffer B and centrifuged for 25 min at 350,000×g to remove ATP-insensitive myosin heads. TgMyoA was then introduced into the flow cell at 70 µg/ml. To further block any ATP-insensitive heads, 1 µM vortexed F-actin in buffer C (50 mM KCl, 25 mM imidazole, pH 7.5, 1 mM EGTA, 4 mM MgCl$_2$, 10 mM DTT) was added for 60 s, followed by a 10 mM MgATP wash. Rhodamine-phalloidin-labeled actin was then introduced for 1 min, followed by one rinse with buffer C. Three volumes of Buffer C, which also contained 5 mM MgATP (unless stated otherwise), 0.5%-0.7% methylcellulose, 25 µg/ml TgMLC1 and 25 µg/ml TgELC1, 3 mg/ml glucose, 0.125 mg/ml glucose oxidase (Sigma-Aldrich), and 0.05 mg/ml catalase (Sigma-Aldrich), were then flowed in. When assayed with calcium, 1.2 mM calcium was added to this buffer.

Actin movement was observed at 30° C. using an inverted microscope (Zeiss Axiovert 10) equipped with epi-fluorescence, a Rolera MGi Plus Digital camera, and dedicated computer with the Nikon NIS Elements software package. Data were analyzed using a semi-automated filament tracking program described in (10). The velocities of >600 filaments were determined. Speeds were fit to a Gaussian curve.

Actin-Activated ATPase Activity—

Assays were performed in 10 mM imidazole, pH 7.0, 5 mM NaCl, 1 mM MgCl$_2$, 1 mM NaN3, and 1 mM DTT at 30° C. Purified TgMyoA (7.5 µg/ml) was incubated with various concentrations of skeletal actin. Activity was initiated by the addition of 5 mM MgATP and stopped with SDS every 2 min for 8 min. Inorganic phosphate was determined colorimetrically (33). The low salt concentration was needed to keep the Km values as low as possible. Data were fit to the Michaelis-Menten equation.

Sedimentation Velocity—

Sedimentation velocity runs were performed at 20° C. in an Optima XL-I analytical ultracentrifuge (Beckman Coulter) using the An60Ti rotor at 30,000 rpm. The solvent was 20 mM HEPES, pH 7.4, 0.1 M NaCl, 2 mM DTT. An N-terminally FLAG-tagged TgMyoA heavy chain (no Bio tag) bound to TgMLC1 was used for this experiment. The sedimentation coefficient was determined by curve fitting to one species, using the dc/dt program (34).

Results

TgMyoA Heavy Chain is Insoluble when Expressed in Sf9 Cells—

Recombinant baculoviruses encoding TgMyoA heavy chain and its regulatory light chain, TgMLC1, were used to co-infect Sf9 cells. The C-terminus of the TgMyoA heavy chain contained two tags: a FLAG-tag to facilitate purification by affinity chromatography, and a Biotag, which becomes biotinylated within the Sf9 cells (35) and allows the motor to be specifically attached via its C-terminus to a streptavidin-coated coverslip for in vitro motility assays (FIG. 2A). Although both TgMyoA heavy chain and TgMLC1 were expressed following infection, as detected by Western blotting of the total Sf9 cell lysate, none of the TgMyoA heavy chain was present in the soluble fraction (FIG. 3).

Identification of a UCS Family Gene in the *T. gondii* Genome—

The studies suggested that the endogenous Sf9 protein folding machinery was not sufficient to fold this unusual myosin, and that a parasite-specific co-factor was required. A potential candidate was a protein in the UCS family of myosin co-chaperones, of which UNC-45 from *C. elegans* is the founding member. Bioinformatic analysis of the *T. gondii* genome using either full length Unc45 or the UCS domain revealed a candidate, TgUNC (http://toxodb.org/toxo/; TgGT1_249480). The TgUNC amino acid sequence was aligned with the three canonical members of the UCS family of myosin chaperones (*C. elegans* Unc45b, *P. anserina* CRO1, and *S. cerevisiae* She4p) (FIG. 10). The percent identity/percent similarity of full-length TgUNC with the other UCS family members was determined and was found to be: Unc45b, 17.4/28.7; CRO1, 9.5/16.3; She4p, 9.3/17.4. Comparing only the UCS domains, the percent identity/percent similarity with TgUNC increases to: Unc45b, 20.4/31.1; CRO1, 17.4/27.3; She4p, 15.3/25.3. A schematic of the domain structure of TgUNC is shown in FIG. 2B.

Production of Soluble TgMyoA in Sf9 Cells Requires Co-Expression with TgUNC—

Figure 4A:
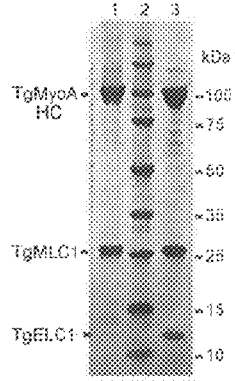
FIGS. 4A and 4B provide images of an SDS-gel showing characterization of purified TgMyoA and a graph.
Figure 4B:
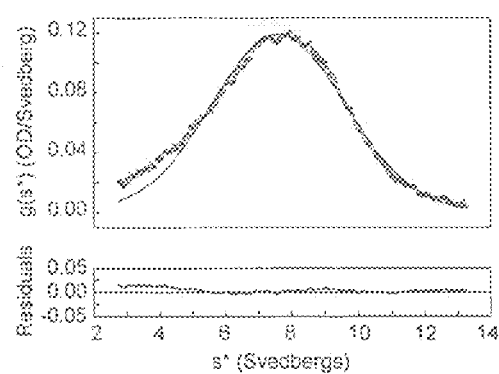

In marked contrast to what was observed in the absence of TgUNC, co-expression of TgMyoA heavy chain and TgMLC1 with TgUNC yielded soluble protein in small-scale infections (FIG. 3). A large-scale infection for protein purification was set up (500 ml culture, 3×10$^9$ Sf9 cells) using the same three viruses to co-infect Sf9 cells. TgMyoA was purified from the lysate using a FLAG-affinity column (see Methods above herein). Protein that bound to and eluted from the FLAG column showed two predominant bands on SDS-gels at the expected sizes of TgMyoA heavy chain and TgMLC1 (FIG. 4A, lane 1). The yield of purified motor was ~1.5 mg/$10^9$ Sf9 cells. The isolated expressed protein was analyzed by sedimentation velocity in the analytical ultracentrifuge. The results showed a single symmetrical peak with an S value of 7.75±0.01, indicating a homogeneous preparation of protein (FIG. 4B).

In Vitro Motility of Expressed TgMyoA Containing Bound TgMLC1—

Figure 5:
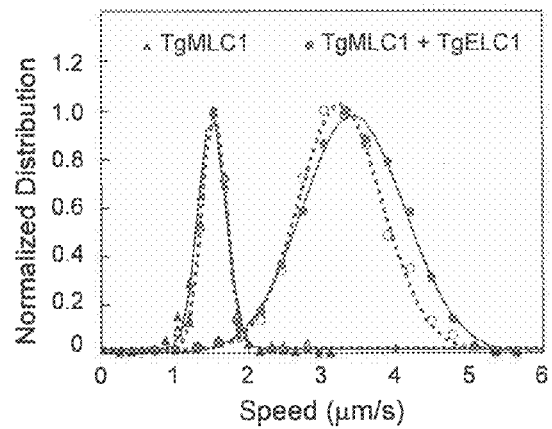
FIG. 5 shows a graph indicating that the number of bound light chains determines the speed of actin movement in an in vitro motility assay. The Gaussian fit of speeds for TgMyoA with TgMLC1 only was 1.5±0.2 µm/s (mean±SD, n=2,341 filaments) (solid triangles), compared to 3.4±0.7 µm/s (mean±SD, n=4,774 filaments) for TgMyoA with both light chains (solid circles). Conditions: 25 mM imidazole, pH 7.5, 50 mM KCl, 1 mM EGTA, 4 mM $MgCl_2$, 10 mM DTT, 5 mM MgATP, 0.5-0.7% (w/v) methylcellulose, and oxygen scavengers, 30° C. Addition of 1.2 mM calcium (i.e., 0.2 mM free calcium) did not affect motility speed (open symbols). In the presence of calcium, TgMyoA with TgMLC1 only moved actin at 1.5±0.2 µm/s (mean±SD, n=619 filaments), and TgMyoA containing both TgMLC1 and TgELC1 moved actin at 3.3±0.6 µm/s (mean±SD, n=1,729 filaments). The values obtained in calcium versus EGTA were indistinguishable (p>0.1, Kolmogorov-Smirnov test). For each dataset, the bin with the highest speed was normalized to one for presentation purposes. Data were obtained from three protein preparations of TgMyoA with both light chains, and two protein preparations of TgMyoA with TgMLC1 only.

Solubility does not ensure activity, so an in vitro motility assay was performed to assess function. TgMyoA with bound gMLC1 was perfused into a chamber containing a streptavidin-coated coverslip. The biotinylated tag at the C-terminus of TgMyoA heavy chain ensured that this region would adhere to the coverslip, leaving the motor domain accessible to bind actin. Expressed protein moved rhodamine-phalloidin labeled skeletal muscle actin at a speed of 1.5±0.2 μm/s (FIG. 5, solid triangles). Speeds were calculated using a semi-automated tracking program that allowed thousands of trajectories to be analyzed without selection bias (10). The speeds fit a Gaussian distribution.

The speed obtained with expressed protein was slower than the speed of protein isolated from parasites (8,12), which suggested a need to identify an additional component of the motor complex.

Co-Expression of TgMyoA Heavy Chain with Both TgMLC1 and TgELC1—

In addition to TgMLC1, an essential light chain called TgELC1 was recently identified as part of the myosin motor complex (6). When TgELC1 was co-expressed with TgMyoA heavy chain, TgMLC1, and TgUNC, both light chains were found to co-purify with the heavy chain, indicating that, like TgMLC1, TgELC1 is a tightly bound subunit of TgMyoA. When TgMyoA containing both light chains was assayed in the in vitro motility assay, it moved actin at 3.4±0.7 μm/s, more than twice the speed seen with TgMyoA containing only TgMLC1 (FIG. 5, solid circles).

Each TgMyoA Heavy Chain Binds Simultaneously to a Regulatory and Essential Light Chain—

Figure 6:
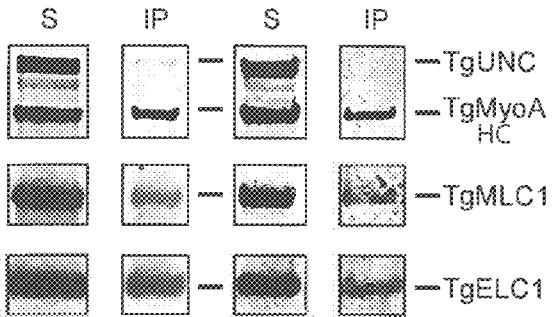
FIG. 6 shows immunoblot results demonstrating that both TgMLC1 and TgELC1 are bound to the same heavy chain. TgMyoA heavy chain (HC) was co-expressed in Sf9 cells with both 3×Myc-MLC1 and 3×HA-ELC1. TgMyoA was co-immunoprecipitated from cell lysates using either anti-HA antibody (to immunoprecipitate TgELC1; left panels), or anti-TgMLC1 antibody (right panels), confirming that each of the light chains bind to TgMyoA heavy chain. Furthermore, TgMLC1 is present in the TgELC1 pulldowns and vice versa, demonstrating that the two light chains are simultaneously present on the same MyoA heavy chain. TgUNC (~126 kDa) was detected with anti-Myc antibody, TgMyoA heavy chain (~104 kDa) with anti-FLAG, 3×Myc-TgMLC1

To test whether TgMLC1 and TgELC1 bind simultaneously to the same heavy chain, a recombinant baculovirus was prepared that contained both light chains, each with a different tag. TgMLC1 had an N-terminal 3×Myc tag, while TgELC1 had a C-terminal 3×HA tag. 72 hours following infection with heavy and light chains, TgMyoA was immunoprecipitated from the Sf9 cell lysate with either an anti-HA antibody (TgELC1) or an anti-TgMLC1 antibody (FIG. 6). The Myc antibody could not be used for TgMLC1 immunoprecipitation because TgUNC was also tagged with Myc. The eluates from the immunoprecipitation were analyzed by Western blotting with antibodies to detect TgUNC (anti-Myc), TgMyoA heavy chain (anti-FLAG), TgMLC1 (anti-Myc), and TgELC1 (anti-HA). The results showed that the proteins co-immunoprecipitating with TgMLC1 included TgELC1, and conversely that the proteins co-immunoprecipitating with TgELC1 included TgMLC1. Earlier work showed that individual motor complexes do not physically associate with each other (12), and it was conclude that both light chains are simultaneously present on the TgMyoA heavy chain.

Calcium does not Regulate Motility Speed—

To determine if calcium affects the speed at which TgMyoA moves actin, an in vitro motility assay was performed in the presence or absence of free calcium. TgMyoA was pre-incubated in buffer containing either 0.2 mM free calcium or 1 mM EGTA for one hour before performing the assay. Whether the myosin contained TgMLC1 or both light chains, no difference in speed was observed in the presence or absence of calcium (FIG. 5, open symbols).

Steady State Actin-Activated ATPase Activity—

The speed of actin filament movement increased as the MgATP concentration in the in vitro motility assay increased (FIG. 7A). The fit to a rectangular hyperbola defined a Vmax of 4.6±0.3 μm/s and a Km of 1.3±0.3 mM MgATP. Based on this observation, steady-state actin-activated ATPase assays were performed with 5 mM MgATP. Rates of ATP hydrolysis were determined as a function of skeletal actin concentration. Data were fit to the Michaelis-Menten equation. TgMyoA expressed with both light chains showed a Vmax of 84±9.5 $s^{-1}$ and a Km for actin of 136±22 μM at 30° C. (FIG. 7B).

The TPR Domain of TgUNC is not Required to Express Functional Myosin—

Having established the properties of functional TgMyoA, studies were performed to determine the minimal domain of TgUNC that produced an active motor. In addition to full-length TgUNC, two shorter constructs were cloned (FIG. 2B), one of which (ΔTPR) contained the central and UCS domains, while the other (UCS) contained the UCS domain only. Small-scale baculovirus infections were performed using these three TgUNC constructs, and expression and solubility of TgMyoA were determined by Western blotting. Total (T) and soluble (S) fractions were probed with either anti-FLAG (top panel) for TgMyoA heavy chain or anti-Myc (bottom panel) for TgUNC and its truncations (FIG. 8). The results showed that the TPR domain was dispensable to obtain soluble myosin, while the UCS domain alone produced very little soluble myosin.

To determine the functionality of the TgMyoA, large-scale infections and purifications were done with each of the TgUNC constructs, co-expressed with TgMyoA heavy chain and both light chains. All three infections yielded protein, but the yields were reduced for the two shorter TgUNC constructs. Per $10^9$ Sf9 cells, full-length TgUNC yielded ~1.5 mg TgMyoA, ΔTPR ~0.35 mg TgMyoA, and UCS only ~0.1 mg TgMyoA. In the in vitro motility assay, the motor expressed with either full-length TgUNC or ΔTPR generated similar actin sliding speeds (3.4±0.7 μm/s and 3.1±0.5 μm/s, respectively; see FIG. 9). In contrast, speeds decreased more than four-fold, to 0.7±0.2 μm/s, when TgMyoA was expressed in the presence of the UCS domain alone (FIG. 9).

DISCUSSION

It has now been shown that the class XIVa myosin motor TgMyoA simultaneously binds two light chains: the well-established TgMLC1 and a second light chain called TgELC1 (6,8). TgMyoA thus has a domain structure more similar to conventional myosins than previously appreciated. The results of the studies outlined above herein indicate that TgMyoA has a fairly conventional lever arm with two bound light chains, formed by TgELC1 and TgMLC1 binding to adjacent sites at the C terminus of the TgMyoA heavy chain. The lever arm functions to amplify small changes at the active site into the larger motions necessary to propel actin at fast speeds, and the length of the lever arm dictates the speed. TgMyoA with only TgMLC1 bound moved actin at half the speed of TgMyoA with both TgMLC1 and TgELC1 bound (1.5 μm/s vs. 3.4 μm/s). Consistent with the functional data, reciprocal co-immunoprecipitations showed that the TgMyoA heavy chain simultaneously bound both types of light chains, establishing that TgMLC1 and TgELC1 bind to non-overlapping sites on the heavy chain.

Role of TgMyoA Light Chains—

The results of the studies indicate that TgELC1 is a bona fide subunit of TgMyoA. The in vitro motility data show that TgMyoA moves actin at the same speed in the presence or absence of calcium, and does not support the idea that calcium binding directly regulates this motor. Increased levels of intracellular calcium within the parasite may instead trigger signaling pathways that lead to increased association of TgELC1 with TgMyoA.

Motor Activity—

The steady-state ATPase assay showed that TgMyoA has a low affinity (i.e., a high Km) for actin in the presence of MgATP, as expected for a single-headed motor. The extrapolated maximal ATPase rate of ~80 sec-1 gives a total time per cycle of MgATP hydrolysis of ~12 msec. From the measured unitary step-size (duni) of 5.3 nm (8) and a speed of actin movement of ~3.4 μm/s (v), the time the motor spends strongly attached to actin is ~1.5 msec (ton=duni/v). This is a small percentage of the total cycle time, and thus this motor has a low duty cycle, as do most motors designed for speed.

Proper Folding of TgMyoA Heavy Chain Requires a Parasite-Specific Myosin Co-Chaperone—

A main finding of the studies described herein was that a *T. gondii* myosin co-chaperone is required to properly fold TgMyoA heavy chain in the baculovirus/Sf9 insect cell expression system. This was the first demonstration that functional class XIV myosin from an apicomplexan parasite can be expressed in a heterologous system. While TgMyoA can be purified directly from the parasite, the yields are low, making it difficult to rigorously characterize the parasite-derived motor complex. With the heterologous expression system described herein, yields of 1 mg were readily attainable from $1 \times 10^9$ infected Sf9 cells (200 ml culture), comparable to yields obtained with myosins that do not require coexpression with an exogenous chaperone. Importantly, the speed at which expressed TgMyoA with two bound light chains moves actin in an in vitro motility assay (~3.4 μm/s) is close to the speed of the motor complex isolated from parasites (~5 μm/s) (8,12). The difference in the two values may be simply due to differences in the way the speeds were calculated. In studies described herein, a tracking program was used that calculates speeds of hundreds of moving filaments without user-bias, while prior studies tracked individual filaments manually.

The TPR Domain of TgUNC is not Required for its Chaperone Activity—

TgUNC has all three domains found in the canonical Unc45 protein, i.e., an N-terminal TPR domain, a central domain, and a C-terminal UCS domain that binds to myosin (see FIG. 2B). It has now been shown that the N-terminal TPR domain of TgUNC is not necessary to obtain functional TgMyoA in Sf9 cells. Both the myosin-binding UCS domain and the central domain are, however, required.

The long-sought goal of obtaining milligram quantities of TgMyoA has now been reached, which for the first time makes high-throughput screening for drugs against this unusual, virulence-associated motor possible. Furthermore, the results of these studies supports a conclusion that genomes of other apicomplexan parasites encode homologs of TgUNC, and that the approach described herein may be used for the expression of functional class XIV myosins from other apicomplexan parasites of medical and/or veterinary importance.

REFERENCES

1. Foth, B. J., et al, (2006) *Proc. Natl. Acad. Sci. USA* 103, 3681-3686.
2. Meissner, M., et al., (2002) *Science* 298, 837-840.
3. Sheffield, H. G., and Melton, M. L. (1968) *J. Parasitol.* 54, 209-226.
4. Gaskins, E., et al., (2004) *J. Cell Biol.* 165, 383-393.
5. Frenal, K., et al., (2010) *Cell Host Microbe.* 8, 343-357.
6. Nebl, T., et al., (2011) *PLoS Pathog.* 7, e1002222.
7. Heintzelman, M. B., and Schwartzman, J. D. (1997) *J. Mol. Biol.* 271, 139-146.
8. Herm-Gotz, A., et al., (2002) *EMBO J.* 21, 2149-2158.
9. Bement, W. M., and Mooseker, M. S. (1995) *Cell Motil. Cytoskeleton* 31, 87-92.
10. Kinose, F., et al., (1996) *J. Cell Biol.* 134, 895-909.
11. Hettmann, C., et al., (2000) *Mol. Biol. Cell* 11, 1385-1400.
12. Heaslip, A. T., et al., (2010) *PLoS Pathog.* 6, e1000720.
13. Leung, J. M., et al., (2014) *PLoS One* 9, e85763.
14. Hakansson, S., et al., (1999) *Mol. Bio. Cell* 10, 3539-3547.
15. Moore, J. R., et al., (2004) *J. Muscle Res. Cell Motil* 0.25, 29-35.
16. Warshaw, D. M., et al., (2000) *J. Biol. Chem.* 275, 37167-37172.
17. Tyska, M. J., and Warshaw, D. M. (2002) *Cell Motil. Cytoskeleton* 51, 1-15.
18. Trybus, K. M. (1994) *J. Biol. Chem.* 269, 20819-20822.
19. Pato, M. D., et al., (1996) *J. Biol. Chem.* 271, 2689-2695.
20. De La Cruz, E. M., et al., (1999) *Proc. Natl. Acad. Sci. USA* 96, 13726-13731.
21. Trybus, K. M., et al., (1999) *J. Biol. Chem* 0.274, 27448-27456.
22. Wang, F., et al., (2000) *J. Biol. Chem.* 275, 4329-4335.
23. Wells, A. L., et al., (1999) *Nature* 401, 505-508.
24. Yang, Y., et al., (2005) *J. Biol. Chem.* 280, 32061-32068.
25. Chow, D., et al., (2002) *J. Biol. Chem.* 277, 36799-36807.
26. Srikakulam, R., and Winkelmann, D. A. (1999) *J. Biol. Chem.* 274, 27265-27273.
27. Srikakulam, R., and Winkelmann, D. A. (2004) *J. Cell Sci.* 117, 641-652.
28. Barral, J. M., et al., (2002) *Science* 295, 669-671.
29. Liu, L., et al., (2008) *J. Biol. Chem.* 283, 13185-13193.
30. Srikakulam, R., et al., (2008) *PLoS One* 3, e2137.
31. Scheufler, C., et al., (2000) *Cell* 101, 199-210.
32. Hutagalung, A. H., et al., (2002) *J. Cell Sci.* 115, 3983-3990.
33. Trybus, K. M. (2000) *Methods* 22, 327-335.
34. Philo, J. S. (2000) *Anal. Biochem.* 279, 151-163.
35. Cronan, J. E., Jr. (1990) *J. Biol. Chem.* 265, 10327-10333.
36. Beckingham, K. (1991) *J. Biol. Chem.* 266, 6027-6030.
37. Bergman, L. W., et al., (2003) *J. Cell Sci.* 116, 39-49.
38. Bosch, J., et al., (2007) *J. Mol. Biol.* 372, 77-88.
39. Turley, S., et al., (2013) *Mol. Biochem. Parasitol.* 190, 56-59.
40. Treeck, M., et al., (2011) *Cell Host Microbe* 10, 410-419.
41. Sakamoto, T., et al., (2003) *J. Biol. Chem.* 278, 29201-29207.
42. Douse, C. H., et al., (2012) *J. Biol. Chem.* 287, 36968-36977.
43. Lee, C. F., et al., (2011) *Structure* 19, 397-408.
44. Shi, H., and Blobel, G. (2010) *Proc. Natl. Acad. Sci. USA* 107, 21382-21387.
45. Mishra, M., et al., (2005) *Eukaryot. Cell* 4, 567-576.
46. Ni, W., et al., (2011) *J. Cell. Sci.* 124, 3164-3173.
47. Andenmatten, N., et al., (2013) *Nat. Methods* 10, 125-127.
48. Egarter, S., et al., (2014) *PLoS One* 9, e91819.
49. Corpet F (1988) *Nucleic Acids Research November 25*; 16(22): 10881-10890.
50. Pearson W R, et al., (1997) *Genomics* 46(1):24-36.
51. Lee C F, et al. (2011) *Structure* 19(3):397-408.
52. Andrade M A, et al., (2001) *J Mol Biol* 309(1):1-18.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents, patent applications, and non-patent publications that are cited or referred to in this application are incorporated in their entirety herein by reference.

What is claimed is:

1. A method of producing a functional class XIV myosin polypeptide, the method comprising,
co-expressing three or more polynucleotides in a heterologous expression-system cell, wherein the three or more polynucleotides comprise a class XIV heavy chain polypeptide-encoding polynucleotide, a first myosin light chain polypeptide-encoding polynucleotide, and a parasite co-chaperone polypeptide-encoding polynucleotide, wherein the three or more polynucleotides are co-expressed in the cell under conditions suitable to produce a functional class XIV myosin polypeptide comprising the class XIV heavy chain polypeptide and the first myosin light chain polypeptide.

2. The method of claim 1, wherein the class XIV heavy chain polypeptide-encoding polynucleotide, the parasite co-chaperone polypeptide-encoding polynucleotide, and the first myosin light chain polypeptide-encoding polynucleotide are each independently selected from a *Toxoplasma, Plasmodium, Neospora, Sarcocystis, Eimeria,* or *Cryptosporidium* class XIV heavy chain polypeptide-encoding polynucleotide; a parasite co-chaperone polypeptide-encoding polynucleotide; and a myosin light chain polypeptide-encoding polynucleotide, respectively; and wherein the encoded class XIV heavy chain polypeptide comprises an amino acid sequence having at least 75% sequence similarity to a wild-type class XIV heavy chain polypeptide or a functional fragment thereof; the encoded first myosin light chain polypeptide comprises an amino acid sequence having at least 75% sequence similarity to a wild-type myosin light chain polypeptide or a functional fragment thereof; and the encoded parasite co-chaperone polypeptide comprises an amino acid sequence having at least 75% sequence similarity to a wild-type parasite co-chaperone polypeptide or a functional fragment thereof.

3. The method of claim 1, wherein co-expressing comprises co-infecting the heterologous expression-system cell with one or more expression vectors each comprising one or more of the three or more polynucleotides.

4. The method of claim 3, wherein the one or more expression vectors is a viral expression vector.

5. The method of claim 3, wherein co-infecting the heterologous expression-system cell comprises co-infecting with one or more expression vectors comprising one or more of the class XIV heavy chain polypeptide-encoding polynucleotide operably linked to an independently selected promoter, the first myosin light chain polypeptide-encoding polynucleotide operably linked to an independently selected promoter, and the parasite co-chaperone polypeptide-encoding polynucleotide operably linked to an independently selected promoter.

6. The method of claim 3, wherein co-infecting the heterologous expression-system cell comprises co-infecting with a first expression vector comprising the class XIV heavy chain polypeptide-encoding polynucleotide operably linked to an independently selected promoter, a second expression vector comprising the first myosin light chain polypeptide-encoding polynucleotide operably linked to an independently selected promoter, and a third expression vector comprising the parasite co-chaperone polypeptide-encoding polynucleotide operably linked to an independently selected promoter.

7. The method of claim 3, wherein the one or more of the expression vectors additionally comprises one or more polynucleotides that encode: a myosin light chain-1 (MLC1) polypeptide having at least 75% similarity to the sequence of a wild-type MLC1 polypeptide or a functional fragment thereof; a tail domain interacting protein (MTIP) polypeptide having at least 75% similarity to the sequence of a wild-type MTIP polypeptide or a functional fragment thereof; an essential light chain-1 (ELC1) polypeptide having at least 75% similarity to the sequence of a wild-type ELC1 polypeptide or a functional fragment thereof; a calmodulin polypeptide having at least 75% similarity to the sequence of a wild-type calmodulin) polypeptide or a functional fragment thereof; or a glideosome associated protein-45 (GAP45) polypeptide having at least 75% similarity to the sequence of a wild-type GAP45 polypeptide or a functional fragment thereof.

8. The method of claim 3, wherein one or more of the expression vectors additionally comprise at least one polynucleotide sequence that encodes a detectable label, and wherein the functional class XIV myosin polypeptide comprises the expressed detectable label polypeptide.

9. The method of claim 1, wherein the parasite co-chaperone polypeptide-encoding polynucleotide sequence comprises a UNC-45/Cro1/She4p (UCS) chaperone polynucleotide sequence encoding a parasite co-chaperone polypeptide having at least 75% similarity to the sequence of a wild-type UNC-45/Cro1/She4p (UCS) polypeptide or a functional fragment thereof, respectively.

10. The method of claim 1, wherein the encoded parasite co-chaperone polypeptide comprises an amino acid sequence having at least 75% similarity to the sequence of a wild-type *toxoplasma gondii* UCS-45 homolog or a functional fragment thereof; or a wild-type *Toxoplasma* UNC (TgUNC) polypeptide or a functional fragment thereof.

11. The method of claim 1, wherein the parasite co-chaperone polypeptide comprises an amino acid sequence having at least 75% similarity to: the sequence of a wild-type *Plasmodium falciparum* UCS-45 homolog or a functional fragment thereof; or a wild-type *Plasmodium falciparum* UNC (PfUNC) polypeptide, or a functional fragment thereof.

12. The method of claim 11, wherein the PfUNC functional fragment is a truncated PfUNC polypeptide.

13. The method of claim 1, wherein the heterologous expression system is a baculovirus/insect cell expression system.

14. The method of claim 1, wherein the first myosin light chain polypeptide is a regulatory light chain (MLC1) polypeptide comprising an amino acid sequence having at least 75% similarity to: a wild-type *Toxoplasma gondii* regulatory light chain polypeptide sequence or a functional fragment thereof; or a wild-type *Plasmodium falciparum* regulatory light chain polypeptide sequence or a functional fragment thereof.

15. The method of claim 1, further comprising isolating the expressed functional class XIV myosin polypeptide.

16. The method of claim 1, further comprising assaying the function of the expressed functional class XIV myosin polypeptide.

17. The method of claim 1, further comprising co-infecting the heterologous expression-system cell with an expression vector comprising a second myosin light chain encoding polynucleotide; and
co-expressing the class XIV heavy chain polynucleotide, the first and second myosin light chain polynucleotides, and the parasite co-chaperone polynucleotide under conditions suitable to produce a functional class XIV myosin polypeptide comprising the class XIV heavy chain polypeptide and the first and second myosin light chain polypeptides.

18. A functional class XIV myosin polypeptide prepared by the method of claim 8.

19. A method of determining an activity of a class XIV myosin polypeptide, the method comprising,
(a) preparing a functional class XIV myosin polypeptide with a method comprising co-expressing three or more polynucleotides in an expression-system cell, wherein the three or more polynucleotides comprise a class XIV heavy chain polypeptide-encoding polynucleotide, a first myosin light chain polypeptide-encoding polynucleotide, and a parasite co-chaperone polypeptide-encoding polynucleotide, wherein the three or more polynucleotides are co-expressed in the cell under conditions suitable to produce a functional class XIV myosin polypeptide comprising the class XIV heavy chain polypeptide and the first myosin light chain polypeptide;
(b) assaying an activity of the prepared functional class XIV myosin polypeptide; and
(c) assessing the results of the assay as a determination of activity in the functional class XIV myosin polypeptide.

20. A method of identifying a candidate compound to inhibit a parasite that expresses a class XIV myosin polypeptide, the method comprising,
(a) preparing a functional class XIV myosin polypeptide with a method comprising,
co-expressing three or more polynucleotides in an expression-system cell, wherein the three or more polynucleotides comprise a class XIV heavy chain polypeptide-encoding polynucleotide, a first myosin light chain polypeptide-encoding polynucleotide, and a parasite co-chaperone polypeptide-encoding polynucleotide, wherein the three or more polynucleotides are co-expressed in the cell under conditions suitable to produce a functional class XIV myosin polypeptide comprising the class XIV heavy chain polypeptide and the first myosin light chain polypeptide;
(b) contacting the functional prepared class XIV myosin polypeptide with a candidate compound under conditions suitable to determine an activity of the class XIV myosin polypeptide;
(c) determining the activity of the functional class XIV myosin polypeptide; and
(d) comparing the determined activity with a control activity determination, wherein a decrease in the determined activity in the contacted functional class XIV myosin polypeptide compared to the control activity determination identifies the compound as a candidate compound to inhibit a parasite that expresses the functional class XIV myosin polypeptide.

21. The method of claim 1, wherein the encoded class XIV heavy chain polypeptide comprises an amino acid sequence having at least 75% sequence similarity to a wild-type class XIV heavy chain polypeptide or a functional fragment thereof; the encoded first myosin light chain polypeptide comprises an amino acid sequence having at least 75% sequence similarity to a wild-type myosin light chain polypeptide or a functional fragment thereof; and the encoded parasite co-chaperone polypeptide comprises an amino acid sequence having at least 75% sequence similarity to a wild-type parasite co-chaperone polypeptide or a functional fragment thereof.

* * * * *

SEQUENCE LISTING

```
<160> NUMBER OF SEQ ID NOS: 50

<210> SEQ ID NO 1
<211> LENGTH: 2457
<212> TYPE: DNA
<213> ORGANISM: Plasmodium falciparum

<400> SEQUENCE: 1
atggctgtta caaatgaaga aataaaaacg gcaagtaaga ttgttagaag agtttcaaat        60
gtagaagcat ttgacaaaag tggttcagtt tttaagggtt atcaaatatg gactgatata      120
tctccgacaa tagaaaatga tccaaatatt atgtttgtaa aatgtgttgt acaacaagga      180
tcaaaaaaag aaaaattaac cgttgtacaa attgatccac ccggaacagg aactccatac      240
gatattgatc caactcacgc atggaactgc aactctcaag tagaccccat gtcttttggt      300
gatattggtc ttttaaatca caccaacatc ccatgtgttc ttgactttt aaagcacaga      360 tatttaaaaa atcaaatata caccactgct gttcccctta ttgttgcaat aaacccatac      420
aaggatttag gaaacacaac taatgaatgg attcgtagat atcgtgatac agctgatcat      480
actaagttgc caccacacgt gttcacatgt gctagggaag ctttgtctaa tctccatggt      540
gtaaacaaga gccaaactat tattgtatct ggtgaatctg gtgcaggaaa aaccgaagca      600
acaaaacaaa tcatgagata ttttgcttct tctaagagtg gaaatatgga tttacgtatt      660
cagacagcaa taatggctgc aaatccagtt cttgaagctt ttggtaatgc gaaaactata      720
agaaataaca attcatctcg ttttggtcgt ttcatgcagt tggttatatc ccatgaagga      780
ggtataagat acggttccgt tgttgctttt ctgttggaaa aatctagaat tattacacaa      840
gatgataatg aaaggtcata tcatatattt tatcaatttc ttaagggtgc aaatagtacg      900
atgaaatcta aatttggttt aaaaggagtt actgaataca aattattgaa cccaaattca      960
acagaggtaa gtggagtaga tgatgtaaaa gatttgaag aggtaattga atcgttgaaa     1020
aatatggaat taagtgaatc agatattgaa gtaatattt caatagtagc tggtatatta     1080
acattaggaa atgtaagatt aattgagaag caagaagctg gattaagtga tgctgctgct     1140
attatggatg aggatatggg tgtgtttaat aaagcttgtg aattgatgta tttagaccct     1200
gaattaataa aaagggaaat attaattaag gtaactgttg ctggaggaac aaaaattgaa     1260
ggtagatgga ataaaaatga tgcagaagtg ttgaaatctt ccttatgtaa agctatgtat     1320
gagaaattgt ttttatggat aataagacat ttgaattcaa gaattgaacc agaaggagga     1380
```

-continued

```
tttaaaacat ttatgggtat gttagatatt tttggttttg aagtatttaa aaataattca   1440
ttggaacaat tatttattaa cattactaac gaaatgcttc agaaaaattt tgtagatatt   1500 gttttgaaa gagaatcaaa attatataaa gacgaaggaa tatcaacagc tgaattaaag    1560
tacaccagta ataaggaagt aataaacgta ctttgtgaga agggtaaatc agtactttca   1620
tacttagagg accaatgttt agcacctgga ggaaccgatg aaaagtttgt aagttcctgt   1680
gctacaaatt taaaggaaaa taataagttt accccagcaa aagtagcatc gaataaaaat   1740
tttataatac aacatactat aggaccaatt caatattgtg ctgaaagctt tttgcttaaa   1800
aacaaggatg tcttaagagg tgatttagtt gaagtaatta aggattcccc caatccaata   1860
gtacaacagt tatttgaagg tcaagtaatt gagaagggta aaatagctaa aggttcatta   1920
ataggttctc aatttttaaa tcaattgaca tctttaatga acttgataaa tagtactgaa   1980
ccacatttca tacgttgtat taaaccaaat gaaaataaaa aaccattaga atggtgtgaa   2040
ccaaaaatat taattcagct tcatgcctta tcaattttag aagcattagt attaagacaa   2100
ttaggatatt cttatagaag aacctttgaa gaattcttat atcaatataa atttgtggac   2160
attgctgctg ctgaagattc atcagttgaa accaaaata aatgtgttaa tatattaaag   2220
ttgtctggac tatctgaatc catgtataag ataggaaaaa gcatggtctt tttgaaacaa   2280
gaaggtgcaa aaatattgac aaaaatacaa agagagaaac ttgttgaatg ggaaaattgt   2340
gtgagtgtaa ttgaagctgc tatacttaaa cacaaataca aacaaaaggt taacaaaaat   2400
ataccttctc ttttgagagt acaagctcat ataagaaaaa aatggtagc tcaataa      2457
```

<210> SEQ ID NO 2
<211> LENGTH: 818
<212> TYPE: PRT
<213> ORGANISM: Plasmodium falciparum

<400> SEQUENCE: 2

```
Met Ala Val Thr Asn Glu Glu Ile Lys Thr Ala Ser Lys Ile Val Arg
  1               5                  10                  15

Arg Val Ser Asn Val Glu Ala Phe Asp Lys Ser Gly Ser Val Phe Lys
                 20                  25                  30

Gly Tyr Gln Ile Trp Thr Asp Ile Ser Pro Thr Ile Glu Asn Asp Pro
             35                  40                  45

Asn Ile Met Phe Val Lys Cys Val Val Gln Gln Gly Ser Lys Lys Glu
         50                  55                  60

Lys Leu Thr Val Val Gln Ile Asp Pro Pro Gly Thr Gly Thr Pro Tyr
 65                  70                  75                  80

Asp Ile Asp Pro Thr His Ala Trp Asn Cys Asn Ser Gln Val Asp Pro
                 85                  90                  95

Met Ser Phe Gly Asp Ile Gly Leu Leu Asn His Thr Asn Ile Pro Cys
            100                 105                 110

Val Leu Asp Phe Leu Lys His Arg Tyr Leu Lys Asn Gln Ile Tyr Thr
        115                 120                 125

Thr Ala Val Pro Leu Ile Val Ala Ile Asn Pro Tyr Lys Asp Leu Gly
    130                 135                 140

Asn Thr Thr Asn Glu Trp Ile Arg Arg Tyr Arg Asp Thr Ala Asp His
145                 150                 155                 160

Thr Lys Leu Pro Pro His Val Phe Thr Cys Ala Arg Glu Ala Leu Ser
                165                 170                 175

Asn Leu His Gly Val Asn Lys Ser Gln Thr Ile Ile Val Ser Gly Glu
            180                 185                 190
```

```
Ser Gly Ala Gly Lys Thr Glu Ala Thr Lys Gln Ile Met Arg Tyr Phe
            195                 200                 205

Ala Ser Ser Lys Ser Gly Asn Met Asp Leu Arg Ile Gln Thr Ala Ile
    210                 215                 220

Met Ala Ala Asn Pro Val Leu Glu Ala Phe Gly Asn Ala Lys Thr Ile
225                 230                 235                 240

Arg Asn Asn Asn Ser Ser Arg Phe Gly Arg Phe Met Gln Leu Val Ile
                245                 250                 255

Ser His Glu Gly Gly Ile Arg Tyr Gly Ser Val Val Ala Phe Leu Leu
            260                 265                 270

Glu Lys Ser Arg Ile Ile Thr Gln Asp Asp Asn Glu Arg Ser Tyr His
        275                 280                 285

Ile Phe Tyr Gln Phe Leu Lys Gly Ala Asn Ser Thr Met Lys Ser Lys
    290                 295                 300

Phe Gly Leu Lys Gly Val Thr Glu Tyr Lys Leu Leu Asn Pro Asn Ser
305                 310                 315                 320

Thr Glu Val Ser Gly Val Asp Asp Val Lys Asp Phe Glu Glu Val Ile
                325                 330                 335

Glu Ser Leu Lys Asn Met Glu Leu Ser Glu Ser Asp Ile Glu Val Ile
            340                 345                 350

Phe Ser Ile Val Ala Gly Ile Leu Thr Leu Gly Asn Val Arg Leu Ile
        355                 360                 365

Glu Lys Gln Glu Ala Gly Leu Ser Asp Ala Ala Ile Met Asp Glu
    370                 375                 380

Asp Met Gly Val Phe Asn Lys Ala Cys Glu Leu Met Tyr Leu Asp Pro
385                 390                 395                 400

Glu Leu Ile Lys Arg Glu Ile Leu Ile Lys Val Thr Val Ala Gly Gly
                405                 410                 415

Thr Lys Ile Glu Gly Arg Trp Asn Lys Asn Asp Ala Glu Val Leu Lys
            420                 425                 430

Ser Ser Leu Cys Lys Ala Met Tyr Glu Lys Leu Phe Leu Trp Ile Ile
        435                 440                 445

Arg His Leu Asn Ser Arg Ile Glu Pro Glu Gly Phe Lys Thr Phe
    450                 455                 460

Met Gly Met Leu Asp Ile Phe Gly Phe Glu Val Phe Lys Asn Asn Ser
465                 470                 475                 480

Leu Glu Gln Leu Phe Ile Asn Ile Thr Asn Glu Met Leu Gln Lys Asn
                485                 490                 495

Phe Val Asp Ile Val Phe Glu Arg Glu Ser Lys Leu Tyr Lys Asp Glu
            500                 505                 510

Gly Ile Ser Thr Ala Glu Leu Lys Tyr Thr Ser Asn Lys Glu Val Ile
        515                 520                 525

Asn Val Leu Cys Glu Lys Gly Lys Ser Val Leu Ser Tyr Leu Glu Asp
    530                 535                 540

Gln Cys Leu Ala Pro Gly Gly Thr Asp Glu Lys Phe Val Ser Ser Cys
545                 550                 555                 560

Ala Thr Asn Leu Lys Glu Asn Asn Lys Phe Thr Pro Ala Lys Val Ala
                565                 570                 575

Ser Asn Lys Asn Phe Ile Ile Gln His Thr Ile Gly Pro Ile Gln Tyr
            580                 585                 590

Cys Ala Glu Ser Phe Leu Leu Lys Asn Lys Asp Val Leu Arg Gly Asp
        595                 600                 605
```

```
Leu Val Glu Val Ile Lys Asp Ser Pro Asn Pro Ile Val Gln Gln Leu
610                 615                 620

Phe Glu Gly Gln Val Ile Glu Lys Gly Lys Ile Ala Lys Gly Ser Leu
625                 630                 635                 640

Ile Gly Ser Gln Phe Leu Asn Gln Leu Thr Ser Leu Met Asn Leu Ile
                645                 650                 655

Asn Ser Thr Glu Pro His Phe Ile Arg Cys Ile Lys Pro Asn Glu Asn
                660                 665                 670

Lys Lys Pro Leu Glu Trp Cys Glu Pro Lys Ile Leu Ile Gln Leu His
                675                 680                 685

Ala Leu Ser Ile Leu Glu Ala Leu Val Leu Arg Gln Leu Gly Tyr Ser
                690                 695                 700

Tyr Arg Arg Thr Phe Glu Glu Phe Leu Tyr Gln Tyr Lys Phe Val Asp
705                 710                 715                 720

Ile Ala Ala Ala Glu Asp Ser Ser Val Glu Asn Gln Asn Lys Cys Val
                    725                 730                 735

Asn Ile Leu Lys Leu Ser Gly Leu Ser Glu Ser Met Tyr Lys Ile Gly
                740                 745                 750

Lys Ser Met Val Phe Leu Lys Gln Glu Gly Ala Lys Ile Leu Thr Lys
                755                 760                 765

Ile Gln Arg Glu Lys Leu Val Glu Trp Glu Asn Cys Val Ser Val Ile
770                 775                 780

Glu Ala Ala Ile Leu Lys His Lys Tyr Lys Gln Lys Val Asn Lys Asn
785                 790                 795                 800

Ile Pro Ser Leu Leu Arg Val Gln Ala His Ile Arg Lys Lys Met Val
                805                 810                 815

Ala Gln

<210> SEQ ID NO 3
<211> LENGTH: 3738
<212> TYPE: DNA
<213> ORGANISM: Plasmodium falciparum

<400> SEQUENCE: 3
atgcaggaat tgttatgaa tattcttagt aaagaaaaaa ttgggaaaat agaaaaacta      60
aaaaatgatg ggaatgaatt atatcgaaat aaaaaatata aggaggcttt atgtatatat     120
gataatgctg tttgtgagtt tgtggaggt tcaggtgata gtttaaaaat taaggaaatg     180
gtgaaagaat tttcaaaaaa tgatgagact aataatataa ataaattatc agatgataat    240
aataataata atatgattga tgaaaataat aagaaatgtg attttctta tatatgtgaa     300 attcaaaatt tattcataaa aatatgccat aatatatcat tatgttatta tttcttagaa    360
gattttgaaa atctattga atattgttta tatattaatg aaatgaacaa taatcattat    420
aaaagttacc acacgcttgg gttgtgttat gagaaattaa agattatca aaagagtata    480 cattattttg ataggtgtaa aatagtactt ttaaaaaatc aaaacaataa aaataaagac    540
aataataata aaagtgaaat taatcgaatt aatgaaaagt tacgtgatat tatgaaaatt    600
atagatcaaa ataaaaatga tccatataaa aatataagca acattaaaaa atatcttctt    660
gatgaaaata caaataatat aaatgacatt gaagaaaata ataaaaaaat taaattgtta    720
cattctattt ataatcaaaa gttttatata ctacttaagg aaaatatttt tttatttctt    780 tttgattta ttaaaaaaaa taatgacata tcaaactatg acgattgcaa taataataat    840
aataataata atttatatag tcataatatt aatagtttat tattagaaaa aacagccatt    900
```

```
tatgttattt ataaaatatt atccaaatta gataatgaac atattattat tgaaaattcc    960
aaagatgata actataataa aaatcgtaat atatgtatta acaaattaga taattcaaag   1020
cttcaatatt attatgatct agattatatt aaaatgattt tatcctttaa tgaatatttt   1080
acaaaagatt ggatatataa ttatataaaa aaaaaaatca atatattaga aaatttaaag   1140
ttttcaaaag atgaaacctt atataaagaa catgtagaca ttttaatcta tatcataaat   1200
attatgaaat atgtctatgt tataaataat gattatattt taaatattat taattcctat   1260
tatttaaata gcgataattc taatattaat aactctggta ttaatgctct tacattctta   1320
tgtaaaaaaa aacaatttt aacacaaaat agtaaggata atagaaaaaa aaaaaatgat    1380
ttattagaaa tgcttaaaaa agaaaattac ttaaatatac aaaataatat acaaaataat   1440
aataataata ataattatta tttttataag aatgaattta ttgaatttca cttttcggac   1500
tctcataaat atccattgtg tatcaattcc gaaatcaaaa aaattataca aatgttatt    1560
ggtatgtatg aacactttc tagtagtata gaatataccttaattttaat ttttacttta   1620
ttacatgacc cacaaagacc taaggaaaaa gacatagaaa tgaatgatgt aatttatgat   1680
tgtatagata attattttca tcataatgaa atattttga tagaatggtt tgtatgtatt    1740
aaatgtcttt tcttagtaga taaaaatatt atattaaatt atttaatagg aaaaacagaa   1800
tatattgtaa aaatcttaca ttttattacg aactgtatag gaagaaaaac taagaagaa    1860
ttatccatat atatcgatgt cttattactt ttattgaata tatcagaaat acgttttatg   1920
tttactaatt atattgatat gtatataaat aaatgaaat ctttaaatta tgatcaatgc    1980
tttttgaaac ttttactagg tacatttaaa ttatacatgc acaacataga ctttaaacaa   2040
caaattcaag ataatgtgga tttgttcttt tatgcgaaag aaatattaaa gcaattctta   2100
ttaacatatg ataatgatgc ggacggaaaa aataacacga ataatgataa aagagaagaa   2160
aatgaggaac agacaagcca tttgaattat tctaatttaa attcgtacac atgctgtgtg   2220
aaaaaatgtg atgataatga tacaaagaaa aaagatatta taaaccaaaa gaaagatgaa   2280
aagaataaga aacattgtga acttgtagat aagaaaaaaa aagatcatac atatatacat   2340
tcgaatatga gttgtgaaaa aacgttaaaa gatttaatag aaatgttatt ttatttaagt   2400
ttgcatattg aatttaaaaa acaattatta gaggaaaaaa ataattatat tttattttc    2460
ttaataaaag ttggacatga tataaataaa aagaaattag ataacacata taatatata    2520
tattgcaaca ctataaataa tttaattta acaaaaaatg atgaaaaaat aaaaagaaga    2580
gaaattaata aaactaattt atcaaatttt gataatgaac aaatagaagc tttagaacaa   2640
ttttatgata aattaccaaa agaagctaga cctaaaacag atccattata tgattatgga   2700
gatgaagaaa caagtaacaa attaattgat ttattattat ataatgaaaa atatcaaatg   2760
aatcatatta atgataaaaa taaaataat aataataata ataatattaa taatggtaac    2820
gtatctcctt tgtcatctaa atgttcctat acaaatggta ccattatcaa tattatatat   2880
aactttatta atagcaattt ttttacaaca aatatagctg aatctgtatg tgaaataatt   2940
tcaaagtttg ttaaaaatac aaataatatt ggtatagttt tagttaataa tggattaaaa   3000
acttattat tagcatctaa gcatataaca aataaaaga attgtgcttt agcattaagt    3060
gaaatattta tttatacgaa cccgaaactt attcattttt atgaagcata tgattcttta   3120
cctttattaa ttgaacaact aaagagtgat gaagaattat taatctttaa aacgttaatg   3180
gcaataacta atatttaac tattgatgaa atgtagcaa taaagctat gcaattaaat     3240
ttatggtata aatgttttga tattctttca acagaaaatg aatacataaa atctgctagc   3300
```

-continued

```
ttagaatgta tatgcaattt atgttcccaa tcacatgtac atcaatatat ttatgataaa    3360
tatcaaacaa ttatgaaatc aaaaaatgaa tcagataaag atattttatt tgttgatatt    3420
caaataattt attcatttac catggaatat caaaattata aatgtgtttt tgcagcaact    3480
ggagctttag gtatgttgtc atctgatttg cgtttgccat attatttagt tagaactaaa    3540
gggattgatc atattttctc atctttcaat aataccaccg accaaaatat tttattacgt    3600
attttaacat ttttcaacaa cataatgacg tgtgatgata taccggatga tatattaaag    3660
aaaataaaga cttatgtgga gaaaagaag gatttaaatg aagagaatac tcaaatggca    3720
aattttatac tccagtag                                                  3738

<210> SEQ ID NO 4
<211> LENGTH: 1245
<212> TYPE: PRT
<213> ORGANISM: Plasmodium falciparum

<400> SEQUENCE: 4

Met Gln Glu Phe Val Met Asn Ile Leu Ser Lys Glu Lys Ile Gly Lys
1               5                   10                  15

Ile Glu Lys Leu Lys Asn Asp Gly Asn Glu Leu Tyr Arg Asn Lys Lys
            20                  25                  30

Tyr Lys Glu Ala Leu Cys Ile Tyr Asp Asn Ala Val Cys Glu Phe Cys
        35                  40                  45

Gly Gly Ser Gly Asp Ser Leu Lys Ile Lys Glu Met Val Lys Glu Phe
    50                  55                  60

Ser Lys Asn Asp Glu Thr Asn Asn Ile Asn Lys Leu Ser Asp Asp Asn
65                  70                  75                  80

Asn Asn Asn Asn Met Ile Asp Glu Asn Asn Lys Lys Cys Asp Phe Ser
                85                  90                  95

Tyr Ile Cys Glu Ile Gln Asn Leu Phe Ile Lys Ile Cys His Asn Ile
            100                 105                 110

Ser Leu Cys Tyr Tyr Phe Leu Glu Asp Phe Glu Lys Ser Ile Glu Tyr
        115                 120                 125

Cys Leu Tyr Ile Asn Glu Met Asn Asn Asn His Tyr Lys Ser Tyr His
    130                 135                 140

Thr Leu Gly Leu Cys Tyr Glu Lys Leu Lys Asp Tyr Gln Lys Ser Ile
145                 150                 155                 160

His Tyr Phe Asp Arg Cys Lys Ile Val Leu Leu Lys Asn Gln Asn Asn
                165                 170                 175

Lys Asn Lys Asp Asn Asn Asn Lys Ser Glu Ile Asn Arg Ile Asn Glu
            180                 185                 190

Lys Leu Arg Asp Ile Met Lys Ile Ile Asp Gln Asn Lys Asn Asp Pro
        195                 200                 205

Tyr Lys Asn Ile Ser Asn Ile Lys Lys Tyr Leu Leu Asp Glu Asn Thr
    210                 215                 220

Asn Asn Ile Asn Asp Ile Glu Glu Asn Lys Lys Ile Lys Leu Leu
225                 230                 235                 240

His Ser Ile Tyr Asn Gln Lys Phe Tyr Ile Leu Lys Glu Asn Ile
                245                 250                 255

Phe Leu Phe Leu Phe Asp Phe Ile Lys Lys Asn Asn Asp Ile Ser Asn
            260                 265                 270

Tyr Asp Asp Cys Asn Asn Asn Asn Asn Asn Asn Leu Tyr Ser His
        275                 280                 285
```

-continued

```
Asn Ile Asn Ser Leu Leu Leu Glu Lys Thr Ala Ile Tyr Val Ile Tyr
290                 295                 300

Lys Ile Leu Ser Lys Leu Asp Asn Glu His Ile Ile Glu Asn Ser
305                 310                 315                 320

Lys Asp Asp Asn Tyr Asn Lys Asn Arg Asn Ile Cys Ile Asn Lys Leu
                325                 330                 335

Asp Asn Ser Lys Leu Gln Tyr Tyr Asp Leu Asp Tyr Ile Lys Met
        340                 345                 350

Ile Leu Ser Phe Asn Glu Tyr Phe Thr Lys Asp Trp Ile Tyr Asn Tyr
        355                 360                 365

Ile Lys Lys Lys Ile Asn Ile Leu Glu Asn Leu Lys Phe Ser Lys Asp
370                 375                 380

Glu Thr Leu Tyr Lys Glu His Val Asp Ile Leu Ile Tyr Ile Ile Asn
385                 390                 395                 400

Ile Met Lys Tyr Val Tyr Val Ile Asn Asn Asp Tyr Ile Leu Asn Ile
                405                 410                 415

Ile Asn Ser Tyr Tyr Leu Asn Ser Asp Asn Ser Asn Ile Asn Asn Ser
                420                 425                 430

Gly Ile Asn Ala Leu Thr Phe Leu Cys Lys Lys Lys Gln Phe Leu Thr
        435                 440                 445

Gln Asn Ser Lys Asp Asn Arg Lys Lys Lys Asn Asp Leu Leu Glu Met
450                 455                 460

Leu Lys Lys Glu Asn Tyr Leu Asn Ile Gln Asn Asn Ile Gln Asn Asn
465                 470                 475                 480

Asn Asn Asn Asn Asn Tyr Tyr Phe Tyr Lys Asn Glu Phe Ile Glu Phe
                485                 490                 495

His Phe Ser Asp Ser His Lys Tyr Pro Leu Cys Ile Asn Ser Glu Ile
                500                 505                 510

Lys Lys Ile Ile Gln Asn Val Ile Gly Met Tyr Glu His Phe Ser Ser
        515                 520                 525

Ser Ile Glu Tyr Thr Leu Ile Leu Ile Phe Thr Leu Leu His Asp Pro
        530                 535                 540

Gln Arg Pro Lys Glu Lys Asp Ile Glu Met Asn Asp Val Ile Tyr Asp
545                 550                 555                 560

Cys Ile Asp Asn Tyr Phe His His Asn Glu Asn Ile Leu Ile Glu Trp
                565                 570                 575

Phe Val Cys Ile Lys Cys Leu Phe Leu Val Asp Lys Asn Ile Ile Leu
                580                 585                 590

Asn Tyr Leu Ile Gly Lys Thr Glu Tyr Ile Val Lys Ile Leu His Phe
        595                 600                 605

Ile Thr Asn Cys Ile Gly Arg Lys Thr Lys Glu Glu Leu Ser Ile Tyr
610                 615                 620

Ile Asp Val Leu Leu Leu Leu Asn Ile Ser Glu Ile Arg Phe Met
625                 630                 635                 640

Phe Thr Asn Tyr Ile Asp Met Tyr Ile Asn Ile Met Lys Ser Leu Asn
                645                 650                 655

Tyr Asp Gln Cys Phe Leu Lys Leu Leu Leu Gly Thr Phe Lys Leu Tyr
                660                 665                 670

Met His Asn Ile Asp Phe Lys Gln Gln Ile Gln Asp Asn Val Asp Leu
        675                 680                 685

Phe Phe Tyr Ala Lys Glu Ile Leu Lys Gln Phe Leu Leu Thr Tyr Asp
690                 695                 700

Asn Asp Ala Asp Gly Lys Asn Asn Thr Asn Asn Asp Lys Arg Glu Glu
```

```
            705                 710                 715                 720
Asn Glu Glu Gln Thr Ser His Leu Asn Tyr Ser Asn Leu Asn Ser Tyr
                    725                 730                 735
Thr Cys Cys Val Lys Lys Cys Asp Asp Asn Asp Thr Lys Lys Lys Asp
                    740                 745                 750
Ile Ile Asn Gln Lys Lys Asp Glu Lys Asn Lys Lys His Cys Glu Leu
                    755                 760                 765
Val Asp Lys Lys Lys Asp His Thr Tyr Ile His Ser Asn Met Ser
770                 775                 780
Cys Glu Lys Thr Leu Lys Asp Leu Ile Glu Met Leu Phe Tyr Leu Ser
785                 790                 795                 800
Leu His Ile Glu Phe Lys Lys Gln Leu Leu Glu Lys Asn Asn Tyr
                    805                 810                 815
Ile Leu Phe Phe Leu Ile Lys Val Gly His Asp Ile Asn Lys Lys
                    820                 825                 830
Leu Asp Asn Thr Tyr Lys Tyr Ile Tyr Cys Asn Thr Ile Asn Asn Leu
                    835                 840                 845
Ile Leu Thr Lys Asn Asp Glu Lys Ile Lys Arg Arg Glu Ile Asn Lys
850                 855                 860
Thr Asn Leu Ser Asn Phe Asp Asn Glu Gln Ile Glu Ala Leu Glu Gln
865                 870                 875                 880
Phe Tyr Asp Lys Leu Pro Lys Glu Ala Arg Pro Lys Thr Asp Pro Leu
                    885                 890                 895
Tyr Asp Tyr Gly Asp Glu Glu Thr Ser Asn Lys Leu Ile Asp Leu Leu
                    900                 905                 910
Leu Tyr Asn Glu Lys Tyr Gln Met Asn His Ile Asn Asp Lys Asn Lys
                    915                 920                 925
Asn Asn Asn Asn Asn Asn Ile Asn Asn Gly Asn Val Ser Pro Leu
                    930                 935                 940
Ser Ser Lys Cys Ser Tyr Thr Asn Gly Thr Ile Ile Asn Ile Ile Tyr
945                 950                 955                 960
Asn Phe Ile Asn Ser Asn Phe Phe Thr Thr Asn Ile Ala Glu Ser Val
                    965                 970                 975
Cys Glu Ile Ile Ser Lys Phe Val Lys Asn Thr Asn Asn Ile Gly Ile
                    980                 985                 990
Val Leu Val Asn Asn Gly Leu Lys  Thr Leu Leu Leu Ala  Ser Lys His
                    995                 1000                1005
Ile Thr  Asn Lys Lys Asn Cys  Ala Leu Ala Leu Ser  Glu Ile Phe
     1010                1015                1020
Ile Tyr  Thr Asn Pro Lys Leu  Ile His Phe Tyr Glu  Ala Tyr Asp
     1025                1030                1035
Ser Leu  Pro Leu Leu Ile Glu  Gln Leu Lys Ser Asp  Glu Glu Leu
     1040                1045                1050
Leu Ile  Phe Lys Thr Leu Met  Ala Ile Thr Asn Ile  Leu Thr Ile
     1055                1060                1065
Asp Glu  Asn Val Ala Ile Lys  Ala Met Gln Leu Asn  Leu Trp Tyr
     1070                1075                1080
Lys Cys  Phe Asp Ile Leu Ser  Thr Glu Asn Glu Tyr  Ile Lys Ser
     1085                1090                1095
Ala Ser  Leu Glu Cys Ile Cys  Asn Leu Cys Ser Gln  Ser His Val
     1100                1105                1110
His Gln  Tyr Ile Tyr Asp Lys  Tyr Gln Thr Ile Met  Lys Ser Lys
     1115                1120                1125
```

```
Asn Glu Ser Asp Lys Asp Ile Leu Phe Val Asp Ile Gln Ile Ile
    1130                1135                1140

Tyr Ser Phe Thr Met Glu Tyr Gln Asn Tyr Lys Cys Val Phe Ala
    1145                1150                1155

Ala Thr Gly Ala Leu Gly Met Leu Ser Ser Asp Leu Arg Leu Pro
    1160                1165                1170

Tyr Tyr Leu Val Arg Thr Lys Gly Ile Asp His Ile Phe Ser Ser
    1175                1180                1185

Phe Asn Asn Thr Thr Asp Gln Asn Ile Leu Leu Arg Ile Leu Thr
    1190                1195                1200

Phe Phe Asn Asn Ile Met Thr Cys Asp Asp Ile Pro Asp Asp Ile
    1205                1210                1215

Leu Lys Lys Ile Lys Thr Tyr Val Glu Lys Lys Asp Leu Asn
    1220                1225                1230

Glu Glu Asn Thr Gln Met Ala Asn Phe Ile Leu Gln
    1235                1240                1245

<210> SEQ ID NO 5
<211> LENGTH: 615
<212> TYPE: DNA
<213> ORGANISM: Plasmodium falciparum

<400> SEQUENCE: 5
atgaaacaag aatgcaatgt atgttatttt aacttgcctg acccagagtc caccttaggt    60
ccatatgata tgaattaaaa ttatttcact tggggaccag gatttgaata tgaacctgaa   120
ccacaaagaa agccattgtc aattgaagaa agttttgaaa actctgaaga atccgaagaa   180
tcagttgctg acatacaaca acttgaagaa aaagtagatg aaagtgatgt gaggatttat   240
tttaatgaaa agagtagtgg tgggaaaata agtatagaca atgcatctta caatgctcga   300
aagttaggtt tagctccatc aagtatcgat gaaaagaaaa ttaagaatt atatggagat    360 aacttaacat atgaacaata tttagaatat ttgtctatat gtgtccatga taaagataat   420
gtagaagaac ttattaaaat gtttgcacac tttgataata attgtactgg ttacttaact   480
aagagccaaa tgaaaaatat tcttacaact tggggtgatg cattaacgga tcaagaagcc   540
atagatgctc ttaatgcctt ttcatcagaa gataacattg attacaaatt attctgtgaa   600
gatatattac aataa                                                    615

<210> SEQ ID NO 6
<211> LENGTH: 204
<212> TYPE: PRT
<213> ORGANISM: Plasmodium falciparum

<400> SEQUENCE: 6

Met Lys Gln Glu Cys Asn Val Cys Tyr Phe Asn Leu Pro Asp Pro Glu
1               5                   10                  15

Ser Thr Leu Gly Pro Tyr Asp Asn Glu Leu Asn Tyr Phe Thr Trp Gly
            20                  25                  30

Pro Gly Phe Glu Tyr Glu Pro Glu Pro Gln Arg Lys Pro Leu Ser Ile
        35                  40                  45

Glu Glu Ser Phe Glu Asn Ser Glu Glu Ser Glu Ser Val Ala Asp
    50                  55                  60

Ile Gln Gln Leu Glu Glu Lys Val Asp Glu Ser Asp Val Arg Ile Tyr
65                  70                  75                  80

Phe Asn Glu Lys Ser Ser Gly Gly Lys Ile Ser Ile Asp Asn Ala Ser
```

```
                    85                  90                  95
Tyr Asn Ala Arg Lys Leu Gly Leu Ala Pro Ser Ser Ile Asp Glu Lys
                100                 105                 110

Lys Ile Lys Glu Leu Tyr Gly Asp Asn Leu Thr Tyr Glu Gln Tyr Leu
            115                 120                 125

Glu Tyr Leu Ser Ile Cys Val His Asp Lys Asp Asn Val Glu Glu Leu
        130                 135                 140

Ile Lys Met Phe Ala His Phe Asp Asn Asn Cys Thr Gly Tyr Leu Thr
145                 150                 155                 160

Lys Ser Gln Met Lys Asn Ile Leu Thr Thr Trp Gly Asp Ala Leu Thr
                165                 170                 175

Asp Gln Glu Ala Ile Asp Ala Leu Asn Ala Phe Ser Ser Glu Asp Asn
            180                 185                 190

Ile Asp Tyr Lys Leu Phe Cys Glu Asp Ile Leu Gln
        195                 200

<210> SEQ ID NO 7
<211> LENGTH: 411
<212> TYPE: DNA
<213> ORGANISM: Plasmodium falciparum

<400> SEQUENCE: 7
atgcgcatag tagataagca aataaaagaa tccttcccttt tagcagacag aaattttgat      60
gggcatattt catcgaatga attattatac gctttaagat tccttggagt ggaatctgat     120
tattctctaa tggaaaataa agtgggggca acttattcaa tgaatgatta tgttaaaata     180
gctaagaaac atttaggtgc acacacacca aaagaaagaa ttacaaattc cttaaaaaaa     240
atggataaaa ataacaatgg aactatatca gttgacgcat tagttcattt agttatgact     300
atgagtgata ttttaacaga aaatgattac agaaaattta aaaaatttgt tgatcctgaa     360
agcagaaata tcataccgtt acatgtattt gtagaaaaaa tactttcgta a              411

<210> SEQ ID NO 8
<211> LENGTH: 136
<212> TYPE: PRT
<213> ORGANISM: Plasmodium falciparum

<400> SEQUENCE: 8

Met Arg Ile Val Asp Lys Gln Ile Lys Glu Ser Phe Leu Leu Ala Asp
1               5                   10                  15

Arg Asn Phe Asp Gly His Ile Ser Ser Asn Glu Leu Leu Tyr Ala Leu
            20                  25                  30

Arg Phe Leu Gly Val Glu Ser Asp Tyr Ser Leu Met Glu Asn Lys Ser
        35                  40                  45

Gly Ala Thr Tyr Ser Met Asn Asp Tyr Val Lys Ile Ala Lys Lys His
    50                  55                  60

Leu Gly Ala His Thr Pro Lys Glu Arg Ile Thr Asn Ser Leu Lys Lys
65                  70                  75                  80

Met Asp Lys Asn Asn Asn Gly Thr Ile Ser Val Asp Ala Leu Val His
                85                  90                  95

Leu Val Met Thr Met Ser Asp Ile Leu Thr Glu Asn Asp Tyr Arg Lys
                100                 105                 110

Phe Lys Lys Phe Val Asp Pro Glu Ser Arg Asn Ile Ile Pro Leu His
            115                 120                 125

Val Phe Val Glu Lys Ile Leu Ser
        130                 135
```

<210> SEQ ID NO 9
<211> LENGTH: 411
<212> TYPE: DNA
<213> ORGANISM: Plasmodium falciparum

<400> SEQUENCE: 9

```
atgcgcatag tagataagca aataaaagaa tccttccttt tagcagacag aaattttgat      60
gggcatattt catcgaatga attattatac gctttaagat tccttggagt ggaatctgat     120
tattctctaa tggaaaataa agtggggca acttattcaa tgaatgatta tgttaaaata     180
gctaagaaac atttaggtgc acacacacca aaagaaagaa ttacaaattc cttaaaaaaa     240
atggataaaa ataacaatgg aactatatca gttgacgcat tagttcattt agttatgact     300
atgagtgata ttttaacaga aaatgattac agaaaattta aaaaatttgt tgatcctgaa     360
agcagaaata tcataccgtt acatgtattt gtagaaaaaa tactttcgta a              411
```

<210> SEQ ID NO 10
<211> LENGTH: 149
<212> TYPE: PRT
<213> ORGANISM: Plasmodium falciparum

<400> SEQUENCE: 10

```
Met Ala Asp Lys Leu Thr Glu Glu Gln Ile Ser Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Ile Asp Thr Asp Gly Asn Gly Thr Ile
    50                  55                  60

Asp Phe Pro Glu Phe Leu Thr Leu Met Ala Arg Lys Leu Lys Asp Thr
65                  70                  75                  80

Asp Thr Glu Glu Glu Leu Ile Glu Ala Phe Arg Val Phe Asp Arg Asp
                85                  90                  95

Gly Asp Gly Tyr Ile Ser Ala Asp Glu Leu Arg His Val Met Thr Asn
            100                 105                 110

Leu Gly Glu Lys Leu Thr Asn Glu Glu Val Asp Glu Met Ile Arg Glu
        115                 120                 125

Ala Asp Ile Asp Gly Asp Gly Gln Ile Asn Tyr Glu Glu Phe Val Lys
    130                 135                 140

Met Met Ile Ala Lys
145
```

<210> SEQ ID NO 11
<211> LENGTH: 3490
<212> TYPE: DNA
<213> ORGANISM: Toxoplasma gondii

<400> SEQUENCE: 11

```
atggaggatt tgtcaaacgc tacgttagct cgcctccagg cgctgaaaga ggaaggaaat      60
gcggagttta agcggggcaa gttcgagtcc gcgatcgaag cgtattcgcg atgcctggct     120
gatgcctcag acactctgga taagaaccca gacgtcctgg aggcgcgtg tgcggccagc     180
ctctcttcct ccgactctca ggtcgcagaa cctcgcaaag aaagccctgc cattctgaag     240
cgcgtggccg aactgaaggc gcaaatcctg tgcaatcgcg ccctgtgcta ccagcggacg     300
```

-continued

```
aagcagttcg cggcggccga ggcggactgt acgcgcgcca tcgctctcca tccggcctac    360
gtgaagagtt actaccgacg cgcgttgcg ctggacgccc agggaaggcg taaagagtgt    420
gtggaggatc tgcagacgtg tctgcgcctg cagcctggaa acaaggaggc gcaggagatg    480
ctcgcggggg ttcgcgacaa ggtgatgaag gaggaggaga cgcgcgtcga agagcagctg    540
cccgagaacc tgctgactgc cggcctcaac gacgtgctca cggcctcgaa gcgagtcgcc    600
tcccttcgcc aactcggcgc cttcgttcag gagcggaagc tgcggcgtca gttccttcga    660
gacggcggtc tgcgacgcgt tgccgttgcc ctgaagagcc aaatggacag tgagctcgag    720
ggcaacggcc agcctcaccg gtcgctcgag tctcttccgg agaccacggc ctcggacccc    780
gtggcttctg aagagagcaa agcagcgca gacgccgttc tccccgtcag cgtcgaagca    840
gcgtgctggg agttgctctt gtccgtcgtc cagcagcacc aggcggacga cgaagacgac    900
gcaaacaagg ctctgcagac ctctgtggag gccgtgaacg cgccgcttca ggtcgacgcg    960
ccggtcctcg agtgccgcca agctctctcc ggcctctgga ctcccaacga cttcctcgtg   1020
cgtctgcggc agctcctgcg tgcaggcgtc gcgcgctccg acggcctcgc tgcgaccgcc   1080
gcgaacgaag aagctgggaa actgcggacc gtctggcgcg gcgaagcctg tgacaggctc   1140
ctgcgcacga tgggctgcgt ggtgcagctg caggcggcgc agttcgacga ggacgcctcc   1200
ttcctcgagg cctgcgccgc cggcctggag tgtatagact cccgagaggt ccagcgcgcg   1260
gctgtcgcgg cgcttgtggg cgtcgcagac gcgcggcgcc gcctgggcgg cagagttgcg   1320
gccgtgcggc tgcggcatgg actcgaaaag tgtctcgagg acgccttgca ggtcgtctcg   1380
gacgcagaac acgaactcgc gggcgaagac gctcgctctc agctggccac cgcgtccaag   1440
aaaagcgaca gacttgaagc ggtgagtcgt ctacagggcc agaccgagta cttgatcatc   1500
acgctaatcg ctcttctcgc agacaaagac gcggcaagg aggagcctcc cgacatgagt   1560
cgcctggtcg accagctgct gtcgccgtac ttccggccgt gcgcagaccc cgaggagagc   1620
gtcgtcaccc tgacagttgg gttgaaggcg ctgcgtttga ttctgactgc ggcgcgcgaa   1680
gttgcgcggg cgtacctgat tccgcgtct tcgattctcc cctacctcct ggctgccgcc   1740
gcgggcggtg taggtacagc gcagagcggg gccgcgggga ctgcagcgca tcggcgccag   1800
caggaagctg cattggaggt cttgctggcc tgcatggatt tcccagaact gcgtgcgacg   1860
ttgctcgagg cgaacgcggt gccggtcttc gcgaaagtgt gcagcgagag cgcgaatgtc   1920
gggtgttgga tgagggcgcg tctggcggct gcactcgctc ggctgtctgt tcacgacgag   1980
gacgtccgga tccaggtatt tgactcgatc gacttctacg acgtcctcga tgtgctcgtg   2040
tcggaaattc gcgcggcagg tggcgacggc cgccaggttg cggagccgag caccgaagcc   2100
aagaacgcgc agaaaggcca gccgatggct gttggagagg agacgtttcg gtctctgctt   2160
gagatcttct tcttcctcag tctccacggc gacttcaaag cgcggctcgt gaccgggaag   2220
aagggcgcga gggtgctgcg gacgcttctg caagttgcga acggggctgg gaaaaaaggc   2280
gcttcttcga gtctgacgcg gtatctcctt ctccagagtc tgtgcaacat catgcggtcg   2340
cgagaagacc gacagagaca gcggagaagg aaaggcgagg tcggaagtcc actcgcagac   2400
gttgacgacg agcagctgca gcagctcgag gagttgttca agaagctgcc ggaaggcgcg   2460
aagccggctg cgaacggcga ggtcgatctc ggagacaagg ccctcgcaac gcagctccgc   2520
gacatgctcc tagacctgaa cgtggttcat gcaatcgccg tgaacgtctg cgcgaccccg   2580
ccgccgtctt ccaacgtcct gtgtgccgcg gcgcaggcgc tgaagttcct ttgcgaggac   2640
tcgcggcacc gaggcagagc tgttcaggag gggggcattc ggacgctctt ggtggccgcg   2700
```

```
agtgggctcg aggaattccc agacgaccag aggaacgcgc gacaagctgc ggcgcagctc    2760
tgcatcacca ccaacccggc cctgttctct taccgcgaga gcttagacct cgtccctgc     2820 ctcgcgccgc ttctcaagga ccgccacgag ttgctgcagt acgaaggcgc gctcgcgttg    2880
acgaatctct gtgccctcag cgaggaggtc cgcatgcgtg cgtggctcgg cggcgtctgg    2940
gaaggcttcg aggacctcat gttcggggag aacgagttgc tgcgcgccgc ggggttggag    3000
ggatggtgca acttgtcggc ctcgccgacg gtccaaacgg agatcgggaa gaagatggaa    3060
cgtttcgcgg cggagaaaca agaagttcaa gatatgaaac tcttgctcgc gttcacgcgg    3120
gaaacgaaca accctcgtgc gcagtccgcc gccgtcgcgg ctctcgcgat gcttctcgcg    3180
aacgagaagg tcgcacgctg tcttccggcc tacagcctct ttggcaacct cgctttgagc    3240
ctcgaggaag cgaaggccga gcaggaagct ctgatcgtga ggtgcgtctc cgccctctac    3300
aacgtctgga tcgagttgag cagttctgag gcgggagctg agacccgcat gcagatcgtg    3360
aaaaccctgc agagaaacca acaaaaactc actggagacg cacaaacacct cgccaaggaa    3420 gtcctcacgg cagaactctc ccaagcaaac acacacacga aagaatccac cccagactca    3480
agctaacggc                                                            3490
```

<210> SEQ ID NO 12
<211> LENGTH: 1161
<212> TYPE: PRT
<213> ORGANISM: Toxoplasma gondii

<400> SEQUENCE: 12

```
Met Glu Asp Leu Ser Asn Ala Thr Leu Ala Arg Leu Gln Ala Leu Lys
1               5                   10                  15

Glu Glu Gly Asn Ala Glu Phe Lys Arg Gly Lys Phe Glu Ser Ala Ile
            20                  25                  30

Glu Ala Tyr Ser Arg Cys Leu Ala Asp Ala Ser Asp Thr Leu Asp Lys
        35                  40                  45

Glu Pro Asp Val Leu Gly Gly Ala Cys Ala Ala Ser Leu Ser Ser Ser
    50                  55                  60

Asp Ser Gln Val Ala Glu Pro Arg Lys Glu Ser Pro Ala Ile Leu Lys
65                  70                  75                  80

Arg Val Ala Glu Leu Lys Ala Gln Ile Leu Cys Asn Arg Ala Leu Cys
                85                  90                  95

Tyr Gln Arg Thr Lys Gln Phe Ala Ala Ala Glu Ala Asp Cys Thr Arg
            100                 105                 110

Ala Ile Ala Leu His Pro Ala Tyr Val Lys Ser Tyr Tyr Arg Arg Ala
        115                 120                 125

Val Ala Leu Asp Ala Gln Gly Arg Arg Lys Glu Cys Val Glu Asp Leu
    130                 135                 140

Gln Thr Cys Leu Arg Leu Gln Pro Gly Asn Lys Glu Ala Gln Glu Met
145                 150                 155                 160

Leu Ala Gly Val Arg Asp Lys Val Met Lys Glu Glu Thr Arg Val
                165                 170                 175

Glu Glu Gln Leu Pro Glu Asn Leu Leu Thr Ala Gly Leu Asn Asp Val
            180                 185                 190

Leu Thr Ala Ser Lys Arg Val Ala Ser Leu Arg Gln Leu Gly Ala Phe
        195                 200                 205

Val Gln Glu Arg Lys Leu Arg Arg Gln Phe Leu Arg Asp Gly Gly Leu
    210                 215                 220
```

```
Arg Arg Val Ala Val Ala Leu Lys Ser Gln Met Asp Ser Glu Leu Glu
225                 230                 235                 240

Gly Asn Gly Gln Pro His Arg Ser Leu Glu Ser Leu Pro Glu Thr Thr
        245                 250                 255

Ala Ser Asp Pro Val Ala Ser Glu Glu Ser Lys Ser Ser Ala Asp Ala
            260                 265                 270

Val Leu Pro Val Ser Val Glu Ala Ala Cys Trp Glu Leu Leu Leu Ser
        275                 280                 285

Val Val Gln Gln His Gln Ala Asp Asp Glu Asp Ala Asn Lys Ala
290                 295                 300

Leu Gln Thr Ser Val Glu Ala Val Asn Ala Pro Leu Gln Val Asp Ala
305                 310                 315                 320

Pro Val Leu Glu Cys Arg Gln Ala Leu Ser Gly Leu Trp Thr Pro Asn
                325                 330                 335

Asp Phe Leu Val Arg Leu Arg Gln Leu Leu Arg Ala Gly Val Ala Arg
                340                 345                 350

Ser Asp Gly Leu Ala Ala Thr Ala Ala Asn Glu Glu Ala Gly Lys Leu
            355                 360                 365

Arg Thr Val Trp Arg Gly Glu Ala Cys Asp Arg Leu Leu Arg Thr Met
370                 375                 380

Gly Cys Val Val Gln Leu Gln Ala Ala Gln Phe Asp Glu Asp Ala Ser
385                 390                 395                 400

Phe Leu Glu Ala Cys Ala Ala Gly Leu Glu Cys Ile Asp Ser Arg Glu
                405                 410                 415

Val Gln Arg Ala Ala Val Ala Ala Leu Val Gly Val Ala Asp Ala Arg
        420                 425                 430

Arg Arg Leu Gly Gly Arg Val Ala Ala Arg Leu Arg His Gly Leu
        435                 440                 445

Glu Lys Cys Leu Glu Asp Ala Leu Gln Val Val Ser Asp Ala Glu His
450                 455                 460

Glu Leu Ala Gly Glu Asp Ala Arg Ser Gln Leu Ala Thr Ala Ser Lys
465                 470                 475                 480

Lys Ser Asp Arg Leu Glu Ala Val Ser Arg Leu Gln Gly Gln Thr Glu
            485                 490                 495

Tyr Leu Ile Ile Thr Leu Ile Ala Leu Leu Ala Asp Lys Asp Arg Gly
            500                 505                 510

Lys Glu Glu Pro Pro Asp Met Ser Arg Leu Val Asp Gln Leu Leu Ser
        515                 520                 525

Pro Tyr Phe Arg Pro Cys Ala Asp Pro Glu Glu Ser Val Val Thr Leu
530                 535                 540

Thr Val Gly Leu Lys Ala Leu Arg Leu Ile Leu Thr Ala Ala Arg Glu
545                 550                 555                 560

Val Ala Arg Ala Tyr Leu Ile Ser Ala Ser Ile Leu Pro Tyr Leu
            565                 570                 575

Leu Ala Ala Ala Gly Gly Val Gly Thr Ala Gln Ser Gly Ala Ala
            580                 585                 590

Gly Thr Ala Ala His Arg Arg Gln Gln Glu Ala Ala Leu Glu Val Leu
        595                 600                 605

Leu Ala Cys Met Asp Phe Pro Glu Leu Arg Ala Thr Leu Leu Glu Ala
            610                 615                 620

Asn Ala Val Pro Val Phe Ala Lys Val Cys Ser Glu Ser Ala Asn Val
625                 630                 635                 640

Gly Cys Trp Met Arg Ala Arg Leu Ala Ala Ala Leu Ala Arg Leu Ser
```

```
            645                 650                 655
Val His Asp Glu Asp Val Arg Ile Gln Val Phe Asp Ser Ile Asp Phe
                660                 665                 670

Tyr Asp Val Leu Asp Val Leu Val Ser Glu Ile Arg Ala Ala Gly Gly
            675                 680                 685

Asp Gly Arg Gln Val Ala Glu Pro Ser Thr Glu Ala Lys Asn Ala Gln
        690                 695                 700

Lys Gly Gln Pro Met Ala Val Gly Glu Thr Phe Arg Ser Leu Leu
705                 710                 715                 720

Glu Ile Phe Phe Phe Leu Ser Leu His Gly Asp Phe Lys Ala Arg Leu
                725                 730                 735

Val Thr Gly Lys Lys Gly Ala Arg Val Leu Arg Thr Leu Leu Gln Val
            740                 745                 750

Ala Asn Gly Ala Gly Lys Lys Gly Ala Ser Ser Leu Thr Arg Tyr
            755                 760                 765

Leu Leu Leu Gln Ser Leu Cys Asn Ile Met Arg Ser Arg Glu Asp Arg
        770                 775                 780

Gln Arg Gln Arg Arg Lys Gly Glu Val Gly Ser Pro Leu Ala Asp
785                 790                 795                 800

Val Asp Asp Glu Gln Leu Gln Gln Leu Glu Glu Leu Phe Lys Lys Leu
                805                 810                 815

Pro Glu Gly Ala Lys Pro Ala Ala Asn Gly Glu Val Asp Leu Gly Asp
            820                 825                 830

Lys Ala Leu Ala Thr Gln Leu Arg Asp Met Leu Leu Asp Leu Asn Val
            835                 840                 845

Val His Ala Ile Ala Val Asn Val Cys Ala Thr Pro Pro Ser Ser
850                 855                 860

Asn Val Leu Cys Ala Ala Ala Gln Ala Leu Lys Phe Leu Cys Glu Asp
865                 870                 875                 880

Ser Arg His Arg Gly Arg Ala Val Gln Glu Gly Gly Ile Arg Thr Leu
            885                 890                 895

Leu Val Ala Ala Ser Gly Leu Glu Glu Phe Pro Asp Asp Gln Arg Asn
        900                 905                 910

Ala Arg Gln Ala Ala Ala Gln Leu Cys Ile Thr Thr Asn Pro Ala Leu
    915                 920                 925

Phe Ser Tyr Arg Glu Ser Leu Asp Leu Val Pro Cys Leu Ala Pro Leu
        930                 935                 940

Leu Lys Asp Arg His Glu Leu Leu Gln Tyr Glu Gly Ala Leu Ala Leu
945                 950                 955                 960

Thr Asn Leu Cys Ala Leu Ser Glu Glu Val Arg Met Arg Ala Trp Leu
                965                 970                 975

Gly Gly Val Trp Glu Gly Phe Glu Asp Leu Met Phe Gly Glu Asn Glu
            980                 985                 990

Leu Leu Arg Ala Ala Gly Leu Glu  Gly Trp Cys Asn Leu  Ser Ala Ser
        995                 1000                1005

Pro Thr  Val Gln Thr Glu Ile  Gly Lys Lys Met Glu  Arg Phe Ala
    1010                1015                1020

Ala Glu  Lys Gln Glu Val Gln  Asp Met Lys Leu Leu  Leu Ala Phe
    1025                1030                1035

Thr Arg  Glu Thr Asn Asn Pro  Arg Ala Gln Ser Ala  Ala Val Ala
    1040                1045                1050

Ala Leu  Ala Met Leu Leu Ala  Asn Glu Lys Val Ala  Arg Cys Leu
    1055                1060                1065
```

```
Pro Ala Tyr Ser Leu Phe Gly Asn Leu Ala Leu Ser Leu Glu Glu
    1070            1075                1080

Ala Lys Ala Glu Gln Glu Ala Leu Ile Val Arg Cys Val Ser Ala
    1085            1090                1095

Leu Tyr Asn Val Trp Ile Glu Leu Ser Ser Ser Glu Ala Gly Ala
    1100            1105                1110

Glu Thr Arg Met Gln Ile Val Lys Thr Leu Gln Arg Asn Gln Gln
    1115            1120                1125

Lys Leu Thr Gly Asp Ala Gln His Leu Ala Lys Glu Val Leu Thr
    1130            1135                1140

Ala Glu Leu Ser Gln Ala Asn Thr His Thr Lys Glu Ser Thr Pro
    1145            1150                1155

Asp Ser Ser
    1160

<210> SEQ ID NO 13
<211> LENGTH: 3012
<212> TYPE: DNA
<213> ORGANISM: Toxoplasma gondii

<400> SEQUENCE: 13
```

| | | | | | |
|---|---|---|---|---|---|
| atgggactcg | cggggttcg | cgacaaggtg | atgaaggagg | aggagacgcg | cgtcgaagag | 60 |
| cagctgcccg | agaacctgct | gactgccggc | ctcaacgacg | tgctcacggc | ctcgaagcga | 120 |
| gtcgcctccc | ttcgccaact | cggcgccttc | gttcaggagc | ggaagctgcg | gcgtcagttc | 180 |
| cttcgagacg | gcggtctgcg | acgcgttgcc | gttgccctga | gagccaaat | ggacagtgag | 240 |
| ctcgagggca | acggccagcc | tcaccggtcg | ctcgagtctc | ttccggagac | cacggcctcg | 300 |
| gaccccgtgg | cttctgaaga | gagcaaaagc | agcgcagacg | ccgttctccc | cgtcagcgtc | 360 |
| gaagcagcgt | gctgggagtt | gctcttgtcc | gtcgtccagc | agcaccaggc | ggacgacgaa | 420 |
| gacgacgcaa | acaaggctct | gcagacctct | gtggaggccg | tgaacgcgcc | gcttcaggtc | 480 |
| gacgcgccgg | tcctcgagtg | ccgccaagct | ctctccggcc | tctggactcc | caacgacttc | 540 |
| ctcgtgcgtc | tgcggcagct | cctgcgtgca | ggcgtcgcgc | gctccgacgg | cctcgctgcg | 600 |
| accgccgcga | acgaagaagc | tgggaaactg | cggaccgtct | ggcgcggcga | agcctgtgac | 660 |
| aggtccctgc | gcacgatggg | ctgcgtggtg | cagctgcagg | cggcgcagtt | cgacgaggac | 720 |
| gcctccttcc | tcgaggcctg | cgccgccggc | ctggagtgta | tagactcccg | agaggtccag | 780 |
| cgcgcggctg | tcgcggcgct | tgtgggcgtc | gcagacgcgc | ggcgccgcct | gggcggcaga | 840 |
| gttgcggccg | tgcggctgcg | gcatggactc | gaaaagtgtc | tcgaggacgc | cttgcaggtc | 900 |
| gtctcggacg | cagaacacga | actcgcgggc | gaagacgctc | gctctcagct | ggccaccgcg | 960 |
| tccaagaaaa | gcgacagact | tgaagcggtg | agtcgtctac | agggccagac | cgagtacttg | 1020 |
| atcatcacgc | taatcgctct | tctcgcagac | aaagaccgcg | gcaaggagga | gcctcccgac | 1080 |
| atgagtcgcc | tggtcgacca | gctgctgtcg | ccgtacttcc | ggccgtgcgc | agaccccgag | 1140 |
| gagagcgtcg | tcaccctgac | agttgggttg | aaggcgctgc | gtttgattct | gactgcggcg | 1200 |
| cgcgaagttg | cgcgggcgta | cctgatttcc | cgtgtcttcg | attctccccta | cctcctggct | 1260 |
| gccgccgcgg | gcggtgtagg | tacagcgcag | agcggggccg | cggggactgc | agcgcatcgg | 1320 |
| cgccagcagg | aagctgcatt | ggaggtcttg | ctggcctgca | tggatttccc | agaactgcgt | 1380 |
| gcgacgttgc | tcgaggcgaa | cgcggtgccg | gtcttcgcga | aagtgtgcag | cgagagcgcg | 1440 |
| aatgtcgggt | gttggatgag | ggcgcgtctg | gcggctgcac | tcgctcggct | gtctgttcac | 1500 |

-continued

```
gacgaggacg tccggatcca ggtatttgac tcgatcgact tctacgacgt cctcgatgtg   1560
ctcgtgtcgg aaattcgcgc ggcaggtggc gacggccgcc aggttgcgga gccgagcacc   1620
gaagccaaga acgcgcagaa aggccagccg atggctgttg gagaggagac gtttcggtct   1680
ctgcttgaga tcttcttctt cctcagtctc cacggcgact tcaaagcgcg gctcgtgacc   1740
gggaagaagg gcgcgagggt gctgcggacg cttctgcaag ttgcgaacgg ggctgggaaa   1800
aaaggcgctt cttcgagtct gacgcggtat ctccttctcc agagtctgtg caacatcatg   1860
cggtcgcgag aagaccgaca gagacagcgg agaaggaaag gcgaggtcgg aagtccactc   1920
gcagacgttg acgacgagca gctgcagcag ctcgaggagt tgttcaagaa gctgccggaa   1980
ggcgcgaagc cggctgcgaa cggcgaggtc gatctcggag acaaggccct cgcaacgcag   2040
ctccgcgaca tgctcctaga cctgaacgtg gttcatgcaa tcgccgtgaa cgtctgcgcg   2100
accccgccgc cgtcttccaa cgtcctgtgt gccgcggcgc aggcgctgaa gttcctttgc   2160
gaggactcgc ggcaccgagg cagagctgtt caggaggggg gcattcggac gctcttggtg   2220
gccgcgagtg ggctcgagga attcccagac gaccagagga acgcgcgaca agctgcggcg   2280
cagctctgca tcaccaccaa cccggccctg ttctcttacc gcgagagctt agacctcgtc   2340
ccctgcctcg cgccgcttct caaggaccgc cacgagttgc tgcagtacga aggcgcgctc   2400
gcgttgacga atctctgtgc cctcagcgag gaggtccgca tgcgtgcgtg gctcggcggc   2460
gtctgggaag gcttcgagga cctcatgttc ggggagaacg agttgctgcg cgccgcgggg   2520
ttggagggat ggtgcaactt gtcggcctcg ccgacggtcc aaacggagat cgggaagaag   2580
atggaacgtt tcgcggcgga gaaacaagaa gttcaagata tgaaactctt gctcgcgttc   2640
acgcgggaaa cgaacaaccc tcgtgcgcag tccgccgccg tcgcggctct cgcgatgctt   2700
ctcgcgaacg agaaggtcgc acgctgtctt ccggcctaca gcctctttgg caacctcgct   2760
ttgagcctcg aggaagcgaa ggccgagcag gaagctctga tcgtgaggtg cgtctccgcc   2820
ctctacaacg tctggatcga gttgagcagt tctgaggcgg gagctgagac ccgcatgcag   2880
atcgtgaaaa ccctgcagag aaaccaacaa aaactcactg gagacgcaca acacctcgcc   2940
aaggaagtcc tcacggcaga actctcccaa gcaaacacac acacgaaaga atccacccca   3000
gactcaagct aa                                                       3012

<210> SEQ ID NO 14
<211> LENGTH: 1003
<212> TYPE: PRT
<213> ORGANISM: Toxoplasma gondii

<400> SEQUENCE: 14

Met Gly Leu Ala Gly Val Arg Asp Lys Val Met Lys Glu Glu Glu Thr
1               5                   10                  15

Arg Val Glu Glu Gln Leu Pro Glu Asn Leu Leu Thr Ala Gly Leu Asn
            20                  25                  30

Asp Val Leu Thr Ala Ser Lys Arg Val Ala Ser Leu Arg Gln Leu Gly
        35                  40                  45

Ala Phe Val Gln Glu Arg Lys Leu Arg Arg Gln Phe Leu Arg Asp Gly
    50                  55                  60

Gly Leu Arg Arg Val Ala Val Ala Leu Lys Ser Gln Met Asp Ser Glu
65                  70                  75                  80

Leu Glu Gly Asn Gly Gln Pro His Arg Ser Leu Glu Ser Leu Pro Glu
                85                  90                  95
```

```
Thr Thr Ala Ser Asp Pro Val Ala Ser Glu Ser Lys Ser Ser Ala
            100                 105                 110

Asp Ala Val Leu Pro Val Ser Val Glu Ala Ala Cys Trp Glu Leu Leu
        115                 120                 125

Leu Ser Val Val Gln Gln His Gln Ala Asp Asp Glu Asp Asp Ala Asn
    130                 135                 140

Lys Ala Leu Gln Thr Ser Val Glu Ala Val Asn Ala Pro Leu Gln Val
145                 150                 155                 160

Asp Ala Pro Val Leu Glu Cys Arg Gln Ala Leu Ser Gly Leu Trp Thr
                165                 170                 175

Pro Asn Asp Phe Leu Val Arg Leu Arg Gln Leu Leu Arg Ala Gly Val
            180                 185                 190

Ala Arg Ser Asp Gly Leu Ala Ala Thr Ala Ala Asn Glu Glu Ala Gly
        195                 200                 205

Lys Leu Arg Thr Val Trp Arg Gly Glu Ala Cys Asp Arg Leu Leu Arg
    210                 215                 220

Thr Met Gly Cys Val Val Gln Leu Gln Ala Ala Gln Phe Asp Glu Asp
225                 230                 235                 240

Ala Ser Phe Leu Glu Ala Cys Ala Ala Gly Leu Glu Cys Ile Asp Ser
                245                 250                 255

Arg Glu Val Gln Arg Ala Ala Val Ala Ala Leu Val Gly Val Ala Asp
            260                 265                 270

Ala Arg Arg Arg Leu Gly Gly Arg Val Ala Ala Val Arg Leu Arg His
        275                 280                 285

Gly Leu Glu Lys Cys Leu Glu Asp Ala Leu Gln Val Val Ser Asp Ala
    290                 295                 300

Glu His Glu Leu Ala Gly Glu Asp Ala Arg Ser Gln Leu Ala Thr Ala
305                 310                 315                 320

Ser Lys Lys Ser Asp Arg Leu Glu Ala Val Ser Arg Leu Gln Gly Gln
                325                 330                 335

Thr Glu Tyr Leu Ile Ile Thr Leu Ile Ala Leu Leu Ala Asp Lys Asp
            340                 345                 350

Arg Gly Lys Glu Glu Pro Pro Asp Met Ser Arg Leu Val Asp Gln Leu
        355                 360                 365

Leu Ser Pro Tyr Phe Arg Pro Cys Ala Asp Pro Glu Glu Ser Val Val
    370                 375                 380

Thr Leu Thr Val Gly Leu Lys Ala Leu Arg Leu Ile Leu Thr Ala Ala
385                 390                 395                 400

Arg Glu Val Ala Arg Ala Tyr Leu Ile Ser Ala Ser Ile Leu Pro
                405                 410                 415

Tyr Leu Leu Ala Ala Ala Gly Gly Val Gly Thr Ala Gln Ser Gly
            420                 425                 430

Ala Ala Gly Thr Ala Ala His Arg Arg Gln Gln Glu Ala Ala Leu Glu
        435                 440                 445

Val Leu Leu Ala Cys Met Asp Phe Pro Glu Leu Arg Ala Thr Leu Leu
    450                 455                 460

Glu Ala Asn Ala Val Pro Val Phe Ala Lys Val Cys Ser Glu Ser Ala
465                 470                 475                 480

Asn Val Gly Cys Trp Met Arg Ala Arg Leu Ala Ala Ala Leu Ala Arg
                485                 490                 495

Leu Ser Val His Asp Glu Asp Val Arg Ile Gln Val Phe Asp Ser Ile
            500                 505                 510

Asp Phe Tyr Asp Val Leu Asp Val Leu Val Ser Glu Ile Arg Ala Ala
```

```
            515                 520                 525
Gly Gly Asp Gly Arg Gln Val Ala Glu Pro Ser Thr Glu Ala Lys Asn
530                 535                 540

Ala Gln Lys Gly Gln Pro Met Ala Val Gly Glu Thr Phe Arg Ser
545                 550                 555                 560

Leu Leu Glu Ile Phe Phe Leu Ser Leu His Gly Asp Phe Lys Ala
                    565                 570                 575

Arg Leu Val Thr Gly Lys Lys Gly Ala Arg Val Leu Arg Thr Leu Leu
                580                 585                 590

Gln Val Ala Asn Gly Ala Gly Lys Lys Gly Ala Ser Ser Ser Leu Thr
                595                 600                 605

Arg Tyr Leu Leu Leu Gln Ser Leu Cys Asn Ile Met Arg Ser Arg Glu
        610                 615                 620

Asp Arg Gln Arg Gln Arg Arg Lys Gly Val Gly Ser Pro Leu
625                 630                 635                 640

Ala Asp Val Asp Asp Glu Gln Leu Gln Gln Leu Glu Glu Leu Phe Lys
                    645                 650                 655

Lys Leu Pro Glu Gly Ala Lys Pro Ala Ala Asn Gly Glu Val Asp Leu
                660                 665                 670

Gly Asp Lys Ala Leu Ala Thr Gln Leu Arg Asp Met Leu Leu Asp Leu
            675                 680                 685

Asn Val Val His Ala Ile Ala Val Asn Val Cys Ala Thr Pro Pro Pro
690                 695                 700

Ser Ser Asn Val Leu Cys Ala Ala Ala Gln Ala Leu Lys Phe Leu Cys
705                 710                 715                 720

Glu Asp Ser Arg His Arg Gly Arg Ala Val Gln Gly Gly Ile Arg
                    725                 730                 735

Thr Leu Leu Val Ala Ala Ser Gly Leu Glu Glu Phe Pro Asp Asp Gln
                740                 745                 750

Arg Asn Ala Arg Gln Ala Ala Gln Leu Cys Ile Thr Thr Asn Pro
                755                 760                 765

Ala Leu Phe Ser Tyr Arg Glu Ser Leu Asp Leu Val Pro Cys Leu Ala
    770                 775                 780

Pro Leu Leu Lys Asp Arg His Glu Leu Leu Gln Tyr Glu Gly Ala Leu
785                 790                 795                 800

Ala Leu Thr Asn Leu Cys Ala Leu Ser Glu Glu Val Arg Met Arg Ala
                    805                 810                 815

Trp Leu Gly Gly Val Trp Glu Gly Phe Glu Asp Leu Met Phe Gly Glu
                820                 825                 830

Asn Glu Leu Leu Arg Ala Ala Gly Leu Glu Gly Trp Cys Asn Leu Ser
            835                 840                 845

Ala Ser Pro Thr Val Gln Thr Glu Ile Gly Lys Lys Met Glu Arg Phe
        850                 855                 860

Ala Ala Glu Lys Gln Glu Val Gln Asp Met Lys Leu Leu Ala Phe
865                 870                 875                 880

Thr Arg Glu Thr Asn Asn Pro Arg Ala Gln Ser Ala Ala Val Ala Ala
                    885                 890                 895

Leu Ala Met Leu Leu Ala Asn Glu Lys Val Ala Arg Cys Leu Pro Ala
                900                 905                 910

Tyr Ser Leu Phe Gly Asn Leu Ala Leu Ser Leu Glu Glu Ala Lys Ala
            915                 920                 925

Glu Gln Glu Ala Leu Ile Val Arg Cys Val Ser Ala Leu Tyr Asn Val
        930                 935                 940
```

```
Trp Ile Glu Leu Ser Ser Glu Ala Gly Ala Glu Thr Arg Met Gln
945                 950                 955                 960

Ile Val Lys Thr Leu Gln Arg Asn Gln Gln Lys Leu Thr Gly Asp Ala
            965                 970                 975

Gln His Leu Ala Lys Glu Val Leu Thr Ala Glu Leu Ser Gln Ala Asn
        980                 985                 990

Thr His Thr Lys Glu Ser Thr Pro Asp Ser Ser
        995                 1000

<210> SEQ ID NO 15
<211> LENGTH: 2496
<212> TYPE: DNA
<213> ORGANISM: Toxoplasm Gondii

<400> SEQUENCE: 15
atggcgagca agaccacgtc tgaggagctg aaaacggcca cggcgctgaa gaagaggtcg      60
tccgatgtcc acgcggtcga ccactccggc aatgtgtaca aaggatttca aatctggacg     120
gacttggcgc cgtcggtgaa ggaggagccg acctgatgt  ttgccaagtg catcgtgcag     180
gcggggacag acaaggggaa cttgacctgc gtccagatcg atccaccggg cttcgacgaa     240
ccgttcgaag tcccgcaggc gaatgcgtgg aacgtaaaca gcctgatcga ccccatgacg     300 tacgagaca  tcggcatgtt gcctcacacg aacattcctt gcgtcctcga cttcctcaag     360
gtgcgcttca tgaagaatca aatctacacg actgcggacc cgctcgtcgt cgccatcaat     420
cccttccgcg acctcgggaa caccacgctc gactggattg ttcgatacag agacactttc     480
gacctctcca aactcgcgcc ccatgttttc tacaccgccc gacgcgcgct cgacaacctc     540
cacgccgtca caagtcgca  aacgatcatc gtgtccggtg agtctggcgc gggcaagacg     600
gaggcgacga agcagattat gaggtatttt gcggcggcga gacggggtc  gatggatttg     660 cggattcaga acgcgatcat ggcggcgaat ccagtgcttg aggcatttgg aaatgcgaag     720
acgattcgca caacaactc  gtcgcgtttc ggacgcttca tgcagctgga tgtgggtcgc     780
gaaggaggca tcaagtttgg ctccgtcgtc gcctttctcc tggaaaagtc gcgtgttctc     840
acgcaggacg aacaggagcg gtcgtaccac atcttctacc aaatgtgcaa ggggggcggac    900 gcggcgatga aggagcgctt ccatatcctg ccgctctcgg agtacaagta catcaatccg     960
ttgtgcctgg acgcgccagg gatcgacgac gtcgcggagt ccacgaagt  ctgcgagtcg    1020 ttccggtcga tgaatctgac ggaggacgaa gtcgcgagcg tgtggagcat cgtgagtgga    1080
gtgctgctgc ttggcaacgt cgaggtgaca gcgacgaagg atgggggat  cgacgacgcc    1140 gcggcgatcg aggggaagaa cttggaggtt ttcaaaaagg cctgcgggct gctcttcctc    1200
gacgcggagc gcattcgcga agagctgacg gtgaaggttt cgtatgcggg gaatcaggag    1260
atccgcggcc ggtggaagca ggaagacgga gacatgctca gtcgtcgct  cgcgaaggcg    1320 atgtacgaca agttgttcat gtggatcatt gccgtgttga accgcagcat caagcctccg    1380
ggcggcttca agatcttcat gggcatgctc gacatcttcg gcttcgaagt cttcaagaac    1440
aactcgctgg agcagttctt catcaacatc acgaacgaaa tgctgcagaa gaacttcgtc    1500
gacatcgtct tcgaccgcga gagcaagctg tatcgtgacg agggtgtctc ctccaaggag    1560
ttgattttca cctcgaacgc agaagtgatc aagatcttga cggcgaagaa caactcggtg    1620
ctcgctgcgc tcgaggacca gtgcctcgcc cctggaggca gcgacgaaaa gttcctctcg    1680
acctgcaaga acgcgctgaa aggaaccacc aagttcaagc ctgcgaaggt ctctccgaac    1740
```

```
atcaatttcc tcatctcgca cactgtcggc gacatccagt acaacgccga aggcttcctc      1800
ttcaaaaaca aagatgtcct gcgagcagaa atcatggaaa tcgtgcagca aagcaagaac      1860
cccgtcgtcg cgcaactctt cgctggcatc gtcatggaga aggggaagat ggccaaggga      1920
caactgattg gtcgcagtt cctctcgcag ctgcagagcc tcatggaact tatcaacagc       1980
accgagcctc acttcattcg ctgcatcaag ccgaacgaca cgaagaagcc cctcgactgg      2040
gtgccgtcga aatgctcat tcagctgcac gcgctctccg tcctcgaggc tcttcagctc       2100
cgtcaactcg gctactctta cagacgtccg ttcaaggagt tcctcttcca gttcaagttt      2160
atcgacctct cggcttctga aaatccaaat ctggacccca agaagctgc gctgagactc       2220 ctcaaaagca gcaaactgcc cagcgaagaa taccagctcg gaagacaat ggttttcctc       2280 aagcagacgg gcgcgaaaga actgacgcag attcagagag aatgcctttc ttcttgggag      2340
cctctcgtct cagtgctcga ggcgtactac gctggcagac gccacaagaa gcagctgctg      2400
aaaaagaccc ccttcatcat tcgcgcccag gctcacatcc gcagacacct ggtggacaac      2460
aacgtcagcc ccgcgactgt tcagccggcg ttctag                                2496
```

<210> SEQ ID NO 16
<211> LENGTH: 831
<212> TYPE: PRT
<213> ORGANISM: Toxoplasma gondii

<400> SEQUENCE: 16

```
Met Ala Ser Lys Thr Thr Ser Glu Glu Leu Lys Thr Ala Thr Ala Leu
1               5                   10                  15

Lys Lys Arg Ser Ser Asp Val His Ala Val Asp His Ser Gly Asn Val
            20                  25                  30

Tyr Lys Gly Phe Gln Ile Trp Thr Asp Leu Ala Pro Ser Val Lys Glu
        35                  40                  45

Glu Pro Asp Leu Met Phe Ala Lys Cys Ile Val Gln Ala Gly Thr Asp
    50                  55                  60

Lys Gly Asn Leu Thr Cys Val Gln Ile Asp Pro Pro Gly Phe Asp Glu
65                  70                  75                  80

Pro Phe Glu Val Pro Gln Ala Asn Ala Trp Asn Val Asn Ser Leu Ile
                85                  90                  95

Asp Pro Met Thr Tyr Gly Asp Ile Gly Met Leu Pro His Thr Asn Ile
            100                 105                 110

Pro Cys Val Leu Asp Phe Leu Lys Val Arg Phe Met Lys Asn Gln Ile
        115                 120                 125

Tyr Thr Thr Ala Asp Pro Leu Val Ala Ile Asn Pro Phe Arg Asp
    130                 135                 140

Leu Gly Asn Thr Thr Leu Asp Trp Ile Val Arg Tyr Arg Asp Thr Phe
145                 150                 155                 160

Asp Leu Ser Lys Leu Ala Pro His Val Phe Tyr Thr Ala Arg Arg Ala
                165                 170                 175

Leu Asp Asn Leu His Ala Val Asn Lys Ser Gln Thr Ile Ile Val Ser
            180                 185                 190

Gly Glu Ser Gly Ala Gly Lys Thr Glu Ala Thr Lys Gln Ile Met Arg
        195                 200                 205

Tyr Phe Ala Ala Ala Lys Thr Gly Ser Met Asp Leu Arg Ile Gln Asn
    210                 215                 220

Ala Ile Met Ala Ala Asn Pro Val Leu Glu Ala Phe Gly Asn Ala Lys
225                 230                 235                 240
```

-continued

```
Thr Ile Arg Asn Asn Asn Ser Ser Arg Phe Gly Arg Phe Met Gln Leu
                245                 250                 255

Asp Val Gly Arg Glu Gly Gly Ile Lys Phe Gly Ser Val Val Ala Phe
            260                 265                 270

Leu Leu Glu Lys Ser Arg Val Leu Thr Gln Asp Glu Gln Glu Arg Ser
        275                 280                 285

Tyr His Ile Phe Tyr Gln Met Cys Lys Gly Ala Asp Ala Ala Met Lys
    290                 295                 300

Glu Arg Phe His Ile Leu Pro Leu Ser Glu Tyr Lys Tyr Ile Asn Pro
305                 310                 315                 320

Leu Cys Leu Asp Ala Pro Gly Ile Asp Val Ala Glu Phe His Glu
                325                 330                 335

Val Cys Glu Ser Phe Arg Ser Met Asn Leu Thr Glu Asp Glu Val Ala
            340                 345                 350

Ser Val Trp Ser Ile Val Ser Gly Val Leu Leu Gly Asn Val Glu
        355                 360                 365

Val Thr Ala Thr Lys Asp Gly Ile Asp Ala Ala Ala Ile Glu
    370                 375                 380

Gly Lys Asn Leu Glu Val Phe Lys Lys Ala Cys Gly Leu Leu Phe Leu
385                 390                 395                 400

Asp Ala Glu Arg Ile Arg Glu Glu Leu Thr Val Lys Val Ser Tyr Ala
                405                 410                 415

Gly Asn Gln Glu Ile Arg Gly Arg Trp Lys Gln Glu Asp Gly Asp Met
            420                 425                 430

Leu Lys Ser Ser Leu Ala Lys Ala Met Tyr Asp Lys Leu Phe Met Trp
        435                 440                 445

Ile Ile Ala Val Leu Asn Arg Ser Ile Lys Pro Pro Gly Gly Phe Lys
    450                 455                 460

Ile Phe Met Gly Met Leu Asp Ile Phe Gly Phe Glu Val Phe Lys Asn
465                 470                 475                 480

Asn Ser Leu Glu Gln Phe Phe Ile Asn Ile Thr Asn Glu Met Leu Gln
                485                 490                 495

Lys Asn Phe Val Asp Ile Val Phe Asp Arg Glu Ser Lys Leu Tyr Arg
            500                 505                 510

Asp Glu Gly Val Ser Ser Lys Glu Leu Ile Phe Thr Ser Asn Ala Glu
        515                 520                 525

Val Ile Lys Ile Leu Thr Ala Lys Asn Asn Ser Val Leu Ala Ala Leu
    530                 535                 540

Glu Asp Gln Cys Leu Ala Pro Gly Gly Ser Asp Glu Lys Phe Leu Ser
545                 550                 555                 560

Thr Cys Lys Asn Ala Leu Lys Gly Thr Thr Lys Phe Lys Pro Ala Lys
                565                 570                 575

Val Ser Pro Asn Ile Asn Phe Leu Ile Ser His Thr Val Gly Asp Ile
            580                 585                 590

Gln Tyr Asn Ala Glu Gly Phe Leu Phe Lys Asn Asp Val Leu Arg
        595                 600                 605

Ala Glu Ile Met Glu Ile Val Gln Gln Ser Lys Asn Pro Val Val Ala
    610                 615                 620

Gln Leu Phe Ala Gly Ile Val Met Glu Lys Gly Lys Met Ala Lys Gly
625                 630                 635                 640

Gln Leu Ile Gly Ser Gln Phe Leu Ser Gln Leu Gln Ser Leu Met Glu
                645                 650                 655

Leu Ile Asn Ser Thr Glu Pro His Phe Ile Arg Cys Ile Lys Pro Asn
```

```
                660                 665                 670
Asp Thr Lys Lys Pro Leu Asp Trp Val Pro Ser Lys Met Leu Ile Gln
            675                 680                 685

Leu His Ala Leu Ser Val Leu Glu Ala Leu Gln Leu Arg Gln Leu Gly
        690                 695                 700

Tyr Ser Tyr Arg Arg Pro Phe Lys Glu Phe Leu Phe Gln Phe Lys Phe
705                 710                 715                 720

Ile Asp Leu Ser Ala Ser Glu Asn Pro Asn Leu Asp Pro Lys Glu Ala
                725                 730                 735

Ala Leu Arg Leu Leu Lys Ser Ser Lys Leu Pro Ser Glu Glu Tyr Gln
            740                 745                 750

Leu Gly Lys Thr Met Val Phe Leu Lys Gln Thr Gly Ala Lys Glu Leu
        755                 760                 765

Thr Gln Ile Gln Arg Glu Cys Leu Ser Ser Trp Glu Pro Leu Val Ser
    770                 775                 780

Val Leu Glu Ala Tyr Tyr Ala Gly Arg Arg His Lys Lys Gln Leu Leu
785                 790                 795                 800

Lys Lys Thr Pro Phe Ile Ile Arg Ala Gln Ala His Ile Arg Arg His
                805                 810                 815

Leu Val Asp Asn Asn Val Ser Pro Ala Thr Val Gln Pro Ala Phe
            820                 825                 830

<210> SEQ ID NO 17
<211> LENGTH: 642
<212> TYPE: DNA
<213> ORGANISM: Toxoplasma gondii

<400> SEQUENCE: 17
atgagcaagg tcgagaagaa atgcccggtg tgctaccaga agctgccgaa cccggcagat      60
gttctgggtc cgatggacaa ggagttgaac tatttcatgt ggatgccagg cttcgagtgg     120
cgcccggaac cgaaggtggg ggagtacgat ggtgcctgtg agtcgccctc ttgccgcgag     180
ggggggcgcc ctgcggcaga cgaagacatg caggaggctc tcgaggagat ggtggaggcc     240
gacgaaatgt atgcgcgctt caacgcgaga gcttccggag gaaaggtatc cacgggagac     300
gccatgattc tcgcgcgcca gctcggactt gccccgtcct acgcagacaa acaggccttt     360
gaggaaaaga gcggcgacaa ccttgactac gccagcttcc agaaattcgt tggcaccagc     420 acccacccg  aagacaacat cgaggacctc gtcgaagcct cgcatactt  tgacgtctct     480 aagcacggtt acctgacgcg caagcagatg gggaacatcc tcatgaccta cggagagcct     540
ctcaccacag aagagtttaa tgccttggct gcggagtact tcacaagtga ccagatcgac     600
tacaggcaat tctgcaaggc aatgctcgag cgaagggagt aa                        642

<210> SEQ ID NO 18
<211> LENGTH: 213
<212> TYPE: PRT
<213> ORGANISM: Toxoplasma gondii

<400> SEQUENCE: 18

Met Ser Lys Val Glu Lys Lys Cys Pro Val Cys Tyr Gln Lys Leu Pro
1               5                   10                  15

Asn Pro Ala Asp Val Leu Gly Pro Met Asp Lys Glu Leu Asn Tyr Phe
            20                  25                  30

Met Trp Met Pro Gly Phe Glu Trp Arg Pro Glu Pro Lys Val Gly Glu
        35                  40                  45
```

Tyr Asp Gly Ala Cys Glu Ser Pro Ser Cys Arg Glu Gly Gly Arg Pro
             50                  55                  60

Ala Ala Asp Glu Asp Met Gln Glu Ala Leu Glu Glu Met Val Glu Ala
 65                  70                  75                  80

Asp Glu Met Tyr Ala Arg Phe Asn Ala Arg Ala Ser Gly Gly Lys Val
                 85                  90                  95

Ser Thr Gly Asp Ala Met Ile Leu Ala Arg Gln Leu Gly Leu Ala Pro
            100                 105                 110

Ser Tyr Ala Asp Lys Gln Ala Phe Glu Glu Lys Ser Gly Asp Asn Leu
            115                 120                 125

Asp Tyr Ala Ser Phe Gln Lys Phe Val Gly Thr Ser Thr His Pro Glu
130                 135                 140

Asp Asn Ile Glu Asp Leu Val Glu Ala Phe Ala Tyr Phe Asp Val Ser
145                 150                 155                 160

Lys His Gly Tyr Leu Thr Arg Lys Gln Met Gly Asn Ile Leu Met Thr
                165                 170                 175

Tyr Gly Glu Pro Leu Thr Thr Glu Phe Asn Ala Leu Ala Ala Glu
            180                 185                 190

Tyr Phe Thr Ser Asp Gln Ile Asp Tyr Arg Gln Phe Cys Lys Ala Met
            195                 200                 205

Leu Glu Arg Arg Glu
    210

<210> SEQ ID NO 19
<211> LENGTH: 264
<212> TYPE: DNA
<213> ORGANISM: Toxoplasma gondii

<400> SEQUENCE: 19
atgtcaatgg cgtggcctga ttttgaggcg tggatgtcga agaaactggc gtcctacaac      60
cctgaggagg agttgatcaa atctttcaag gcttttgacc ggtcgaacga cggcaccgtg     120
tctgcggacg agctttctca agttatgctc gctctcggcg agttgctttc cgacgaagaa     180
gtcaaggcca tgatcaagga agccgacccg aacggcactg gcaagatcca gtacgccaac     240
tttgtcaaga tgctgctgaa ataa                                           264

<210> SEQ ID NO 20
<211> LENGTH: 87
<212> TYPE: PRT
<213> ORGANISM: Toxoplasma gondii

<400> SEQUENCE: 20

Met Ser Met Ala Trp Pro Asp Phe Glu Ala Trp Met Ser Lys Lys Leu
 1               5                  10                  15

Ala Ser Tyr Asn Pro Glu Glu Glu Leu Ile Lys Ser Phe Lys Ala Phe
             20                  25                  30

Asp Arg Ser Asn Asp Gly Thr Val Ser Ala Asp Glu Leu Ser Gln Val
         35                  40                  45

Met Leu Ala Leu Gly Glu Leu Leu Ser Asp Glu Glu Val Lys Ala Met
 50                  55                  60

Ile Lys Glu Ala Asp Pro Asn Gly Thr Gly Lys Ile Gln Tyr Ala Asn
 65                  70                  75                  80

Phe Val Lys Met Leu Leu Lys
                 85

<210> SEQ ID NO 21

<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 21

```
Ser Met Glu Ala Pro Ala Ala Glu Ile Ser Gly His Ile Val Arg
1               5                   10                  15

Ser Pro Met Val Gly Thr Phe Tyr Arg Thr Pro Ser Pro Asp Ala Lys
            20                  25                  30

Ala Phe Ile Glu Val Gly Gln Lys Val Asn Val Gly Asp Thr Leu Cys
        35                  40                  45

Ile Val Glu Ala Met Lys Met Met Asn Gln Ile Glu Ala Asp Lys Ser
    50                  55                  60

Gly Thr Val Lys Ala Ile Leu Val Glu Ser Gly Gln Pro Val Glu Phe
65                  70                  75                  80

Asp Glu Pro Leu Val Val Ile Glu Arg Ser
                85                  90
```

<210> SEQ ID NO 22
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 22

```
Glu Gln Lys Leu Ile Ser Glu Glu Asp Leu
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 23

```
Glu Val His Thr Asn Gln Asp Pro Leu Asp
1               5                   10
```

<210> SEQ ID NO 24
<211> LENGTH: 773
<212> TYPE: PRT
<213> ORGANISM: Plasmodium falciparum

<400> SEQUENCE: 24

```
Met Ala Val Thr Asn Glu Glu Ile Lys Thr Ala Ser Lys Ile Val Arg
1               5                   10                  15

Arg Val Ser Asn Val Glu Ala Phe Asp Lys Ser Gly Ser Val Phe Lys
            20                  25                  30

Gly Tyr Gln Ile Trp Thr Asp Ile Ser Pro Thr Ile Glu Asn Asp Pro
        35                  40                  45

Asn Ile Met Phe Val Lys Cys Val Val Gln Gln Gly Ser Lys Lys Glu
    50                  55                  60

Lys Leu Thr Val Val Gln Ile Asp Pro Pro Gly Thr Gly Thr Pro Tyr
65                  70                  75                  80

Asp Ile Asp Pro Thr His Ala Trp Asn Cys Asn Ser Gln Val Asp Pro
                85                  90                  95

Met Ser Phe Gly Asp Ile Gly Leu Leu Asn His Thr Asn Ile Pro Cys
```

```
            100                 105                 110
Val Leu Asp Phe Leu Lys His Arg Tyr Leu Lys Asn Gln Ile Tyr Thr
            115                 120                 125

Thr Ala Val Pro Leu Ile Val Ala Ile Asn Pro Tyr Lys Asp Leu Gly
130                 135                 140

Asn Thr Thr Asn Glu Trp Ile Arg Arg Tyr Arg Asp Thr Ala Asp His
145                 150                 155                 160

Thr Lys Leu Pro Pro His Val Phe Thr Cys Ala Arg Glu Ala Leu Ser
                165                 170                 175

Asn Leu His Gly Val Asn Lys Ser Gln Thr Ile Ile Val Ser Gly Glu
                180                 185                 190

Ser Gly Ala Gly Lys Thr Glu Ala Thr Lys Gln Ile Met Arg Tyr Phe
                195                 200                 205

Ala Ser Ser Lys Ser Gly Asn Met Asp Leu Arg Ile Gln Thr Ala Ile
                210                 215                 220

Met Ala Ala Asn Pro Val Leu Glu Ala Phe Gly Asn Ala Lys Thr Ile
225                 230                 235                 240

Arg Asn Asn Asn Ser Ser Arg Phe Gly Arg Phe Met Gln Leu Val Ile
                245                 250                 255

Ser His Glu Gly Gly Ile Arg Tyr Gly Ser Val Val Ala Phe Leu Leu
                260                 265                 270

Glu Lys Ser Arg Ile Ile Thr Gln Asp Asp Asn Glu Arg Ser Tyr His
                275                 280                 285

Ile Phe Tyr Gln Phe Leu Lys Gly Ala Asn Ser Thr Met Lys Ser Lys
                290                 295                 300

Phe Gly Leu Lys Gly Val Thr Glu Tyr Lys Leu Leu Asn Pro Asn Ser
305                 310                 315                 320

Thr Glu Val Ser Gly Val Asp Asp Val Lys Asp Phe Glu Glu Val Ile
                325                 330                 335

Glu Ser Leu Lys Asn Met Glu Leu Ser Glu Ser Asp Ile Glu Val Ile
                340                 345                 350

Phe Ser Ile Val Ala Gly Ile Leu Thr Leu Gly Asn Val Arg Leu Ile
                355                 360                 365

Glu Lys Gln Glu Ala Gly Leu Ser Asp Ala Ala Ala Ile Met Asp Glu
                370                 375                 380

Asp Met Gly Val Phe Asn Lys Ala Cys Glu Leu Met Tyr Leu Asp Pro
385                 390                 395                 400

Glu Leu Ile Lys Arg Glu Ile Leu Ile Lys Val Thr Val Ala Gly Gly
                405                 410                 415

Thr Lys Ile Glu Gly Arg Trp Asn Lys Asn Asp Ala Glu Val Leu Lys
                420                 425                 430

Ser Ser Leu Cys Lys Ala Met Tyr Glu Lys Leu Phe Leu Trp Ile Ile
                435                 440                 445

Arg His Leu Asn Ser Arg Ile Glu Pro Glu Gly Gly Phe Lys Thr Phe
                450                 455                 460

Met Gly Met Leu Asp Ile Phe Gly Phe Glu Val Phe Lys Asn Asn Ser
465                 470                 475                 480

Leu Glu Gln Leu Phe Ile Asn Ile Thr Asn Glu Met Leu Gln Lys Asn
                485                 490                 495

Phe Val Asp Ile Val Phe Glu Arg Glu Ser Lys Leu Tyr Lys Asp Glu
                500                 505                 510

Gly Ile Ser Thr Ala Glu Leu Lys Tyr Thr Ser Asn Lys Glu Val Ile
                515                 520                 525
```

Asn Val Leu Cys Glu Lys Gly Lys Ser Val Leu Ser Tyr Leu Glu Asp
              530                 535                 540

Gln Cys Leu Ala Pro Gly Gly Thr Asp Glu Lys Phe Val Ser Ser Cys
545                 550                 555                 560

Ala Thr Asn Leu Lys Glu Asn Asn Lys Phe Thr Pro Ala Lys Val Ala
                565                 570                 575

Ser Asn Lys Asn Phe Ile Ile Gln His Thr Ile Gly Pro Ile Gln Tyr
                580                 585                 590

Cys Ala Glu Ser Phe Leu Leu Lys Asn Lys Asp Val Leu Arg Gly Asp
                595                 600                 605

Leu Val Glu Val Ile Lys Asp Ser Pro Asn Pro Ile Val Gln Gln Leu
                610                 615                 620

Phe Glu Gly Gln Val Ile Glu Lys Gly Lys Ile Ala Lys Gly Ser Leu
625                 630                 635                 640

Ile Gly Ser Gln Phe Leu Asn Gln Leu Thr Ser Leu Met Asn Leu Ile
                645                 650                 655

Asn Ser Thr Glu Pro His Phe Ile Arg Cys Ile Lys Pro Asn Glu Asn
                660                 665                 670

Lys Lys Pro Leu Glu Trp Cys Glu Pro Lys Ile Leu Ile Gln Leu His
                675                 680                 685

Ala Leu Ser Ile Leu Glu Ala Leu Val Leu Arg Gln Leu Gly Tyr Ser
                690                 695                 700

Tyr Arg Arg Thr Phe Glu Glu Phe Leu Tyr Gln Tyr Lys Phe Val Asp
705                 710                 715                 720

Ile Ala Ala Ala Glu Asp Ser Ser Val Glu Asn Gln Asn Lys Cys Val
                725                 730                 735

Asn Ile Leu Lys Leu Ser Gly Leu Ser Glu Ser Met Tyr Lys Ile Gly
                740                 745                 750

Lys Ser Met Val Phe Leu Lys Gln Glu Gly Ala Lys Ile Leu Thr Lys
                755                 760                 765

Ile Gln Arg Glu Lys
            770

<210> SEQ ID NO 25
<211> LENGTH: 775
<212> TYPE: PRT
<213> ORGANISM: Toxoplasma gondii

<400> SEQUENCE: 25

Met Ala Ser Lys Thr Thr Ser Glu Glu Leu Lys Thr Ala Thr Ala Leu
1               5                   10                  15

Lys Lys Arg Ser Ser Asp Val His Ala Val Asp His Ser Gly Asn Val
                20                  25                  30

Tyr Lys Gly Phe Gln Ile Trp Thr Asp Leu Ala Pro Ser Val Lys Glu
            35                  40                  45

Glu Pro Asp Leu Met Phe Ala Lys Cys Ile Val Gln Ala Gly Thr Asp
        50                  55                  60

Lys Gly Asn Leu Thr Cys Val Gln Ile Asp Pro Pro Gly Phe Asp Glu
65                  70                  75                  80

Pro Phe Glu Val Pro Gln Ala Asn Ala Trp Asn Val Asn Ser Leu Ile
                85                  90                  95

Asp Pro Met Thr Tyr Gly Asp Ile Gly Met Leu Pro His Thr Asn Ile
                100                 105                 110

Pro Cys Val Leu Asp Phe Leu Lys Val Arg Phe Met Lys Asn Gln Ile

```
            115                 120                 125
Tyr Thr Thr Ala Asp Pro Leu Val Val Ala Ile Asn Pro Phe Arg Asp
    130                 135                 140

Leu Gly Asn Thr Thr Leu Asp Trp Ile Val Arg Tyr Arg Asp Thr Phe
145                 150                 155                 160

Asp Leu Ser Lys Leu Ala Pro His Val Phe Tyr Thr Ala Arg Arg Ala
                165                 170                 175

Leu Asp Asn Leu His Ala Val Asn Lys Ser Gln Thr Ile Ile Val Ser
            180                 185                 190

Gly Glu Ser Gly Ala Gly Lys Thr Glu Ala Thr Lys Gln Ile Met Arg
        195                 200                 205

Tyr Phe Ala Ala Lys Thr Gly Ser Met Asp Leu Arg Ile Gln Asn
    210                 215                 220

Ala Ile Met Ala Ala Asn Pro Val Leu Glu Ala Phe Gly Asn Ala Lys
225                 230                 235                 240

Thr Ile Arg Asn Asn Ser Ser Arg Phe Gly Arg Phe Met Gln Leu
                245                 250                 255

Asp Val Gly Arg Glu Gly Gly Ile Lys Phe Gly Ser Val Val Ala Phe
            260                 265                 270

Leu Leu Glu Lys Ser Arg Val Leu Thr Gln Asp Gln Glu Arg Ser
        275                 280                 285

Tyr His Ile Phe Tyr Gln Met Cys Lys Gly Ala Asp Ala Ala Met Lys
    290                 295                 300

Glu Arg Phe His Ile Leu Pro Leu Ser Glu Tyr Lys Tyr Ile Asn Pro
305                 310                 315                 320

Leu Cys Leu Asp Ala Pro Gly Ile Asp Asp Val Ala Glu Phe His Glu
                325                 330                 335

Val Cys Glu Ser Phe Arg Ser Met Asn Leu Thr Glu Asp Glu Val Ala
            340                 345                 350

Ser Val Trp Ser Ile Val Ser Gly Val Leu Leu Gly Asn Val Glu
        355                 360                 365

Val Thr Ala Thr Lys Asp Gly Gly Ile Asp Asp Ala Ala Ile Glu
    370                 375                 380

Gly Lys Asn Leu Glu Val Phe Lys Lys Ala Cys Gly Leu Leu Phe Leu
385                 390                 395                 400

Asp Ala Glu Arg Ile Arg Glu Glu Leu Thr Val Lys Val Ser Tyr Ala
                405                 410                 415

Gly Asn Gln Glu Ile Arg Gly Arg Trp Lys Gln Glu Asp Gly Asp Met
            420                 425                 430

Leu Lys Ser Ser Leu Ala Lys Ala Met Tyr Asp Lys Leu Phe Met Trp
        435                 440                 445

Ile Ile Ala Val Leu Asn Arg Ser Ile Lys Pro Pro Gly Gly Phe Lys
    450                 455                 460

Ile Phe Met Gly Met Leu Asp Ile Phe Gly Phe Glu Val Phe Lys Asn
465                 470                 475                 480

Asn Ser Leu Glu Gln Phe Phe Ile Asn Ile Thr Asn Glu Met Leu Gln
                485                 490                 495

Lys Asn Phe Val Asp Ile Val Phe Asp Arg Glu Ser Lys Leu Tyr Arg
            500                 505                 510

Asp Glu Gly Val Ser Ser Lys Glu Leu Ile Phe Thr Ser Asn Ala Glu
        515                 520                 525

Val Ile Lys Ile Leu Thr Ala Lys Asn Asn Ser Val Leu Ala Ala Leu
    530                 535                 540
```

```
Glu Asp Gln Cys Leu Ala Pro Gly Gly Ser Asp Glu Lys Phe Leu Ser
545                 550                 555                 560

Thr Cys Lys Asn Ala Leu Lys Gly Thr Thr Lys Phe Lys Pro Ala Lys
                565                 570                 575

Val Ser Pro Asn Ile Asn Phe Leu Ile Ser His Thr Val Gly Asp Ile
            580                 585                 590

Gln Tyr Asn Ala Glu Gly Phe Leu Phe Lys Asn Lys Asp Val Leu Arg
        595                 600                 605

Ala Glu Ile Met Glu Ile Val Gln Gln Ser Lys Asn Pro Val Val Ala
610                 615                 620

Gln Leu Phe Ala Gly Ile Val Met Glu Lys Gly Lys Met Ala Lys Gly
625                 630                 635                 640

Gln Leu Ile Gly Ser Gln Phe Leu Ser Gln Leu Gln Ser Leu Met Glu
                645                 650                 655

Leu Ile Asn Ser Thr Glu Pro His Phe Ile Arg Cys Ile Lys Pro Asn
            660                 665                 670

Asp Thr Lys Lys Pro Leu Asp Trp Val Pro Ser Lys Met Leu Ile Gln
        675                 680                 685

Leu His Ala Leu Ser Val Leu Glu Ala Leu Gln Leu Arg Gln Leu Gly
690                 695                 700

Tyr Ser Tyr Arg Arg Pro Phe Lys Glu Phe Leu Phe Gln Phe Lys Phe
705                 710                 715                 720

Ile Asp Leu Ser Ala Ser Glu Asn Pro Asn Leu Asp Pro Lys Glu Ala
                725                 730                 735

Ala Leu Arg Leu Leu Lys Ser Ser Lys Leu Pro Ser Glu Glu Tyr Gln
            740                 745                 750

Leu Gly Lys Thr Met Val Phe Leu Lys Gln Thr Gly Ala Lys Glu Leu
        755                 760                 765

Thr Gln Ile Gln Arg Glu Cys
770                 775

<210> SEQ ID NO 26
<211> LENGTH: 798
<212> TYPE: PRT
<213> ORGANISM: Plasmodium falciparum

<400> SEQUENCE: 26

Met Ala Val Thr Asn Glu Glu Ile Lys Thr Ala Ser Lys Ile Val Arg
1               5                   10                  15

Arg Val Ser Asn Val Glu Ala Phe Asp Lys Ser Gly Ser Val Phe Lys
            20                  25                  30

Gly Tyr Gln Ile Trp Thr Asp Ile Ser Pro Thr Ile Glu Asn Asp Pro
        35                  40                  45

Asn Ile Met Phe Val Lys Cys Val Val Gln Gln Gly Ser Lys Lys Glu
50                  55                  60

Lys Leu Thr Val Val Gln Ile Asp Pro Pro Gly Thr Gly Thr Pro Tyr
65                  70                  75                  80

Asp Ile Asp Pro Thr His Ala Trp Asn Cys Asn Ser Gln Val Asp Pro
                85                  90                  95

Met Ser Phe Gly Asp Ile Gly Leu Leu Asn His Thr Asn Ile Pro Cys
            100                 105                 110

Val Leu Asp Phe Leu Lys His Arg Tyr Leu Lys Asn Gln Ile Tyr Thr
        115                 120                 125

Thr Ala Val Pro Leu Ile Val Ala Ile Asn Pro Tyr Lys Asp Leu Gly
```

```
            130                 135                 140
Asn Thr Thr Asn Glu Trp Ile Arg Arg Tyr Arg Asp Thr Ala Asp His
145                 150                 155                 160

Thr Lys Leu Pro Pro His Val Phe Thr Cys Ala Arg Glu Ala Leu Ser
                165                 170                 175

Asn Leu His Gly Val Asn Lys Ser Gln Thr Ile Ile Val Ser Gly Glu
            180                 185                 190

Ser Gly Ala Gly Lys Thr Glu Ala Thr Lys Gln Ile Met Arg Tyr Phe
            195                 200                 205

Ala Ser Ser Lys Ser Gly Asn Met Asp Leu Arg Ile Gln Thr Ala Ile
            210                 215                 220

Met Ala Ala Asn Pro Val Leu Glu Ala Phe Gly Asn Ala Lys Thr Ile
225                 230                 235                 240

Arg Asn Asn Asn Ser Ser Arg Phe Gly Arg Phe Met Gln Leu Val Ile
                245                 250                 255

Ser His Glu Gly Gly Ile Arg Tyr Gly Ser Val Val Ala Phe Leu Leu
            260                 265                 270

Glu Lys Ser Arg Ile Ile Thr Gln Asp Asp Asn Glu Arg Ser Tyr His
            275                 280                 285

Ile Phe Tyr Gln Phe Leu Lys Gly Ala Asn Ser Thr Met Lys Ser Lys
            290                 295                 300

Phe Gly Leu Lys Gly Val Thr Glu Tyr Lys Leu Leu Asn Pro Asn Ser
305                 310                 315                 320

Thr Glu Val Ser Gly Val Asp Asp Val Lys Asp Phe Glu Glu Val Ile
                325                 330                 335

Glu Ser Leu Lys Asn Met Glu Leu Ser Glu Ser Asp Ile Glu Val Ile
            340                 345                 350

Phe Ser Ile Val Ala Gly Ile Leu Thr Leu Gly Asn Val Arg Leu Ile
            355                 360                 365

Glu Lys Gln Glu Ala Gly Leu Ser Asp Ala Ala Ala Ile Met Asp Glu
            370                 375                 380

Asp Met Gly Val Phe Asn Lys Ala Cys Glu Leu Met Tyr Leu Asp Pro
385                 390                 395                 400

Glu Leu Ile Lys Arg Glu Ile Leu Ile Lys Val Thr Val Ala Gly Gly
                405                 410                 415

Thr Lys Ile Glu Gly Arg Trp Asn Lys Asn Asp Ala Glu Val Leu Lys
            420                 425                 430

Ser Ser Leu Cys Lys Ala Met Tyr Glu Lys Leu Phe Leu Trp Ile Ile
            435                 440                 445

Arg His Leu Asn Ser Arg Ile Glu Pro Glu Gly Gly Phe Lys Thr Phe
            450                 455                 460

Met Gly Met Leu Asp Ile Phe Gly Phe Glu Val Phe Lys Asn Asn Ser
465                 470                 475                 480

Leu Glu Gln Leu Phe Ile Asn Ile Thr Asn Glu Met Leu Gln Lys Asn
                485                 490                 495

Phe Val Asp Ile Val Phe Glu Arg Glu Ser Lys Leu Tyr Lys Asp Glu
                500                 505                 510

Gly Ile Ser Thr Ala Glu Leu Lys Tyr Thr Ser Asn Lys Glu Val Ile
            515                 520                 525

Asn Val Leu Cys Glu Lys Gly Lys Ser Val Leu Ser Tyr Leu Glu Asp
            530                 535                 540

Gln Cys Leu Ala Pro Gly Gly Thr Asp Glu Lys Phe Val Ser Ser Cys
545                 550                 555                 560
```

Ala Thr Asn Leu Lys Glu Asn Lys Phe Thr Pro Ala Lys Val Ala
            565                 570                 575

Ser Asn Lys Asn Phe Ile Ile Gln His Thr Ile Gly Pro Ile Gln Tyr
            580                 585                 590

Cys Ala Glu Ser Phe Leu Leu Lys Asn Lys Asp Val Leu Arg Gly Asp
            595                 600                 605

Leu Val Glu Val Ile Lys Asp Ser Pro Asn Pro Ile Val Gln Gln Leu
    610                 615                 620

Phe Glu Gly Gln Val Ile Glu Lys Gly Lys Ile Ala Lys Gly Ser Leu
625                 630                 635                 640

Ile Gly Ser Gln Phe Leu Asn Gln Leu Thr Ser Leu Met Asn Leu Ile
            645                 650                 655

Asn Ser Thr Glu Pro His Phe Ile Arg Cys Ile Lys Pro Asn Glu Asn
            660                 665                 670

Lys Lys Pro Leu Glu Trp Cys Glu Pro Lys Ile Leu Ile Gln Leu His
            675                 680                 685

Ala Leu Ser Ile Leu Glu Ala Leu Val Leu Arg Gln Leu Gly Tyr Ser
            690                 695                 700

Tyr Arg Arg Thr Phe Glu Glu Phe Leu Tyr Gln Tyr Lys Phe Val Asp
705                 710                 715                 720

Ile Ala Ala Ala Glu Asp Ser Ser Val Glu Asn Gln Asn Lys Cys Val
            725                 730                 735

Asn Ile Leu Lys Leu Ser Gly Leu Ser Glu Ser Met Tyr Lys Ile Gly
            740                 745                 750

Lys Ser Met Val Phe Leu Lys Gln Glu Gly Ala Lys Ile Leu Thr Lys
            755                 760                 765

Ile Gln Arg Glu Lys Leu Val Glu Trp Glu Asn Cys Val Ser Val Ile
            770                 775                 780

Glu Ala Ala Ile Leu Lys His Lys Tyr Lys Gln Lys Val Asn
785                 790                 795

<210> SEQ ID NO 27
<211> LENGTH: 800
<212> TYPE: PRT
<213> ORGANISM: Toxoplasma gondii

<400> SEQUENCE: 27

Met Ala Ser Lys Thr Thr Ser Glu Glu Leu Lys Thr Ala Thr Ala Leu
1               5                   10                  15

Lys Lys Arg Ser Ser Asp Val His Ala Val Asp His Ser Gly Asn Val
            20                  25                  30

Tyr Lys Gly Phe Gln Ile Trp Thr Asp Leu Ala Pro Ser Val Lys Glu
        35                  40                  45

Glu Pro Asp Leu Met Phe Ala Lys Cys Ile Val Gln Ala Gly Thr Asp
    50                  55                  60

Lys Gly Asn Leu Thr Cys Val Gln Ile Asp Pro Gly Phe Asp Glu
65                  70                  75                  80

Pro Phe Glu Val Pro Gln Ala Asn Ala Trp Asn Val Asn Ser Leu Ile
            85                  90                  95

Asp Pro Met Thr Tyr Gly Asp Ile Gly Met Leu Pro His Thr Asn Ile
            100                 105                 110

Pro Cys Val Leu Asp Phe Leu Lys Val Arg Phe Met Lys Asn Gln Ile
            115                 120                 125

Tyr Thr Thr Ala Asp Pro Leu Val Val Ala Ile Asn Pro Phe Arg Asp

-continued

```
            130             135             140
Leu Gly Asn Thr Thr Leu Asp Trp Ile Val Arg Tyr Arg Asp Thr Phe
145                 150                 155                 160

Asp Leu Ser Lys Leu Ala Pro His Val Phe Tyr Thr Ala Arg Arg Ala
                165                 170                 175

Leu Asp Asn Leu His Ala Val Asn Lys Ser Gln Thr Ile Ile Val Ser
            180                 185                 190

Gly Glu Ser Gly Ala Gly Lys Thr Glu Ala Thr Lys Gln Ile Met Arg
        195                 200                 205

Tyr Phe Ala Ala Ala Lys Thr Gly Ser Met Asp Leu Arg Ile Gln Asn
    210                 215                 220

Ala Ile Met Ala Ala Asn Pro Val Leu Glu Ala Phe Gly Asn Ala Lys
225                 230                 235                 240

Thr Ile Arg Asn Asn Asn Ser Ser Arg Phe Gly Arg Phe Met Gln Leu
                245                 250                 255

Asp Val Gly Arg Glu Gly Gly Ile Lys Phe Gly Ser Val Val Ala Phe
            260                 265                 270

Leu Leu Glu Lys Ser Arg Val Leu Thr Gln Asp Glu Gln Glu Arg Ser
        275                 280                 285

Tyr His Ile Phe Tyr Gln Met Cys Lys Gly Ala Asp Ala Ala Met Lys
    290                 295                 300

Glu Arg Phe His Ile Leu Pro Leu Ser Glu Tyr Lys Tyr Ile Asn Pro
305                 310                 315                 320

Leu Cys Leu Asp Ala Pro Gly Ile Asp Asp Val Ala Glu Phe His Glu
                325                 330                 335

Val Cys Glu Ser Phe Arg Ser Met Asn Leu Thr Glu Asp Glu Val Ala
            340                 345                 350

Ser Val Trp Ser Ile Val Ser Gly Val Leu Leu Leu Gly Asn Val Glu
        355                 360                 365

Val Thr Ala Thr Lys Asp Gly Ile Asp Asp Ala Ala Ala Ile Glu
    370                 375                 380

Gly Lys Asn Leu Glu Val Phe Lys Lys Ala Cys Gly Leu Leu Phe Leu
385                 390                 395                 400

Asp Ala Glu Arg Ile Arg Glu Glu Leu Thr Val Lys Val Ser Tyr Ala
                405                 410                 415

Gly Asn Gln Glu Ile Arg Gly Arg Trp Lys Gln Glu Asp Gly Asp Met
            420                 425                 430

Leu Lys Ser Ser Leu Ala Lys Ala Met Tyr Asp Lys Leu Phe Met Trp
        435                 440                 445

Ile Ile Ala Val Leu Asn Arg Ser Ile Lys Pro Pro Gly Gly Phe Lys
    450                 455                 460

Ile Phe Met Gly Met Leu Asp Ile Phe Gly Phe Glu Val Phe Lys Asn
465                 470                 475                 480

Asn Ser Leu Glu Gln Phe Phe Ile Asn Ile Thr Asn Glu Met Leu Gln
                485                 490                 495

Lys Asn Phe Val Asp Ile Val Phe Asp Arg Glu Ser Lys Leu Tyr Arg
            500                 505                 510

Asp Glu Gly Val Ser Ser Lys Glu Leu Ile Phe Thr Ser Asn Ala Glu
        515                 520                 525

Val Ile Lys Ile Leu Thr Ala Lys Asn Asn Ser Val Leu Ala Ala Leu
    530                 535                 540

Glu Asp Gln Cys Leu Ala Pro Gly Gly Ser Asp Glu Lys Phe Leu Ser
545                 550                 555                 560
```

```
Thr Cys Lys Asn Ala Leu Lys Gly Thr Thr Lys Phe Lys Pro Ala Lys
                565                 570                 575

Val Ser Pro Asn Ile Asn Phe Leu Ile Ser His Thr Val Gly Asp Ile
            580                 585                 590

Gln Tyr Asn Ala Glu Gly Phe Leu Phe Lys Asn Lys Asp Val Leu Arg
        595                 600                 605

Ala Glu Ile Met Glu Ile Val Gln Gln Ser Lys Asn Pro Val Val Ala
    610                 615                 620

Gln Leu Phe Ala Gly Ile Val Met Glu Lys Gly Lys Met Ala Lys Gly
625                 630                 635                 640

Gln Leu Ile Gly Ser Gln Phe Leu Ser Gln Leu Gln Ser Leu Met Glu
                645                 650                 655

Leu Ile Asn Ser Thr Glu Pro His Phe Ile Arg Cys Ile Lys Pro Asn
            660                 665                 670

Asp Thr Lys Lys Pro Leu Asp Trp Val Pro Ser Lys Met Leu Ile Gln
        675                 680                 685

Leu His Ala Leu Ser Val Leu Glu Ala Leu Gln Leu Arg Gln Leu Gly
    690                 695                 700

Tyr Ser Tyr Arg Arg Pro Phe Lys Glu Phe Leu Phe Gln Phe Lys Phe
705                 710                 715                 720

Ile Asp Leu Ser Ala Ser Glu Asn Pro Asn Leu Asp Pro Lys Glu Ala
                725                 730                 735

Ala Leu Arg Leu Leu Lys Ser Ser Lys Leu Pro Ser Glu Glu Tyr Gln
            740                 745                 750

Leu Gly Lys Thr Met Val Phe Leu Lys Gln Thr Gly Ala Lys Glu Leu
        755                 760                 765

Thr Gln Ile Gln Arg Glu Cys Leu Ser Ser Trp Glu Pro Leu Val Ser
    770                 775                 780

Val Leu Glu Ala Tyr Tyr Ala Gly Arg Arg His Lys Lys Gln Leu Leu
785                 790                 795                 800

<210> SEQ ID NO 28
<211> LENGTH: 961
<212> TYPE: PRT
<213> ORGANISM: Caenorhabditis elegans

<400> SEQUENCE: 28

Met Val Ala Arg Val Gln Thr Ala Glu Glu Ile Arg Asp Glu Gly Asn
1               5                   10                  15

Ala Ala Val Lys Asp Gln Asp Tyr Ile Lys Ala Asp Glu Leu Tyr Thr
            20                  25                  30

Glu Ala Leu Gln Leu Thr Thr Asp Glu Asp Lys Ala Leu Arg Pro Val
        35                  40                  45

Leu Tyr Arg Asn Arg Ala Met Ala Arg Leu Lys Arg Asp Asp Phe Glu
    50                  55                  60

Gly Ala Gln Ser Asp Cys Thr Lys Ala Leu Glu Phe Asp Gly Ala Asp
65                  70                  75                  80

Val Lys Ala Leu Phe Arg Arg Ser Leu Ala Arg Glu Gln Leu Gly Asn
                85                  90                  95

Val Gly Pro Ala Phe Gln Asp Ala Lys Glu Ala Leu Arg Leu Ser Pro
            100                 105                 110

Asn Asp Lys Gly Ile Val Glu Val Leu Gln Arg Leu Val Lys Ala Asn
        115                 120                 125

Asn Asp Lys Ile Lys Gln Thr Thr Ser Leu Ala Asn Lys Val Thr Asp
```

```
                130                 135                 140
Met Glu Lys Leu Ala Phe Arg Gly Glu Ala Lys Asp Thr Glu Gln Lys
145                 150                 155                 160

Met Thr Ala Leu Asn Asn Leu Leu Val Leu Cys Arg Glu Ser Glu Ser
                165                 170                 175

Gly Ala Thr Gly Val Trp Asn Gln Gly Ala Leu Val Pro Phe Val Leu
                180                 185                 190

Asn Leu Ile Asn Asp Ala Ser Glu Asn Glu Glu Val Thr Val Thr Ala
                195                 200                 205

Ile Arg Ile Leu Asp Glu Thr Ile Lys Asn Ser Val Arg Cys Met Lys
                210                 215                 220

Phe Leu Ala Met His Asp Pro Asp Gly Pro Lys Ser Val Arg Phe Val
225                 230                 235                 240

Cys Arg Leu Met Cys Lys Lys Ser Thr Lys Asp Phe Val Asp Ala Thr
                245                 250                 255

Gly Ile Leu Val Gln Arg Val Phe Asn Ala Met Ala Lys Met Asp Arg
                260                 265                 270

Gln Lys Glu Met Lys Pro Asp Pro Glu Val Ala Glu Ala Asn Lys Ile
                275                 280                 285

Trp Ile Ile Arg Val Leu Leu Glu Leu Gln Glu Met Leu Gln Asp Pro
                290                 295                 300

Lys Val Gly Ala Val Gln Arg Glu Thr Cys Ile Asp Leu Phe Leu Lys
305                 310                 315                 320

Asn Leu Met His Met Asp Gly Gly Ile Pro Arg Gly Trp Ser Trp Lys
                325                 330                 335

Phe Val Glu Glu Arg Gly Leu Leu Ala Leu Leu Asp Val Ala Ser Gln
                340                 345                 350

Ile Pro Glu Leu Cys Glu Tyr Pro Val Ser Ala Glu Thr Arg Gln His
                355                 360                 365

Val Ala Ile Cys Leu Gln Arg Leu Glu Glu Asp Met Val Phe Asp Thr
                370                 375                 380

Lys Arg Thr Ile Phe Lys Glu Lys Val Asp Met Phe Phe Asn Ala Leu
385                 390                 395                 400

Ile Ser Arg Cys Thr Asn Asp Asp Glu Gly His Lys Tyr Arg Ile Lys
                405                 410                 415

Leu Ser Cys Phe Leu Ile Thr Met Leu Gln Gly Pro Val Asp Ile Gly
                420                 425                 430

Ile Asn Leu Ile Thr Asn Asp Gln Leu Thr Pro Ile Met Leu Glu Met
                435                 440                 445

Ala Ala Ser Gln Asp His Leu Met Gln Gly Ile Ala Ala Glu Leu Ile
                450                 455                 460

Val Ala Thr Val Ser Lys His Glu Arg Ala Ile Asn Met Leu Lys Val
465                 470                 475                 480

Gly Ile Pro Val Leu Arg Ala Leu Tyr Asp Ser Glu Asp Pro Thr Val
                485                 490                 495

Lys Val Arg Ala Leu Val Gly Leu Cys Lys Ile Gly Ala Ala Gly Gly
                500                 505                 510

Asp Asp Ile Ser Lys Ala Thr Met Lys Glu Glu Ala Val Ile Ser Leu
                515                 520                 525

Ala Lys Thr Cys Lys Lys Phe Leu Leu Glu Thr Glu Lys Tyr Ser Val
                530                 535                 540

Asp Ile Arg Arg Tyr Ala Cys Glu Gly Leu Ser Tyr Leu Ser Leu Asp
545                 550                 555                 560
```

-continued

```
Ala Asp Val Lys Glu Trp Ile Val Asp Asp Ser Leu Leu Lys Ala
            565                 570                 575
Leu Val Leu Leu Ala Lys Lys Ala Gly Ala Leu Cys Val Tyr Thr Leu
        580                 585                 590
Ala Thr Ile Tyr Ala Asn Leu Ser Asn Ala Phe Glu Lys Pro Lys Val
        595                 600                 605
Asp Glu Glu Met Val Lys Leu Ala Gln Phe Ala Lys His His Val Pro
        610                 615                 620
Glu Thr His Pro Lys Asp Thr Glu Glu Tyr Val Glu Lys Arg Val Arg
625                 630                 635                 640
Ala Leu Val Glu Glu Gly Ala Val Pro Ala Cys Val Ala Val Ser Lys
                645                 650                 655
Thr Glu Ser Lys Asn Ala Leu Glu Leu Ile Ala Arg Ser Leu Leu Ala
                660                 665                 670
Phe Ala Glu Tyr Glu Asp Leu Arg Gly Arg Ile Ile Ala Glu Gly Gly
            675                 680                 685
Thr Val Leu Cys Leu Arg Leu Thr Lys Glu Ala Ser Gly Glu Gly Lys
        690                 695                 700
Ile Lys Ala Gly His Ala Ile Ala Lys Leu Gly Ala Lys Ala Asp Pro
705                 710                 715                 720
Met Ile Ser Phe Pro Gly Gln Arg Ala Tyr Glu Val Val Lys Pro Leu
                725                 730                 735
Cys Asp Leu Leu His Pro Asp Val Glu Gly Lys Ala Asn Tyr Asp Ser
                740                 745                 750
Leu Leu Thr Leu Thr Asn Leu Ala Ser Val Ser Asp Ser Ile Arg Gly
            755                 760                 765
Arg Ile Leu Lys Glu Lys Ala Ile Pro Lys Ile Glu Glu Phe Trp Phe
        770                 775                 780
Met Thr Asp His Glu His Leu Arg Ala Ala Ala Glu Leu Leu Leu
785                 790                 795                 800
Asn Leu Leu Phe Phe Glu Lys Phe Tyr Glu Glu Thr Val Ala Pro Gly
                805                 810                 815
Thr Asp Arg Leu Lys Leu Trp Val Leu Tyr Ser Ala Glu Val Glu Glu
            820                 825                 830
Glu Arg Leu Ser Arg Ala Ser Ala Ala Gly Phe Ala Ile Leu Thr Glu
        835                 840                 845
Asp Glu Asn Ala Cys Ala Arg Ile Met Asp Glu Ile Lys Ser Trp Pro
850                 855                 860
Glu Val Phe Lys Asp Ile Ala Met His Glu Asp Ala Glu Thr Gln Arg
865                 870                 875                 880
Arg Gly Leu Met Gly Ile Ala Asn Ile Met His Ser Ser Asn Lys Leu
                885                 890                 895
Cys Ser Glu Ile Val Ser Ser Glu Val Phe Arg Val Leu Val Ala Val
                900                 905                 910
Thr Lys Leu Gly Thr Ile Asn Gln Glu Arg Ala Gly Ser Thr Glu Gln
            915                 920                 925
Ala Lys Arg Gly Leu Glu Ala Ala Glu Lys Phe Gly Leu Ile Lys Ala
        930                 935                 940
Thr Asp Arg Glu Ile Tyr Glu Arg Glu Asn Gln Met Ser Thr Ile Gln
945                 950                 955                 960
Glu
```

<210> SEQ ID NO 29
<211> LENGTH: 702
<212> TYPE: PRT
<213> ORGANISM: Podospora anserina

<400> SEQUENCE: 29

```
Met Ala Thr Val Ala Glu Ala Ala Ala Pro Glu Pro Leu Gly
 1               5                  10                  15

Arg Leu Asp Gln Thr Leu Leu Ile Phe Ala Gly Leu Met Glu Gly Gly
                20                  25                  30

Lys Glu Asp Glu Glu Thr Val Arg Glu Leu Gly Glu Leu Thr Arg Leu
            35                  40                  45

Leu Asn Asp Asp Val Glu Val Thr Lys Lys Gly Glu Thr Ser Val Thr
        50                  55                  60

Thr Val Ile Asp Ser Asp Cys Val Asp Thr Ile Leu Cys Tyr Leu Asp
    65                  70                  75                  80

Met Arg Gln Pro Asp Val Val Arg Ala His Ala Ala Leu Cys Thr Ser
                85                  90                  95

Ala Tyr Leu Lys Ala Ala Gly Glu Asp Gly Gly Lys Lys Leu Ala Glu
            100                 105                 110

Phe Phe His Asp Arg Val Arg Arg Gly Thr Tyr Asp Asp Tyr Ile Val
        115                 120                 125

Ala Phe Cys Val Ala Ala Thr Ile Phe Pro Ile Val Pro Asp Leu Thr
    130                 135                 140

Ser Glu Leu Phe Leu Ser Gly Phe Leu Ala Ser Leu Gly Pro Leu
145                 150                 155                 160

Met Arg Arg Lys Trp Lys Ser Arg Lys Val Thr Ala Cys Leu Glu
                165                 170                 175

Met Leu Asn Ala Ala Cys Met Asn Ser Ala Cys Arg Glu Ala Val Gln
            180                 185                 190

Lys Tyr Cys Thr Glu Trp Leu Glu Glu Ile Val Glu Gln Asp Pro Asp
        195                 200                 205

Asp Ala Val Lys Ser Met His Thr Val Asp Pro Asp Met His Leu Gln
    210                 215                 220

Glu Gly Ser Ile Ser Met Arg Arg His Ser Leu Gln Val Gln Asn Leu
225                 230                 235                 240

Ala Ala Val Val Leu Ala Lys Leu Arg Ala Val Pro Ser Thr Ala Ala
                245                 250                 255

Thr Ala Gly Pro Glu Ala Arg Ile Gln Pro Ala Thr Thr Ser Ile Glu
            260                 265                 270

Asp Leu Ser Lys Arg Phe Thr Arg Met Leu Leu Asp Glu Asp Glu Ile
        275                 280                 285

Glu His Val Gln Pro Ser Ile Glu Gly Leu Ala Tyr Ala Ser Leu Gln
    290                 295                 300

Pro Lys Val Lys Glu Ser Leu Ser Lys Asp Ser Lys Thr Leu Lys Arg
305                 310                 315                 320

Leu Val Lys Ala Leu Asp Glu Ala Pro Pro Arg Ser Pro Met Ile Tyr
                325                 330                 335

Gly Ala Leu Ser Ile Phe Thr Asn Leu Thr Arg Tyr Arg Pro Ile Glu
            340                 345                 350

Thr Asp Glu Glu Lys Arg Ile Arg Gln Leu Lys Ala Tyr Ala Asn Ala
        355                 360                 365

Ala Gly Lys Leu Gln Gln Val Asp Pro Leu Asn Glu Asp Glu His Val
    370                 375                 380
```

```
Thr Glu Arg Cys Lys Arg Val Phe Glu Ala Gly Leu Thr Pro Val Leu
385                 390                 395                 400

Ile Lys Gln Ser Lys Ser Gly Ser Ala Ala Ser Leu Ala Leu Ile Ile
            405                 410                 415

Ser Ile Ile His Ala Leu Ser Thr Pro Pro Leu Arg Gly Gln Leu
        420                 425                 430

Ala Gln Gln Gly Ala Val Arg Leu Leu Ile Ala Ala Trp Thr Ala Leu
            435                 440                 445

Pro Glu Thr Glu Asn Gly Pro Lys Arg Ala Ala Gln Ala Leu Ala
    450                 455                 460

Arg Ile Leu Ile Ser Thr Asn Pro Ala Leu Val Phe Gly Gly Thr Arg
465                 470                 475                 480

Pro Ile Pro Gln Ser Ala Ala Ile Arg Pro Leu Ala Ser Ile Leu Thr
            485                 490                 495

Pro Asp Pro Thr Ala Asp Arg Arg Asp Leu Leu Pro Thr Phe Glu Ser
            500                 505                 510

Leu Met Ala Leu Thr Asn Leu Ala Ser Thr Asp Asp Thr Arg Lys
    515                 520                 525

Ser Ile Ile Arg Thr Ala Trp Asp Asp Val Glu Glu Gln Leu Phe Asn
530                 535                 540

Pro Asn Ser Arg Val Cys Thr Ala Ala Val Glu Leu Val Cys Asn Leu
545                 550                 555                 560

Val Gln Asp Pro Glu Gln Thr Leu Ala Leu Phe Gly Asp Gly Ser Pro
            565                 570                 575

Lys Ala Lys Asn Arg Val Lys Val Ile Val Ala Leu Ala Asp Ala Glu
            580                 585                 590

Asp Pro Lys Thr Arg Ser Ala Ala Gly Gly Ala Leu Ala Ser Leu Thr
            595                 600                 605

Gly Phe Asp Glu Val Val Arg Ala Val Met Gly Leu Glu Arg Gly Val
    610                 615                 620

Glu Val Val Leu Gly Leu Cys Arg Asp Glu Arg Glu Asp Leu Arg His
625                 630                 635                 640

Arg Gly Ala Val Val Arg Asn Met Val Phe Ser Glu Gly Glu Val
            645                 650                 655

Gly Arg Leu Ala Arg Gly Lys Leu Val Glu Gly Ala Val Glu Ala
            660                 665                 670

Leu Met Glu Cys Ala Lys Gly Ser Lys Arg Arg Glu Val Val Glu Val
    675                 680                 685

Val Val Gln Ala Ala Glu Gly Leu Met Gly Glu Gly Gly Lys
690                 695                 700

<210> SEQ ID NO 30
<211> LENGTH: 789
<212> TYPE: PRT
<213> ORGANISM: Saccharomyces cerevisiae

<400> SEQUENCE: 30

Met Pro Leu Cys Glu Lys Gly Asn Asp Pro Ile Asp Ser Ser Thr Ile
1               5                   10                  15

Asp Ser Leu Cys Ala Ala Phe Asp Lys Thr Leu Lys Ser Thr Pro Asp
            20                  25                  30

Val Gln Lys Tyr Asn Asp Ala Ile Asn Thr Ile Phe Gln Leu Arg Gln
        35                  40                  45

Lys Ser Glu Ser Gly Lys Met Pro Ala Asp Leu Thr Asn Ser Glu Ala
    50                  55                  60
```

```
Leu Lys Asp Arg Gln Lys Ile Glu Glu Ile Leu Thr Arg Ser Tyr Gln
 65                  70                  75                  80

Asp His Ser Glu Ser Arg Val His Leu Ser Lys Leu Ile Gln Asn Asp
                 85                  90                  95

Ile Pro Phe Ala Leu Asn Leu Phe Glu Ile Leu Ser Arg Ser Ser Ile
            100                 105                 110

His Val Phe Val Gly Cys Phe Ser Asn Lys Asp Ala Thr Ile Ala Leu
        115                 120                 125

Leu Asn Glu Leu Gln Ile Arg Ile His Tyr Gly Glu Asp Thr His Val
130                 135                 140

Thr Tyr Leu Leu Ser Ile Ile Leu Gln Leu Leu Asn Lys Phe Lys Tyr
145                 150                 155                 160

Asn Phe Lys Glu Val Arg Phe Leu Val Lys Glu Leu Ile Leu Arg Ile
                165                 170                 175

Ser Glu Asp Glu Val Lys Ser Met Met Leu Ile Ile Phe Ala Glu Leu
            180                 185                 190

Gln Ser Ser Phe Gln Lys Asp Phe Asp Lys Ala Val Asp Phe Met
        195                 200                 205

Ser Ser Leu Ile Val Glu Ala Glu Ile Asp Val Gly Asn Asp Pro Leu
210                 215                 220

Ser Ile Ile Val Lys Thr Leu Ser Glu Leu Tyr Pro Ser Leu Thr Thr
225                 230                 235                 240

Leu Cys Ser Glu Ile Phe Leu Thr Lys Gly Leu Ser Lys Leu Phe Lys
                245                 250                 255

Lys Arg Val Phe Glu Glu Gln Asp Leu Gln Phe Thr Lys Glu Leu Leu
            260                 265                 270

Arg Leu Leu Ser Ser Ala Cys Ile Asp Glu Thr Met Arg Thr Tyr Ile
        275                 280                 285

Thr Glu Asn Tyr Leu Gln Leu Leu Glu Arg Ser Leu Asn Val Glu Asp
290                 295                 300

Val Gln Ile Tyr Ser Ala Leu Val Leu Val Lys Thr Trp Ser Phe Thr
305                 310                 315                 320

Lys Leu Thr Cys Ile Asn Leu Lys Gln Leu Ser Glu Ile Phe Ile Asn
                325                 330                 335

Ala Ile Ser Arg Arg Ile Met Pro Lys Ile Glu Asn Val Asn Glu Ser
            340                 345                 350

Ala Val Lys Leu Glu Glu Val Pro Lys Val Glu Met Ser Val Glu Ala
        355                 360                 365

Leu Ala Tyr Leu Ser Leu Lys Ala Ser Val Lys Ile Met Ile Arg Ser
370                 375                 380

Asn Glu Ser Phe Thr Glu Ile Leu Leu Thr Met Ile Lys Ser Gln Lys
385                 390                 395                 400

Met Thr His Cys Leu Tyr Gly Leu Leu Val Ile Met Ala Asn Leu Ser
                405                 410                 415

Thr Leu Pro Glu Glu Ser Asn Gly Ser Ser Gln Ser Ile Asn Asp Leu
            420                 425                 430

Lys Asn Tyr Ala Asp Leu Lys Gly Pro Gly Ala Asp Lys Val Gly Ala
        435                 440                 445

Glu Lys Glu Ser Lys Glu Asp Ile Leu Leu Phe Asn Glu Lys Tyr Ile
450                 455                 460

Leu Arg Thr Glu Leu Ile Ser Phe Leu Lys Arg Glu Met His Asn Leu
465                 470                 475                 480
```

```
Ser Pro Asn Cys Lys Gln Gln Val Val Arg Val Ile Tyr Asn Ile Thr
                485                 490                 495

Arg Ser Lys Asn Phe Ile Pro Gln Cys Ile Ser Gln Gly Gly Thr Thr
            500                 505                 510

Ile Ile Leu Glu Tyr Leu Ala Asn Lys Gln Asp Ile Gly Glu Pro Ile
        515                 520                 525

Arg Ile Leu Gly Cys Arg Ala Leu Thr Arg Met Leu Ile Phe Thr Asn
    530                 535                 540

Pro Gly Leu Ile Phe Lys Lys Tyr Ser Ala Leu Asn Ala Ile Pro Phe
545                 550                 555                 560

Leu Phe Glu Leu Leu Pro Arg Ser Thr Pro Val Asp Asp Asn Pro Leu
                565                 570                 575

His Asn Asp Glu Gln Ile Lys Leu Thr Asp Asn Tyr Glu Ala Leu Leu
            580                 585                 590

Ala Leu Thr Asn Leu Ala Ser Ser Glu Thr Ser Asp Gly Glu Glu Val
        595                 600                 605

Cys Lys His Ile Val Ser Thr Lys Val Tyr Trp Ser Thr Ile Glu Asn
    610                 615                 620

Leu Met Leu Asp Glu Asn Val Pro Leu Gln Arg Ser Thr Leu Glu Leu
625                 630                 635                 640

Ile Ser Asn Met Met Ser His Pro Leu Thr Ile Ala Ala Lys Phe Phe
                645                 650                 655

Asn Leu Glu Asn Pro Gln Ser Leu Arg Asn Phe Asn Ile Leu Val Lys
            660                 665                 670

Leu Leu Gln Leu Ser Asp Val Glu Ser Gln Arg Ala Val Ala Ala Ile
        675                 680                 685

Phe Ala Asn Ile Ala Thr Thr Ile Pro Leu Ile Ala Lys Glu Leu Leu
    690                 695                 700

Thr Lys Lys Glu Leu Ile Glu Asn Ala Ile Gln Val Phe Ala Asp Gln
705                 710                 715                 720

Ile Asp Asp Ile Glu Leu Arg Gln Arg Leu Leu Met Leu Phe Phe Gly
                725                 730                 735

Leu Phe Glu Val Ile Pro Asp Asn Gly Thr Asn Glu Val Tyr Pro Leu
            740                 745                 750

Leu Gln Glu Asn Gln Lys Leu Lys Asp Ala Leu Asn Met Ser Leu Lys
        755                 760                 765

Arg Gly Asp Ser Gly Pro Glu Phe Ser Ala Ala Ile Pro Val Ile Leu
    770                 775                 780

Ala Lys Ile Lys Val
785

<210> SEQ ID NO 31
<211> LENGTH: 947
<212> TYPE: PRT
<213> ORGANISM: Drosophila malanogaster

<400> SEQUENCE: 31

Met Thr Asn Thr Ile Asn Ser Glu Glu Val Ser Asp Ala Gly Ser Tyr
1               5                   10                  15

Lys Asp Lys Gly Asn Glu Ala Phe Lys Ala Ser Arg Trp Glu Glu Ala
            20                  25                  30

Val Glu His Tyr Gly Lys Ala Ile Lys Ala Gly Ser Lys His Lys Glu
        35                  40                  45

Leu Ala Val Phe Tyr Lys Asn Arg Ala Ala Ala Tyr Leu Lys Leu Gly
    50                  55                  60
```

```
Lys Tyr Glu Asn Ala Val Glu Asp Cys Thr Glu Ser Leu Lys Ala Ala
 65                  70                  75                  80

Pro Gly Asp Pro Lys Ala Leu Phe Arg Arg Ala Gln Ala Tyr Glu Ala
                 85                  90                  95

Leu Glu Lys Phe Glu Glu Ala Tyr Lys Asp Ala Thr Ala Leu Phe Lys
            100                 105                 110

Ala Asp Pro Gly Asn Lys Thr Val Gln Pro Met Leu Gln Arg Leu His
            115                 120                 125

Val Val Val Glu Glu Arg Ser Ala Arg Asn Ala Lys Thr Ser Thr Lys
130                 135                 140

Val Lys Gln Met Met Asp Leu Thr Phe Asp Leu Ala Thr Pro Ile Asp
145                 150                 155                 160

Lys Arg Arg Ala Ala Asn Asn Leu Val Leu Ala Lys Glu Gln
            165                 170                 175

Thr Gly Ala Glu Leu Leu Tyr Lys Asp His Cys Ile Ala Lys Val Ala
            180                 185                 190

Ser Leu Thr Lys Val Glu Lys Asp Gln Asp Ile Tyr Val Asn Met Val
            195                 200                 205

His Leu Val Ala Ala Leu Cys Glu Asn Ser Val Glu Arg Thr Lys Gly
210                 215                 220

Val Leu Thr Glu Leu Gly Val Pro Trp Phe Met Arg Val Leu Asp Gln
225                 230                 235                 240

Lys His Glu Asn Cys Val Ser Thr Ala Gln Phe Cys Leu Gln Thr Ile
                245                 250                 255

Leu Asn Ala Leu Ser Gly Leu Lys Asn Lys Pro Asp Ser Lys Pro Asp
            260                 265                 270

Lys Glu Leu Cys Thr Arg Asn Asn Arg Glu Ile Asp Thr Leu Leu Thr
            275                 280                 285

Cys Leu Val Tyr Ser Ile Thr Asp Arg Thr Ile Ser Gly Ala Ala Arg
            290                 295                 300

Asp Gly Val Ile Glu Leu Ile Thr Arg Asn Val His Tyr Thr Ala Leu
305                 310                 315                 320

Glu Trp Ala Glu Arg Leu Val Glu Ile Arg Gly Leu Cys Arg Leu Leu
                325                 330                 335

Asp Val Cys Ser Glu Leu Glu Asp Tyr Lys Tyr Glu Ser Ala Met Asp
            340                 345                 350

Ile Thr Gly Ser Ser Ser Thr Ile Ala Ser Val Cys Leu Ala Arg Ile
            355                 360                 365

Tyr Glu Asn Met Tyr Tyr Asp Glu Ala Lys Ala Arg Phe Thr Asp Gln
            370                 375                 380

Ile Asp Glu Tyr Ile Lys Asp Lys Leu Leu Ala Pro Asp Met Glu Ser
385                 390                 395                 400

Lys Val Arg Val Thr Val Ala Ile Thr Ala Leu Leu Asn Gly Pro Leu
            405                 410                 415

Asp Val Gly Asn Gln Val Val Ala Arg Glu Gly Ile Leu Gln Met Ile
            420                 425                 430

Leu Ala Met Ala Thr Thr Asp Asp Glu Leu Gln Gln Arg Val Ala Cys
            435                 440                 445

Glu Cys Leu Ile Ala Ala Ser Ser Lys Lys Asp Lys Ala Lys Ala Leu
            450                 455                 460

Cys Glu Gln Gly Val Asp Ile Leu Lys Arg Leu Tyr His Ser Lys Asn
465                 470                 475                 480
```

```
Asp Gly Ile Arg Val Arg Ala Leu Val Gly Leu Cys Lys Leu Gly Ser
                485                 490                 495

Tyr Gly Gly Gln Asp Ala Ala Ile Arg Pro Phe Gly Asp Gly Ala Ala
            500                 505                 510

Leu Lys Leu Ala Glu Ala Cys Arg Arg Phe Leu Ile Lys Pro Gly Lys
            515                 520                 525

Asp Lys Asp Ile Arg Arg Trp Ala Ala Asp Gly Leu Ala Tyr Leu Thr
            530                 535                 540

Leu Asp Ala Glu Cys Lys Glu Lys Leu Ile Glu Asp Lys Ala Ser Ile
545                 550                 555                 560

His Ala Leu Met Asp Leu Ala Arg Gly Gly Asn Gln Ser Cys Leu Tyr
                565                 570                 575

Gly Val Val Thr Thr Phe Val Asn Leu Cys Asn Ala Tyr Glu Lys Gln
            580                 585                 590

Glu Met Leu Pro Glu Met Ile Glu Leu Ala Lys Phe Ala Lys Gln His
            595                 600                 605

Ile Pro Glu Glu His Glu Leu Asp Asp Val Asp Phe Ile Asn Lys Arg
            610                 615                 620

Ile Thr Val Leu Ala Asn Glu Gly Ile Thr Thr Ala Leu Cys Ala Leu
625                 630                 635                 640

Ala Lys Thr Glu Ser His Asn Ser Gln Glu Leu Ile Ala Arg Val Leu
                645                 650                 655

Asn Ala Val Cys Gly Leu Lys Glu Leu Arg Gly Lys Val Val Gln Glu
                660                 665                 670

Gly Gly Val Lys Ala Leu Leu Arg Met Ala Leu Glu Gly Thr Glu Lys
            675                 680                 685

Gly Lys Arg His Ala Thr Gln Ala Leu Ala Arg Ile Gly Ile Thr Ile
            690                 695                 700

Asn Pro Glu Val Ser Phe Ser Gly Gln Arg Ser Leu Asp Val Ile Arg
705                 710                 715                 720

Pro Leu Leu Asn Leu Leu Gln Gln Asp Cys Thr Ala Leu Glu Asn Phe
                725                 730                 735

Glu Ser Leu Met Ala Leu Thr Asn Leu Ala Ser Met Asn Glu Ser Val
            740                 745                 750

Arg Gln Arg Ile Ile Lys Glu Gln Gly Val Ser Lys Ile Glu Tyr Tyr
            755                 760                 765

Leu Met Glu Asp His Leu Tyr Leu Thr Arg Ala Ala Ala Gln Cys Leu
            770                 775                 780

Cys Asn Leu Val Met Ser Glu Asp Val Ile Lys Met Phe Glu Gly Asn
785                 790                 795                 800

Asn Asp Arg Val Lys Phe Leu Ala Leu Leu Cys Glu Asp Glu Asp Glu
                805                 810                 815

Glu Thr Ala Thr Ala Cys Ala Gly Ala Leu Ala Ile Ile Thr Ser Val
            820                 825                 830

Ser Val Lys Cys Cys Glu Lys Ile Leu Ala Ile Ala Ser Trp Leu Asp
            835                 840                 845

Ile Leu His Thr Leu Ile Ala Asn Pro Ser Pro Ala Val Gln His Arg
850                 855                 860

Gly Ile Val Ile Ile Leu Asn Met Ile Asn Ala Gly Glu Glu Ile Ala
865                 870                 875                 880

Lys Lys Leu Phe Glu Thr Asp Ile Met Glu Leu Leu Ser Gly Leu Gly
                885                 890                 895

Gln Leu Pro Asp Asp Thr Arg Ala Lys Ala Arg Glu Val Ala Thr Gln
```

```
                900                 905                 910
Cys Leu Ala Ala Ala Glu Arg Tyr Arg Ile Ile Glu Arg Ser Asp Asn
        915                 920                 925

Ala Glu Ile Pro Asp Val Phe Ala Glu Asn Ser Lys Ile Ser Glu Ile
    930                 935                 940

Ile Asp Asp
945
```

<210> SEQ ID NO 32
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 32
cggcggtacc ttacaggtct tcttcagaga tcagtttctg ttcgcttgag tctgg          55

<210> SEQ ID NO 33
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 33
agcaccatgg aggatttgtc aaacgc                                          26

<210> SEQ ID NO 34
<211> LENGTH: 42
<212> TYPE: DNA
<213> ORGANISM: Artificial sequence
<220> FEATURE:
<223> OTHER INFORMATION: Synthetic Oligonucleotide

<400> SEQUENCE: 34
gggggaattc atggactaca aagacgatga cgacaagatg gc                        42

<210> SEQ ID NO 35
<211> LENGTH: 38
<212> TYPE: DNA
<213> ORGANISM: Artificial sequence
<220> FEATURE:
<223> OTHER INFORMATION: Synthetic Oligonucleotide

<400> SEQUENCE: 35
gggggaattc ctactactag aacgccggct gaacagtc                             38

<210> SEQ ID NO 36
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 36
catggaattc atgagcaagg tcgagaaga                                       29

<210> SEQ ID NO 37
<211> LENGTH: 31
<212> TYPE: DNA
<213> ORGANISM: Artificial sequence
<220> FEATURE:
<223> OTHER INFORMATION: Synthetic oligonucleotide -continued

<400> SEQUENCE: 37
catgagatct tgattactcc cttcgctcga g                              31

<210> SEQ ID NO 38
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 38
gcacaatcat atgcatcacc accatcatca cagcaaggtc gagaagaaat gc       52

<210> SEQ ID NO 39
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 39
gcacaatgga tccttactcc cttcgctcga gcatt                          35

<210> SEQ ID NO 40
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 40
gcacaatcat atgcatcacc accatcatca cacctgccct ccccgcgtcc gt       52

<210> SEQ ID NO 41
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 41
gcacaatgga tccttatttc agcagcatct tgacaaagt                      39

<210> SEQ ID NO 42
<211> LENGTH: 1068
<212> TYPE: PRT
<213> ORGANISM: Plasmodium falciparum

<400> SEQUENCE: 42

Asn Lys Asp Asn Asn Lys Ser Glu Ile Asn Arg Ile Asn Glu Lys
1               5                   10                  15

Leu Arg Asp Ile Met Lys Ile Ile Asp Gln Asn Lys Asn Asp Pro Tyr
            20                  25                  30

Lys Asn Ile Ser Asn Ile Lys Lys Tyr Leu Leu Asp Glu Asn Thr Asn
        35                  40                  45

Asn Ile Asn Asp Ile Glu Glu Asn Asn Lys Lys Ile Lys Leu Leu His
    50                  55                  60

Ser Ile Tyr Asn Gln Lys Phe Tyr Ile Leu Leu Lys Glu Asn Ile Phe
65                  70                  75                  80

Leu Phe Leu Phe Asp Phe Ile Lys Lys Asn Asn Asp Ile Ser Asn Tyr
                85                  90                  95

Asp Asp Cys Asn Asn Asn Asn Asn Asn Asn Asn Leu Tyr Ser His Asn

```
                    100                 105                 110
Ile Asn Ser Leu Leu Leu Glu Lys Thr Ala Ile Tyr Val Ile Tyr Lys
            115                 120                 125
Ile Leu Ser Lys Leu Asp Asn Glu His Ile Ile Ile Glu Asn Ser Lys
            130                 135                 140
Asp Asp Asn Tyr Asn Lys Asn Arg Asn Ile Cys Ile Asn Lys Leu Asp
145                 150                 155                 160
Asn Ser Lys Leu Gln Tyr Tyr Tyr Asp Leu Asp Tyr Ile Lys Met Ile
                165                 170                 175
Leu Ser Phe Asn Glu Tyr Phe Thr Lys Asp Trp Ile Tyr Asn Tyr Ile
                180                 185                 190
Lys Lys Lys Ile Asn Ile Leu Glu Asn Leu Lys Phe Ser Lys Asp Glu
            195                 200                 205
Thr Leu Tyr Lys Glu His Val Asp Ile Leu Ile Tyr Ile Ile Asn Ile
            210                 215                 220
Met Lys Tyr Val Tyr Val Ile Asn Asn Asp Tyr Ile Leu Asn Ile Ile
225                 230                 235                 240
Asn Ser Tyr Tyr Leu Asn Ser Asp Asn Ser Asn Ile Asn Asn Ser Gly
                245                 250                 255
Ile Asn Ala Leu Thr Phe Leu Cys Lys Lys Gln Phe Leu Thr Gln
            260                 265                 270
Asn Ser Lys Asp Asn Arg Lys Lys Lys Asn Asp Leu Leu Glu Met Leu
            275                 280                 285
Lys Lys Glu Asn Tyr Leu Asn Ile Gln Asn Asn Ile Gln Asn Asn Asn
            290                 295                 300
Asn Asn Asn Asn Tyr Tyr Phe Tyr Lys Asn Glu Phe Ile Glu Phe His
305                 310                 315                 320
Phe Ser Asp Ser His Lys Tyr Pro Leu Cys Ile Asn Ser Glu Ile Lys
                325                 330                 335
Lys Ile Ile Gln Asn Val Ile Gly Met Tyr Glu His Phe Ser Ser Ser
            340                 345                 350
Ile Glu Tyr Thr Leu Ile Leu Ile Phe Thr Leu Leu His Asp Pro Gln
            355                 360                 365
Arg Pro Lys Glu Lys Asp Ile Glu Met Asn Asp Val Ile Tyr Asp Cys
            370                 375                 380
Ile Asp Asn Tyr Phe His His Asn Glu Asn Ile Leu Ile Glu Trp Phe
385                 390                 395                 400
Val Cys Ile Lys Cys Leu Phe Leu Val Asp Lys Asn Ile Ile Leu Asn
                405                 410                 415
Tyr Leu Ile Gly Lys Thr Glu Tyr Ile Val Lys Ile Leu His Phe Ile
                420                 425                 430
Thr Asn Cys Ile Gly Arg Lys Thr Lys Glu Glu Leu Ser Ile Tyr Ile
            435                 440                 445
Asp Val Leu Leu Leu Leu Asn Ile Ser Glu Ile Arg Phe Met Phe
450                 455                 460
Thr Asn Tyr Ile Asp Met Tyr Ile Asn Ile Met Lys Ser Leu Asn Tyr
465                 470                 475                 480
Asp Gln Cys Phe Leu Lys Leu Leu Leu Gly Thr Phe Lys Leu Tyr Met
                485                 490                 495
His Asn Ile Asp Phe Lys Gln Gln Ile Gln Asp Asn Val Asp Leu Phe
            500                 505                 510
Phe Tyr Ala Lys Glu Ile Leu Lys Gln Phe Leu Leu Thr Tyr Asp Asn
            515                 520                 525
```

```
Asp Ala Asp Gly Lys Asn Asn Thr Asn Asn Asp Lys Arg Glu Glu Asn
        530                 535                 540

Glu Glu Gln Thr Ser His Leu Asn Tyr Ser Asn Leu Asn Ser Tyr Thr
545                 550                 555                 560

Cys Cys Val Lys Lys Cys Asp Asp Asn Asp Thr Lys Lys Lys Asp Ile
                565                 570                 575

Ile Asn Gln Lys Lys Asp Glu Lys Asn Lys Lys His Cys Glu Leu Val
                580                 585                 590

Asp Lys Lys Lys Lys Asp His Thr Tyr Ile His Ser Asn Met Ser Cys
                595                 600                 605

Glu Lys Thr Leu Lys Asp Leu Ile Glu Met Leu Phe Tyr Leu Ser Leu
        610                 615                 620

His Ile Glu Phe Lys Lys Gln Leu Leu Glu Glu Lys Asn Asn Tyr Ile
625                 630                 635                 640

Leu Phe Phe Leu Ile Lys Val Gly His Asp Ile Asn Lys Lys Lys Leu
                645                 650                 655

Asp Asn Thr Tyr Lys Tyr Ile Tyr Cys Asn Thr Ile Asn Asn Leu Ile
                660                 665                 670

Leu Thr Lys Asn Asp Glu Lys Ile Lys Arg Arg Glu Ile Asn Lys Thr
        675                 680                 685

Asn Leu Ser Asn Phe Asp Asn Glu Gln Ile Glu Ala Leu Glu Gln Phe
        690                 695                 700

Tyr Asp Lys Leu Pro Lys Glu Ala Arg Pro Lys Thr Asp Pro Leu Tyr
705                 710                 715                 720

Asp Tyr Gly Asp Glu Glu Thr Ser Asn Lys Leu Ile Asp Leu Leu Leu
                725                 730                 735

Tyr Asn Glu Lys Tyr Gln Met Asn His Ile Asn Asp Lys Asn Lys Asn
                740                 745                 750

Asn Asn Asn Asn Asn Ile Asn Asn Gly Asn Val Ser Pro Leu Ser
        755                 760                 765

Ser Lys Cys Ser Tyr Thr Asn Gly Thr Ile Ile Asn Ile Ile Tyr Asn
        770                 775                 780

Phe Ile Asn Ser Asn Phe Phe Thr Thr Asn Ile Ala Glu Ser Val Cys
785                 790                 795                 800

Glu Ile Ile Ser Lys Phe Val Lys Asn Thr Asn Asn Ile Gly Ile Val
                805                 810                 815

Leu Val Asn Asn Gly Leu Lys Thr Leu Leu Ala Ser Lys His Ile
                820                 825                 830

Thr Asn Lys Lys Asn Cys Ala Leu Ala Leu Ser Glu Ile Phe Ile Tyr
        835                 840                 845

Thr Asn Pro Lys Leu Ile His Phe Tyr Glu Ala Tyr Asp Ser Leu Pro
850                 855                 860

Leu Leu Ile Glu Gln Leu Lys Ser Asp Glu Glu Leu Leu Ile Phe Lys
865                 870                 875                 880

Thr Leu Met Ala Ile Thr Asn Ile Leu Thr Ile Asp Glu Asn Val Ala
                885                 890                 895

Ile Lys Ala Met Gln Leu Asn Leu Trp Tyr Lys Cys Phe Asp Ile Leu
                900                 905                 910

Ser Thr Glu Asn Glu Tyr Ile Lys Ser Ala Ser Leu Glu Cys Ile Cys
        915                 920                 925

Asn Leu Cys Ser Gln Ser His Val His Gln Tyr Ile Tyr Asp Lys Tyr
        930                 935                 940
```

```
Gln Thr Ile Met Lys Ser Lys Asn Glu Ser Asp Lys Asp Ile Leu Phe
945                 950                 955                 960

Val Asp Ile Gln Ile Ile Tyr Ser Phe Thr Met Glu Tyr Gln Asn Tyr
                965                 970                 975

Lys Cys Val Phe Ala Ala Thr Gly Ala Leu Gly Met Leu Ser Ser Asp
            980                 985                 990

Leu Arg Leu Pro Tyr Tyr Leu Val Arg Thr Lys Gly Ile Asp His Ile
        995                 1000                1005

Phe Ser  Ser Phe Asn Asn Thr  Thr Asp Gln Asn Ile  Leu Leu Arg
    1010                 1015                 1020

Ile Leu  Thr Phe Phe Asn Asn  Ile Met Thr Cys Asp  Asp Ile Pro
    1025                 1030                 1035

Asp Asp  Ile Leu Lys Lys Ile  Lys Thr Tyr Val Glu  Lys Lys Lys
    1040                 1045                 1050

Asp Leu  Asn Glu Glu Asn Thr  Gln Met Ala Asn Phe  Ile Leu Gln
    1055                 1060                 1065

<210> SEQ ID NO 43
<211> LENGTH: 615
<212> TYPE: DNA
<213> ORGANISM: Plasmodium falciparum

<400> SEQUENCE: 43
atgggaaata aatgttcaag aagcaaagta aaggaaccca acgtaaaga tattgatgaa      60 ttagctgaac gtgaaaattt aaaaaaacaa tctgaagaaa taattgaaga aaaaccagaa     120
gaagttgttg agcaagtaga agaaacacat gaagaacctc ttgaacaaga acaggaactg     180
gatgaacaga aaatagaaga agaagaagaa gaacctgaac aagtaccaaa agaagaaata     240
gattatgcaa ctcaagaaaa taatcatttt gaagaaaaac attagaaga tttagaaga     300 tctaattcag atatttattc agaatctcaa aaatttgata atgctagtga taaattagaa     360
acaggaactc aattaacctt atctactgaa gccactggtg ccgtacaaca aataactaaa     420
ttaagtgaac ccgcccatga agaaagtata tattttactt atagatctgt aacaccttgt     480
gatatgaata aactcgatga aaccgctaaa gttttttcaa gaagatgtgg atgtgatctt     540
ggtgaacgtc atgatgaaaa tgcatgtaaa atttgtagaa aaattgattt atccgataca     600
cctttattga gctaa                                                     615

<210> SEQ ID NO 44
<211> LENGTH: 204
<212> TYPE: PRT
<213> ORGANISM: Plasmodium falciparum

<400> SEQUENCE: 44

Met Gly Asn Lys Cys Ser Arg Ser Lys Val Lys Glu Pro Lys Arg Lys
1               5                   10                  15

Asp Ile Asp Glu Leu Ala Glu Arg Glu Asn Leu Lys Lys Gln Ser Glu
            20                  25                  30

Glu Ile Ile Glu Glu Lys Pro Glu Val Val Glu Gln Val Glu Glu
        35                  40                  45

Thr His Glu Glu Pro Leu Glu Gln Glu Gln Leu Asp Glu Gln Lys
    50                  55                  60

Ile Glu Glu Glu Glu Glu Pro Glu Gln Val Pro Lys Glu Glu Ile
65                  70                  75                  80

Asp Tyr Ala Thr Gln Glu Asn Lys Ser Phe Glu Glu Lys His Leu Glu
                85                  90                  95
```

Asp Leu Glu Arg Ser Asn Ser Asp Ile Tyr Ser Glu Ser Gln Lys Phe
            100                 105                 110

Asp Asn Ala Ser Asp Lys Leu Glu Thr Gly Thr Gln Leu Thr Leu Ser
        115                 120                 125

Thr Glu Ala Thr Gly Ala Val Gln Gln Ile Thr Lys Leu Ser Glu Pro
    130                 135                 140

Ala His Glu Glu Ser Ile Tyr Phe Thr Tyr Arg Ser Val Thr Pro Cys
145                 150                 155                 160

Asp Met Asn Lys Leu Asp Glu Thr Ala Lys Val Phe Ser Arg Arg Cys
            165                 170                 175

Gly Cys Asp Leu Gly Glu Arg His Asp Glu Asn Ala Cys Lys Ile Cys
        180                 185                 190

Arg Lys Ile Asp Leu Ser Asp Thr Pro Leu Leu Ser
        195                 200

<210> SEQ ID NO 45
<211> LENGTH: 1823
<212> TYPE: DNA
<213> ORGANISM: Toxoplasma gondii

<400> SEQUENCE: 45
gtgagatttc ctttcagcga attttgtgat ctcaagagcg agaggcacaa ctgtatttga    60
gaacttttgc ttttcagcg ttgcacgagt tttaaatctc ggtgtgactg ttcgaaaccc    120
tgtcatttcc ctccgagaag atcggtcgac ggcgcgcgga caaccgcgtg cgtaaaaggt   180
gtttgctatt tcgccgggga gaaaagcggc cgtaaagtcg gaagacttgc cagacgagac   240
gagaaactgg gtgcggcacg gcatttcatc attctgtatg tgttgttttc cattcgaaga   300 aagtttgtt tctcgcggca gagggaaagg cgcgcaccga acctgcccgc agtttccggt    360
acatccacgc acacacttcg gtggctgaaa cgccgcgatt gttccgttct tgtgttcgcg   420
acttcgactc tctgaatcgc tccccccacac atcttttgtt gtcgcccct caactttttc    480 gcacttttc gattcgaaat gggaaacgcg tgcaagaaga cacggccaa gacgccgacc     540 cggaaggagg cggaggacct ggctgagaag gagcggcagg agcgggaggc gaaggagaag   600
gctgaggctg aagagaaggc tcgcgccgaa gcggagaaga acgcagcaga caaagcggag   660
gctgaacgta gagcggcaga ggcgcgagag cgcgaagaat cagccaggaa ggaggcggag   720
gctgaggcgg cccgcaaggc cgaagcagag gcggctgagg ccgagcgcct ccggaaggaa   780
gcagagaaga aaaaggcgga ggaggcgaaa cgcaaggcgg aggaggagca gcgcgccgca   840
gccgaggaag cggagcaaag agcgcgggag gaggccgagc gccgcaaagc tgaagctgcg   900
gcggcagcga gcgcgagcg ccagatgcag gaggcgctga agcaagagga aatgtcaccg    960
agagagaagt acgacaagtt agccagcccc gaagactccg catccgagac cacgatggcg   1020
acacagccgc agaaagtcgc cgagcacagc agcgcggcgg tcacagacag atcagtggtg   1080
gggtacaccg tgactccatg cgacatggca tcaattgacg agacagctaa gtacttgtca   1140
aagcgctgcg gttgcgacct aggcgaccaa cacgacgaaa acgagtgccc tatttgccgc   1200
cacatcgact tgtcggatgc acccttgttg aactgagtgc gtaactgttt ctgtgttttt   1260
ctactctacg gccccggctt cgggatctgt gtctgtatag cgtgcgctta taaacgcgta   1320
aacttcgtgt ttaagaaaga ttagcaaggg ttaggacggt gaagaagagt ttgggaccgt   1380
gttttttcga caaacgtcgg gttgctagta tcgcacgtag gtgtgcacta ccccgctctc   1440
catgtaggcg tagtctgtgt agcaacagga cggttggcgg caaacagaaa gggaggaaat   1500

```
ttctgcgggt tcttcgagtc tgagctgtcg cgaaaagctc caaaagcgaa ctggctcccc    1560
gcagtctatg ggggacgcac ccgccggtag gggtgaagtg gctcacaggc ttcgcccgcc    1620
tgtccgtacg tgcagggcag aatcctgccc gaacgtgaga caaccgtca ttccccgtcg     1680 tcacatagtt cttttcctcg accatcccca cgtgacacca ctggtgtgcg aatgcggcgc    1740
agcgttcgac tgtcttccgc gaaaggcgat gcttacaaac gcacgctcgc atgacatacg    1800
tgccgtaaag aggaaaccct tct                                            1823
```

<210> SEQ ID NO 46
<211> LENGTH: 245
<212> TYPE: PRT
<213> ORGANISM: Toxoplasma gondii

<400> SEQUENCE: 46

```
Met Gly Asn Ala Cys Lys Lys Asn Thr Ala Lys Thr Pro Thr Arg Lys
1               5                   10                  15

Glu Ala Glu Asp Leu Ala Glu Lys Glu Arg Gln Glu Arg Glu Ala Lys
            20                  25                  30

Glu Lys Ala Glu Ala Glu Lys Ala Arg Ala Glu Ala Glu Lys Asn
        35                  40                  45

Ala Ala Asp Lys Ala Glu Ala Glu Arg Arg Ala Ala Glu Ala Arg Glu
    50                  55                  60

Arg Glu Glu Ser Ala Arg Lys Glu Ala Glu Ala Glu Ala Ala Arg Lys
65                  70                  75                  80

Ala Glu Ala Glu Ala Glu Ala Glu Arg Leu Arg Lys Glu Ala Glu
                85                  90                  95

Lys Lys Lys Ala Glu Glu Ala Lys Arg Lys Ala Glu Glu Gln Arg
            100                 105                 110

Ala Ala Ala Glu Glu Ala Glu Gln Arg Ala Arg Glu Glu Ala Glu Arg
        115                 120                 125

Arg Lys Ala Glu Ala Ala Ala Ala Ala Glu Arg Glu Arg Gln Met Gln
    130                 135                 140

Glu Ala Leu Lys Gln Glu Glu Met Ser Pro Arg Glu Lys Tyr Asp Lys
145                 150                 155                 160

Leu Ala Ser Pro Glu Asp Ser Ala Ser Glu Thr Thr Met Ala Thr Gln
                165                 170                 175

Pro Gln Lys Val Ala Glu His Ser Ser Ala Ala Val Thr Asp Arg Ser
            180                 185                 190

Val Val Gly Tyr Thr Val Thr Pro Cys Asp Met Ala Ser Ile Asp Glu
        195                 200                 205

Thr Ala Lys Tyr Leu Ser Lys Arg Cys Gly Cys Asp Leu Gly Asp Gln
    210                 215                 220

His Asp Glu Asn Glu Cys Pro Ile Cys Arg His Ile Asp Leu Ser Asp
225                 230                 235                 240

Ala Pro Leu Leu Asn
                245
```

<210> SEQ ID NO 47
<211> LENGTH: 416
<212> TYPE: DNA
<213> ORGANISM: Toxoplasma gondii

<400> SEQUENCE: 47

```
atgacctgcc ctccccgcgt ccgtgaggcc ttcgccctct tcgacactga cggagatggt    60
gagatctctg gccgcgacct cgtcctcgcc atccgctcat gcggtgtgtc tcccaccca    120
```

```
gacgaaatca aggcactccc catgtcaatg gcgtggcctg attttgaggc gtggatgtcg        180
aagaaactgg cgtcctacaa ccctgaggag gagttgatca aatctttcaa ggcttttgac        240
cggtcgaacg acggcaccgt gtctgcggac gagctttctc aagttatgct cgctctcggc        300
gagttgcttt ccgacgaaga agtcaaggcc atgatcaagg aagccgaccc gaacggcact        360
ggcaagatcc agtacgccaa ctttgtcaag atgctgctga ataaggatc cattgt            416
```

<210> SEQ ID NO 48
<211> LENGTH: 134
<212> TYPE: PRT
<213> ORGANISM: Toxoplasma gondii

<400> SEQUENCE: 48

```
Met Thr Cys Pro Pro Arg Val Arg Glu Ala Phe Ala Leu Phe Asp Thr
1               5                   10                  15

Asp Gly Asp Gly Glu Ile Ser Gly Arg Asp Leu Val Leu Ala Ile Arg
            20                  25                  30

Ser Cys Gly Val Ser Pro Thr Pro Asp Glu Ile Lys Ala Leu Pro Met
        35                  40                  45

Ser Met Ala Trp Pro Asp Phe Glu Ala Trp Met Ser Lys Lys Leu Ala
    50                  55                  60

Ser Tyr Asn Pro Glu Glu Glu Leu Ile Lys Ser Phe Lys Ala Phe Asp
65                  70                  75                  80

Arg Ser Asn Asp Gly Thr Val Ser Ala Asp Glu Leu Ser Gln Val Met
                85                  90                  95

Leu Ala Leu Gly Glu Leu Leu Ser Asp Glu Glu Val Lys Ala Met Ile
            100                 105                 110

Lys Glu Ala Asp Pro Asn Gly Thr Gly Lys Ile Gln Tyr Ala Asn Phe
        115                 120                 125

Val Lys Met Leu Leu Lys
    130
```

<210> SEQ ID NO 49
<211> LENGTH: 139
<212> TYPE: PRT
<213> ORGANISM: Plasmodium falciparum

<400> SEQUENCE: 49

```
Met Glu Glu Ile Ile Asn Glu Val Glu Leu Thr Ser Leu Phe Asn Lys
1               5                   10                  15

Ile Ser Glu Gly Ser Arg Thr Ile His Phe Glu Asp Ala Met Glu Ile
            20                  25                  30

Ile Tyr Lys Met Gly Tyr Val Pro Ser Lys Glu Asp Ile Asn Glu Phe
        35                  40                  45

Asn Asn Met Thr Lys Gly Val Cys Ser Leu Ser Asn Ile Lys Lys Phe
    50                  55                  60

Cys Asn Lys Ile Arg Ser Leu Asn Tyr Ser Thr Glu Gly Leu Leu Asp
65                  70                  75                  80

Ile Phe His Phe Tyr Asp Thr Asn Lys Thr Gly Lys Ile Ser Lys Glu
                85                  90                  95

Lys Leu Lys Leu Leu Phe Thr Thr Val Gly Ser Lys Met Ser Val Asp
            100                 105                 110

Glu Met Asp Thr Ile Ile Asn Glu Leu Cys Asn Asn Asp Glu Asn Ile
        115                 120                 125

Asp Tyr Lys Glu Phe Leu Asn Arg Ile Leu Asn
    130                 135
```

-continued

```
<210> SEQ ID NO 50
<211> LENGTH: 420
<212> TYPE: DNA
<213> ORGANISM: Plasmodium falciparum

<400> SEQUENCE: 50
atggaggaaa taattaatga agtggaattg acttctcttt ttaacaagat atcagaaggg      60
tcgagaacta tccattttga ggatgccatg gaaataatat ataaaatggg ttatgttcct     120
tcaaaagaag atataaatga atttaacaac atgacaaaag gtgtttgttc tttatccaat     180
ataaaaaagt tctgcaataa aataaggtca ttgaattatt ccactgaagg tttgttggat     240
atatttcatt tttatgatac aaataaaaca ggaaaaattt ctaaagaaaa acttaaactc     300
ttatttacaa cagttggttc aaaaatgtcg gttgatgaaa tggatacaat aataaatgaa     360
ttatgtaata acgatgaaaa catagactat aaggaatttc taaacaggat attaaattag     420
```